(12) United States Patent
Bank et al.

(10) Patent No.: US 10,492,705 B2
(45) Date of Patent: Dec. 3, 2019

(54) ANTERIOR AND POSTERIOR ELECTRODE SIGNALS

(71) Applicants: REGENTS OF THE UNIVERSITY OF MINNESOTA, Minneapolis, MN (US); ALLINA HEALTH SYSTEM, St. Paul, MN (US)

(72) Inventors: Alan J. Bank, Edina, MN (US); Antonia E. Curtin, Minneapolis, MN (US); Ryan M. Gage, Minneapolis, MN (US); Kevin V. Burns, St. Anthony, MN (US)

(73) Assignees: REGENTS OF THE UNIVERSITY OF MINNESOTA, Minneapolis, MN (US); ALLINA HEALTH SYSTEM, St. Paul, MN (US)

( * ) Notice: Subject to any disclaimer, the term of this patent is extended or adjusted under 35 U.S.C. 154(b) by 0 days.

(21) Appl. No.: 16/229,256

(22) Filed: Dec. 21, 2018

(65) Prior Publication Data
US 2019/0192035 A1    Jun. 27, 2019

Related U.S. Application Data

(60) Provisional application No. 62/609,935, filed on Dec. 22, 2017.

(51) Int. Cl.
*A61B 5/04* (2006.01)
*A61B 5/0408* (2006.01)
(Continued)

(52) U.S. Cl.
CPC ...... *A61B 5/04087* (2013.01); *A61B 5/04011* (2013.01); *A61B 5/0452* (2013.01);
(Continued)

(58) Field of Classification Search
CPC ............ A61B 5/04087; A61B 5/04011; A61B 5/7203; A61B 5/6823; A61B 5/6805; A61N 1/3904; A61N 1/3627; A61N 1/3956

See application file for complete search history.

(56) References Cited

U.S. PATENT DOCUMENTS

| 4,233,987 A | 11/1980 | Feingold |
| 4,402,323 A | 9/1983 | White |

(Continued)

FOREIGN PATENT DOCUMENTS

| CN | 1043621 A | 11/1990 |
| CN | 1253761 A | 5/2000 |

(Continued)

OTHER PUBLICATIONS

International Search Report and Written Opinion dated May 3, 2012 for International Application No. PCT/US2012/036262; 9 pages.

(Continued)

*Primary Examiner* — Rex R Holmes
(74) *Attorney, Agent, or Firm* — Mueting, Raasch & Gebhardt, PA

(57) ABSTRACT

The exemplary systems, methods, and interfaces may obtain and analyze electrode signals from a plurality of external electrodes. The electrode signals may include at least an anterior set of electrode signals and a posterior set of electrode signals. The anterior and posterior sets of electrode signals may be used to generate, or provide, various metrics of cardiac electrical heterogeneity and various graphical depictions that may be useful in assessing a patient's cardiac functionality.

22 Claims, 18 Drawing Sheets

(51) Int. Cl.
*A61N 1/39* (2006.01)
*A61B 5/00* (2006.01)
*A61B 5/0452* (2006.01)
*A61N 1/362* (2006.01)

(52) U.S. Cl.
CPC ........ *A61B 5/04085* (2013.01); *A61B 5/7203* (2013.01); *A61N 1/3904* (2017.08); *A61B 5/6805* (2013.01); *A61B 5/6823* (2013.01); *A61N 1/3627* (2013.01); *A61N 1/3956* (2013.01)

(56) References Cited

U.S. PATENT DOCUMENTS

| | | |
|---|---|---|
| 4,428,378 A | 1/1984 | Anderson et al. |
| 4,497,326 A | 2/1985 | Curry |
| 4,566,456 A | 1/1986 | Koning et al. |
| 4,593,702 A | 6/1986 | Kepski |
| 4,674,511 A | 6/1987 | Cartmell |
| 4,763,660 A | 8/1988 | Kroll et al. |
| 4,777,955 A | 10/1988 | Brayten et al. |
| 4,787,389 A | 11/1988 | Tarjan |
| 4,979,507 A | 12/1990 | Heinz et al. |
| 5,052,388 A | 10/1991 | Sivula et al. |
| 5,054,496 A | 10/1991 | Wen et al. |
| 5,311,873 A | 5/1994 | Savard et al. |
| 5,331,960 A | 7/1994 | Lavine |
| 5,334,220 A | 8/1994 | Sholder |
| 5,443,492 A | 8/1995 | Stokes et al. |
| 5,485,849 A | 1/1996 | Panescu et al. |
| 5,514,163 A | 5/1996 | Markowitz et al. |
| 5,552,645 A | 9/1996 | Weng |
| 5,628,778 A | 5/1997 | Kruse et al. |
| 5,671,752 A | 9/1997 | Sinderby et al. |
| 5,683,429 A | 11/1997 | Mehra |
| 5,683,432 A | 11/1997 | Goedeke et al. |
| 5,687,737 A | 11/1997 | Branham et al. |
| 5,810,740 A | 9/1998 | Paisner |
| 5,876,336 A | 3/1999 | Swanson et al. |
| 5,891,045 A | 4/1999 | Albrecht et al. |
| 5,922,014 A | 7/1999 | Warman et al. |
| 6,055,448 A | 4/2000 | Anderson et al. |
| 6,128,535 A | 10/2000 | Maarse et al. |
| 6,141,588 A | 10/2000 | Cox et al. |
| 6,187,032 B1 | 2/2001 | Ohyu et al. |
| 6,205,357 B1 | 3/2001 | Ideker et al. |
| 6,226,542 B1 | 5/2001 | Reisfeld |
| 6,236,883 B1 | 5/2001 | Ciaccio et al. |
| 6,243,603 B1 | 6/2001 | Ideker et al. |
| 6,246,898 B1 | 6/2001 | Vesely et al. |
| 6,301,496 B1 | 10/2001 | Reisfeld |
| 6,311,089 B1 | 10/2001 | Mann et al. |
| 6,330,476 B1 | 12/2001 | Ben-Haim et al. |
| 6,358,214 B1 | 3/2002 | Tereschouk |
| 6,377,856 B1 | 4/2002 | Carson |
| 6,381,493 B1 | 4/2002 | Stadler et al. |
| 6,393,316 B1 | 5/2002 | Gillberg et al. |
| 6,418,346 B1 | 7/2002 | Nelson et al. |
| 6,442,433 B1 | 8/2002 | Linberg |
| 6,456,867 B2 | 9/2002 | Reisfeld |
| 6,473,638 B2 | 10/2002 | Ferek-Petric |
| 6,480,745 B2 | 11/2002 | Nelson et al. |
| 6,484,118 B1 | 11/2002 | Govari |
| 6,507,756 B1 | 1/2003 | Heynen et al. |
| 6,532,379 B2 | 3/2003 | Stratbucker |
| 6,584,343 B1 | 6/2003 | Ransbury et al. |
| 6,599,250 B2 | 7/2003 | Webb et al. |
| 6,625,482 B1 | 9/2003 | Panescu et al. |
| 6,640,136 B1 | 10/2003 | Helland et al. |
| 6,650,927 B1 | 11/2003 | Keidar |
| 6,766,189 B2 | 7/2004 | Yu et al. |
| 6,772,004 B2 | 8/2004 | Rudy |
| 6,804,555 B2 | 10/2004 | Warkentin |
| 6,847,836 B1 | 1/2005 | Sujdak |
| 6,856,830 B2 | 2/2005 | He |
| 6,882,882 B2 | 4/2005 | Struble et al. |
| 6,885,889 B2 | 4/2005 | Chinchoy |
| 6,915,149 B2 | 7/2005 | Ben-Haim |
| 6,968,237 B2 | 11/2005 | Doan et al. |
| 6,975,900 B2 | 12/2005 | Rudy et al. |
| 6,978,184 B1 | 12/2005 | Marcus et al. |
| 6,980,675 B2 | 12/2005 | Evron et al. |
| 7,016,719 B2 | 3/2006 | Rudy et al. |
| 7,031,777 B2 | 4/2006 | Hine et al. |
| 7,058,443 B2 | 6/2006 | Struble |
| 7,062,315 B2 | 6/2006 | Koyrakh et al. |
| 7,092,759 B2 | 8/2006 | Nehls et al. |
| 7,142,922 B2 | 11/2006 | Spinelli et al. |
| 7,184,835 B2 | 2/2007 | Kramer et al. |
| 7,215,998 B2 | 5/2007 | Wesselink et al. |
| 7,238,158 B2 | 7/2007 | Abend |
| 7,286,866 B2 | 10/2007 | Okerlund et al. |
| 7,308,297 B2 | 12/2007 | Reddy et al. |
| 7,308,299 B2 | 12/2007 | Burrell et al. |
| 7,313,444 B2 | 12/2007 | Pianca et al. |
| 7,321,677 B2 | 1/2008 | Evron et al. |
| 7,346,381 B2 | 3/2008 | Okerlund et al. |
| 7,398,116 B2 | 7/2008 | Edwards |
| 7,426,412 B1 | 9/2008 | Schecter |
| 7,454,248 B2 | 11/2008 | Burrell et al. |
| 7,499,743 B2 | 3/2009 | Vass et al. |
| 7,509,170 B2 | 3/2009 | Zhang et al. |
| 7,565,190 B2 | 7/2009 | Okerlund et al. |
| 7,587,074 B2 | 9/2009 | Zarkh et al. |
| 7,599,730 B2 | 10/2009 | Hunter et al. |
| 7,610,088 B2 | 10/2009 | Chinchoy |
| 7,613,500 B2 | 11/2009 | Vass et al. |
| 7,616,993 B2 | 11/2009 | Müssig et al. |
| 7,664,550 B2 | 2/2010 | Eick et al. |
| 7,684,863 B2 | 3/2010 | Parikh et al. |
| 7,742,629 B2 | 6/2010 | Zarkh et al. |
| 7,747,047 B2 | 6/2010 | Okerlund et al. |
| 7,751,882 B1 | 7/2010 | Helland et al. |
| 7,769,451 B2 | 8/2010 | Yang et al. |
| 7,778,685 B2 | 8/2010 | Evron et al. |
| 7,778,686 B2 | 8/2010 | Vass et al. |
| 7,787,951 B1 | 8/2010 | Min |
| 7,813,785 B2 | 10/2010 | Okerlund et al. |
| 7,818,040 B2 | 10/2010 | Spear et al. |
| 7,848,807 B2 | 12/2010 | Wang |
| 7,860,580 B2 | 12/2010 | Falk et al. |
| 7,894,889 B2 | 2/2011 | Zhang |
| 7,912,544 B1 | 3/2011 | Min et al. |
| 7,917,214 B1 | 3/2011 | Gill et al. |
| 7,941,213 B2 | 5/2011 | Markowitz et al. |
| 7,953,475 B2 | 5/2011 | Harlev et al. |
| 7,953,482 B2 | 5/2011 | Hess |
| 7,983,743 B2 | 7/2011 | Rudy et al. |
| 7,996,063 B2 | 8/2011 | Vass et al. |
| 7,996,070 B2 | 8/2011 | van Dam et al. |
| 8,010,194 B2 | 8/2011 | Muller |
| 8,019,402 B1 | 9/2011 | Kryzpow et al. |
| 8,019,409 B2 | 9/2011 | Rosenberg et al. |
| 8,032,229 B2 | 10/2011 | Gerber et al. |
| 8,036,743 B2 | 10/2011 | Savage et al. |
| 8,060,185 B2 | 11/2011 | Hunter et al. |
| 8,150,513 B2 | 4/2012 | Chinchoy |
| 8,160,700 B1 | 4/2012 | Ryu et al. |
| 8,175,703 B2 | 5/2012 | Dong et al. |
| 8,180,428 B2 | 5/2012 | Kaiser et al. |
| 8,195,292 B2 | 6/2012 | Rosenberg et al. |
| 8,213,693 B1 | 7/2012 | Li |
| 8,214,041 B2 | 7/2012 | Van Gelder et al. |
| 8,265,738 B1 | 9/2012 | Min et al. |
| 8,285,377 B2 | 10/2012 | Rosenberg et al. |
| 8,295,943 B2 | 10/2012 | Eggen et al. |
| 8,326,419 B2 | 12/2012 | Rosenberg et al. |
| 8,332,030 B2 | 12/2012 | Hess et al. |
| 8,380,308 B2 | 2/2013 | Rosenberg et al. |
| 8,401,616 B2 | 3/2013 | Verard et al. |
| 8,478,388 B2 | 7/2013 | Nguyen et al. |
| 8,509,896 B2 | 8/2013 | Doerr et al. |
| 8,527,051 B1 | 9/2013 | Hedberg et al. |
| 8,583,230 B2 | 11/2013 | Ryu et al. |

(56) References Cited

U.S. PATENT DOCUMENTS

| | | |
|---|---|---|
| 8,615,298 B2 | 12/2013 | Ghosh et al. |
| 8,617,082 B2 | 12/2013 | Zhang et al. |
| 8,620,433 B2 | 12/2013 | Ghosh et al. |
| 8,639,333 B2 | 1/2014 | Stadler et al. |
| 8,694,099 B2 | 4/2014 | Ghosh et al. |
| 8,738,132 B1 | 5/2014 | Ghosh et al. |
| 8,744,576 B2 | 6/2014 | Munsterman et al. |
| 8,768,465 B2 | 7/2014 | Ghosh et al. |
| 8,805,504 B2 | 8/2014 | Sweeney |
| 8,972,228 B2 | 3/2015 | Ghosh et al. |
| 9,037,238 B2 | 5/2015 | Stadler et al. |
| 9,155,897 B2 | 10/2015 | Ghosh et al. |
| 9,199,087 B2 | 12/2015 | Stadler et al. |
| 9,265,951 B2 | 2/2016 | Sweeney |
| 9,265,954 B2 | 2/2016 | Ghosh |
| 9,265,955 B2 | 2/2016 | Ghosh |
| 9,278,219 B2 | 3/2016 | Ghosh |
| 9,278,220 B2 | 3/2016 | Ghosh |
| 9,282,907 B2 | 3/2016 | Ghosh |
| 9,320,446 B2 | 4/2016 | Gillberg et al. |
| 9,474,457 B2 | 10/2016 | Ghosh et al. |
| 9,486,151 B2 | 11/2016 | Ghosh et al. |
| 9,510,763 B2 | 12/2016 | Gosh et al. |
| 9,586,050 B2 | 3/2017 | Ghosh et al. |
| 9,586,052 B2 | 3/2017 | Gillberg et al. |
| 9,591,982 B2 | 3/2017 | Ghosh et al. |
| 9,764,143 B2 | 9/2017 | Ghosh et al. |
| 9,776,009 B2 | 10/2017 | Ghosh et al. |
| 9,877,789 B2 | 1/2018 | Ghosh et al. |
| 9,924,884 B2 | 3/2018 | Ghosh et al. |
| 10,064,567 B2 | 9/2018 | Ghosh et al. |
| 2002/0072682 A1 | 6/2002 | Hopman et al. |
| 2002/0087089 A1 | 7/2002 | Ben-Haim |
| 2002/0143264 A1 | 10/2002 | Ding et al. |
| 2002/0161307 A1 | 10/2002 | Yu et al. |
| 2002/0169484 A1 | 11/2002 | Mathis et al. |
| 2003/0018277 A1 | 1/2003 | He |
| 2003/0050670 A1 | 3/2003 | Spinelli et al. |
| 2003/0105495 A1 | 6/2003 | Yu et al. |
| 2003/0236466 A1 | 12/2003 | Tarjan et al. |
| 2004/0015081 A1 | 1/2004 | Kramer et al. |
| 2004/0059237 A1 | 3/2004 | Narayan et al. |
| 2004/0097806 A1 | 5/2004 | Hunter et al. |
| 2004/0102812 A1 | 5/2004 | Yonce et al. |
| 2004/0122479 A1 | 6/2004 | Spinelli et al. |
| 2004/0162496 A1 | 8/2004 | Yu et al. |
| 2004/0172078 A1 | 9/2004 | Chinchoy |
| 2004/0172079 A1 | 9/2004 | Chinchoy |
| 2004/0193223 A1 | 9/2004 | Kramer et al. |
| 2004/0215245 A1 | 10/2004 | Stahmann et al. |
| 2004/0215252 A1 | 10/2004 | Verbeek et al. |
| 2004/0220635 A1 | 11/2004 | Burnes |
| 2004/0267321 A1 | 12/2004 | Boileau et al. |
| 2005/0008210 A1 | 1/2005 | Evron et al. |
| 2005/0027320 A1 | 2/2005 | Nehls et al. |
| 2005/0090870 A1 | 4/2005 | Hine et al. |
| 2005/0096522 A1 | 5/2005 | Reddy et al. |
| 2005/0107839 A1 | 5/2005 | Sanders |
| 2005/0149138 A1 | 7/2005 | Min et al. |
| 2006/0074285 A1 | 4/2006 | Zarkh et al. |
| 2006/0224198 A1 | 10/2006 | Dong et al. |
| 2006/0235478 A1 | 10/2006 | Van Gelder et al. |
| 2006/0253162 A1 | 11/2006 | Zhang et al. |
| 2007/0142871 A1 | 6/2007 | Libbus et al. |
| 2007/0167809 A1 | 7/2007 | Dala-Krishna |
| 2007/0232943 A1 | 10/2007 | Harel et al. |
| 2007/0250129 A1 | 10/2007 | Van Oort |
| 2007/0265508 A1 | 11/2007 | Sheikhzadeh-Nadjar et al. |
| 2008/0021336 A1 | 1/2008 | Dobak et al. |
| 2008/0058656 A1 | 3/2008 | Costello et al. |
| 2008/0119903 A1 | 5/2008 | Arcot-Krishnamurthy et al. |
| 2008/0140143 A1 | 6/2008 | Ettori et al. |
| 2008/0146954 A1 | 6/2008 | Bojovic et al. |
| 2008/0242976 A1 | 10/2008 | Robertson et al. |
| 2008/0269818 A1 | 10/2008 | Sullivan et al. |
| 2008/0269823 A1 | 10/2008 | Burnes et al. |
| 2008/0281195 A1 | 11/2008 | Heimdal |
| 2008/0306567 A1 | 12/2008 | Park et al. |
| 2008/0306568 A1 | 12/2008 | Ding et al. |
| 2009/0005832 A1 | 1/2009 | Zhu et al. |
| 2009/0036947 A1 | 2/2009 | Westlund et al. |
| 2009/0043352 A1 | 2/2009 | Brooke et al. |
| 2009/0048528 A1 | 2/2009 | Hopenfeld et al. |
| 2009/0053102 A2 | 2/2009 | Rudy et al. |
| 2009/0054941 A1 | 2/2009 | Eggen et al. |
| 2009/0054946 A1 | 2/2009 | Sommer et al. |
| 2009/0084382 A1 | 4/2009 | Jalde et al. |
| 2009/0093857 A1 | 4/2009 | Markowitz et al. |
| 2009/0099468 A1 | 4/2009 | Thiagalingam et al. |
| 2009/0099469 A1 | 4/2009 | Flores |
| 2009/0099619 A1 | 4/2009 | Lessmeier et al. |
| 2009/0112109 A1 | 4/2009 | Kuklik et al. |
| 2009/0143838 A1 | 6/2009 | Libbus et al. |
| 2009/0157134 A1 | 6/2009 | Ziglio et al. |
| 2009/0157136 A1 | 6/2009 | Yang et al. |
| 2009/0198298 A1 | 8/2009 | Kaiser et al. |
| 2009/0216112 A1 | 8/2009 | Assis et al. |
| 2009/0232448 A1 | 9/2009 | Barmash et al. |
| 2009/0234414 A1 | 9/2009 | Sambelashvili et al. |
| 2009/0254140 A1 | 10/2009 | Rosenberg et al. |
| 2009/0270729 A1 | 10/2009 | Corbucci et al. |
| 2009/0270937 A1 | 10/2009 | Yonce et al. |
| 2009/0299201 A1 | 12/2009 | Gunderson |
| 2009/0299423 A1 | 12/2009 | Min |
| 2009/0306732 A1 | 12/2009 | Rosenberg et al. |
| 2009/0318995 A1 | 12/2009 | Keel et al. |
| 2010/0022873 A1 | 1/2010 | Hunter et al. |
| 2010/0049063 A1 | 2/2010 | Dobak, III |
| 2010/0069987 A1 | 3/2010 | Min et al. |
| 2010/0087888 A1 | 4/2010 | Maskara |
| 2010/0094149 A1 | 4/2010 | Kohut et al. |
| 2010/0113954 A1 | 5/2010 | Zhou |
| 2010/0114229 A1 | 5/2010 | Chinchoy |
| 2010/0121403 A1 | 5/2010 | Schecter et al. |
| 2010/0145405 A1 | 6/2010 | Min et al. |
| 2010/0174137 A1 | 7/2010 | Shim |
| 2010/0198292 A1 | 8/2010 | Honeck et al. |
| 2010/0228138 A1 | 9/2010 | Chen |
| 2010/0234916 A1 | 9/2010 | Turcott et al. |
| 2010/0249622 A1 | 9/2010 | Olson |
| 2010/0254583 A1 | 10/2010 | Chan et al. |
| 2010/0268059 A1 | 10/2010 | Ryu et al. |
| 2011/0004111 A1 | 1/2011 | Gill et al. |
| 2011/0004264 A1 | 1/2011 | Siejko et al. |
| 2011/0022112 A1 | 1/2011 | Min |
| 2011/0054286 A1 | 3/2011 | Crosby |
| 2011/0054559 A1 | 3/2011 | Rosenberg et al. |
| 2011/0054560 A1 | 3/2011 | Rosenberg et al. |
| 2011/0075896 A1 | 3/2011 | Matsumoto |
| 2011/0092809 A1 | 4/2011 | Nguyen et al. |
| 2011/0112398 A1 | 5/2011 | Zarkh et al. |
| 2011/0118803 A1 | 5/2011 | Hou et al. |
| 2011/0137369 A1 | 6/2011 | Ryu et al. |
| 2011/0144510 A1 | 6/2011 | Ryu et al. |
| 2011/0172728 A1 | 7/2011 | Wang |
| 2011/0190615 A1 | 8/2011 | Phillips et al. |
| 2011/0201915 A1 | 8/2011 | Gogin et al. |
| 2011/0213260 A1 | 9/2011 | Keel et al. |
| 2011/0319954 A1 | 12/2011 | Niazi et al. |
| 2012/0004567 A1 | 1/2012 | Eberle et al. |
| 2012/0101543 A1 | 4/2012 | Demmer et al. |
| 2012/0101546 A1 | 4/2012 | Stadler et al. |
| 2012/0203090 A1 | 8/2012 | Min |
| 2012/0253419 A1 | 10/2012 | Rosenberg et al. |
| 2012/0283587 A1 | 11/2012 | Ghosh et al. |
| 2012/0284003 A1 | 11/2012 | Ghosh et al. |
| 2012/0296387 A1 | 11/2012 | Zhang et al. |
| 2012/0296388 A1 | 11/2012 | Zhang et al. |
| 2012/0302904 A1 | 11/2012 | Lian et al. |
| 2012/0303084 A1 | 11/2012 | Kleckner et al. |
| 2012/0310297 A1 | 12/2012 | Sweeney |
| 2012/0330179 A1 | 12/2012 | Yuk et al. |
| 2013/0006332 A1 | 1/2013 | Sommer et al. |
| 2013/0018250 A1 | 1/2013 | Caprio et al. |

(56) References Cited

U.S. PATENT DOCUMENTS

| | | |
|---|---|---|
| 2013/0018251 A1 | 1/2013 | Caprio et al. |
| 2013/0030491 A1 | 1/2013 | Stadler et al. |
| 2013/0060298 A1 | 3/2013 | Splett et al. |
| 2013/0072790 A1 | 3/2013 | Ludwig et al. |
| 2013/0096446 A1 | 4/2013 | Michael et al. |
| 2013/0116739 A1 | 5/2013 | Brada et al. |
| 2013/0131529 A1 | 5/2013 | Jia et al. |
| 2013/0131749 A1 | 5/2013 | Sheldon et al. |
| 2013/0131751 A1 | 5/2013 | Stadler et al. |
| 2013/0136035 A1 | 5/2013 | Bange et al. |
| 2013/0150913 A1 | 6/2013 | Bornzin et al. |
| 2013/0165983 A1 | 6/2013 | Ghosh et al. |
| 2013/0165988 A1 | 6/2013 | Ghosh |
| 2013/0261471 A1 | 10/2013 | Saha et al. |
| 2013/0261688 A1 | 10/2013 | Dong et al. |
| 2013/0289640 A1 | 10/2013 | Zhang et al. |
| 2013/0296726 A1 | 11/2013 | Niebauer et al. |
| 2013/0304407 A1 | 11/2013 | George et al. |
| 2013/0324828 A1 | 12/2013 | Nishiwaki et al. |
| 2014/0005563 A1 | 1/2014 | Ramanathan et al. |
| 2014/0018872 A1 | 1/2014 | Siejko et al. |
| 2014/0135866 A1 | 5/2014 | Ramanathan et al. |
| 2014/0135867 A1 | 5/2014 | Demmer et al. |
| 2014/0163633 A1 | 6/2014 | Ghosh et al. |
| 2014/0222099 A1 | 8/2014 | Sweeney |
| 2014/0236252 A1 | 8/2014 | Ghosh et al. |
| 2014/0276125 A1 | 9/2014 | Hou et al. |
| 2014/0277233 A1 | 9/2014 | Ghosh |
| 2014/0323882 A1 | 10/2014 | Ghosh et al. |
| 2014/0323892 A1 | 10/2014 | Ghosh et al. |
| 2014/0323893 A1 | 10/2014 | Ghosh et al. |
| 2014/0371807 A1 | 12/2014 | Ghosh et al. |
| 2014/0371808 A1 | 12/2014 | Ghosh et al. |
| 2014/0371832 A1 | 12/2014 | Ghosh et al. |
| 2014/0371833 A1 | 12/2014 | Ghosh et al. |
| 2015/0032016 A1 | 1/2015 | Ghosh |
| 2015/0032171 A1 | 1/2015 | Ghosh |
| 2015/0032172 A1 | 1/2015 | Ghosh |
| 2015/0032173 A1 | 1/2015 | Ghosh |
| 2015/0045849 A1 | 2/2015 | Ghosh et al. |
| 2015/0142069 A1 | 5/2015 | Sambelashvili |
| 2015/0157225 A1 | 6/2015 | Gillberg et al. |
| 2015/0157231 A1 | 6/2015 | Gillberg et al. |
| 2015/0157232 A1 | 6/2015 | Gillberg et al. |
| 2015/0157865 A1 | 6/2015 | Gillberg et al. |
| 2015/0216434 A1 | 8/2015 | Ghosh et al. |
| 2015/0265840 A1* | 9/2015 | Ghosh ............... A61N 1/3702 607/27 |
| 2016/0030747 A1 | 2/2016 | Thakur et al. |
| 2016/0030751 A1 | 2/2016 | Ghosh et al. |
| 2016/0045737 A1 | 2/2016 | Ghosh et al. |
| 2016/0045738 A1 | 2/2016 | Ghosh et al. |
| 2016/0045744 A1 | 2/2016 | Gillberg et al. |
| 2016/0184590 A1 | 6/2016 | Ghosh |
| 2017/0246460 A1 | 8/2017 | Ghosh |
| 2017/0246461 A1 | 8/2017 | Ghosh |

FOREIGN PATENT DOCUMENTS

| | | |
|---|---|---|
| CN | 1878595 A | 12/2006 |
| CN | 101073502 A | 11/2007 |
| EP | 1 072 284 A2 | 1/2001 |
| EP | 1 504 713 A1 | 2/2005 |
| EP | 2 016 976 A1 | 1/2009 |
| EP | 2 391 270 A1 | 7/2011 |
| EP | 1 925 337 B1 | 3/2012 |
| EP | 2 436 309 A2 | 4/2012 |
| EP | 2 435 132 B1 | 8/2013 |
| WO | WO 1998/026712 A1 | 6/1998 |
| WO | WO 1999/006112 A1 | 2/1999 |
| WO | WO 2000/045700 A1 | 8/2000 |
| WO | WO 2001/067950 A1 | 9/2001 |
| WO | WO 2003/070323 A1 | 8/2003 |
| WO | WO 2005/056108 A2 | 6/2005 |
| WO | WO 2006/069215 A2 | 6/2006 |
| WO | WO 2006/069215 A3 | 6/2006 |
| WO | WO 2006/105474 A2 | 10/2006 |
| WO | WO 2006/115777 A1 | 11/2006 |
| WO | WO 2006/117773 A1 | 11/2006 |
| WO | WO 2007/013994 A2 | 2/2007 |
| WO | WO 2007/027940 A2 | 3/2007 |
| WO | WO 2007/013994 A3 | 4/2007 |
| WO | WO 2007/027940 A3 | 6/2007 |
| WO | WO 2007/139456 A1 | 12/2007 |
| WO | WO 2008/151077 A2 | 12/2008 |
| WO | WO 2009/079344 A1 | 6/2009 |
| WO | WO 2009/139911 A2 | 11/2009 |
| WO | WO 2009/148429 A1 | 12/2009 |
| WO | WO 2010/019494 A1 | 2/2010 |
| WO | WO 2010/071520 A1 | 6/2010 |
| WO | WO 2010/088040 A1 | 8/2010 |
| WO | WO 2010/088485 A1 | 8/2010 |
| WO | WO 2011/070166 A1 | 6/2011 |
| WO | WO 2011/090622 A1 | 7/2011 |
| WO | WO 2011/099992 A1 | 8/2011 |
| WO | WO 2012/037471 A2 | 3/2012 |
| WO | WO 2012/037471 A3 | 6/2012 |
| WO | WO 2012/106297 A2 | 8/2012 |
| WO | WO 2012/106297 A3 | 8/2012 |
| WO | WO 2012/109618 A2 | 8/2012 |
| WO | WO 2012/110940 A1 | 8/2012 |
| WO | WO 2012/109618 A3 | 11/2012 |
| WO | WO 2012/151364 A1 | 11/2012 |
| WO | WO 2012/151389 A1 | 11/2012 |
| WO | WO 2013/006724 A2 | 1/2013 |
| WO | WO 2013/010165 A1 | 1/2013 |
| WO | WO 2013/010184 A1 | 1/2013 |
| WO | WO 2013/006724 A3 | 4/2013 |
| WO | WO 2014/179454 A1 | 11/2014 |
| WO | WO 2014/179459 A2 | 11/2014 |
| WO | WO 2014/179459 A3 | 1/2015 |
| WO | WO 2015/013271 A1 | 1/2015 |
| WO | WO 2015/013493 A1 | 1/2015 |
| WO | WO 2015/013574 A1 | 1/2015 |

OTHER PUBLICATIONS

International Search Report and Written Opinion dated May 3, 2012 for International Application No. PCT/US2012/036302; 9 pages.
International Search Report and Written Opinion dated Aug. 6, 2014 for International Application No. PCT/US2014/036153; 14 pages.
International Search Report and Written Opinion dated Nov. 7, 2014 for International Application No. PCT/US2014/036163; 12 pages.
International Search Report and Written Opinion dated Oct. 28, 2014 for International Application No. PCT/US2014/041928; 15 pages.
International Search Report and Written Opinion dated Oct. 24, 2014 for International Application No. PCT/US2014/041929; 14 pages.
International Search Report and Written Opinion dated Nov. 4, 2014 for International Application No. PCT/US2014/0247583; 7 pages.
International Search Report and Written Opinion dated Nov. 12, 2014 for International Application No. PCT/US2014/047971; 7 pages.
International Search Report and Written Opinion dated Nov. 12, 2014 for International Application No. PCT/US2014/048120; 7 pages.
International Search Report and Written Opinion dated Mar. 9, 2015 for International Application No. PCT/US2014/069214; 11 pages.
International Search Report and Written Opinion dated Mar. 17, 2015, for International Application No. PCT/US2014/069192; 11 pages.
International Search Report and Written Opinion dated Mar. 16, 2015 for International Application No. PCT/US2014/069182; 11 pages.
International Search Report and Written Opinion dated Apr. 8, 2015 for International Application No. PCT/US2014/069070; 11 pages.
International Search Report and Written Opinion dated Jun. 11, 2015 for International Application No. PCT/US2015/021442; 13 pages.

(56) References Cited

OTHER PUBLICATIONS

Bank, "Changes in electrical heterogeneity of body surface maps: Application for CRT optimization" Poster Presentation. HRS 2016 Annual Meeting. May 4-7; San Francisco, California.

Bank, "Electrical dyssynchrony and optimization potential with and without Class I Indications for Cardiac Resynchronization Therapy" Cardiostim 2016 World Congress in Cardiac Electrophysiology and Cardiac Techniques. Jun. 8-11. Nice, France. Jun. 2016 Europace 18(suppl_1):i50-i50.

Bank, "Electrical heterogeneity varies using different pacing electrodes of left ventricular quadripolar leads" Poster Presentation. HRS 2016 Annual Meeting. May 4-7; San Francisco, California.

Bank, "Optimization of VV timing in CRT using body surface maping: Role of LV preactivation" Oral Presentation. HRS 2017 Annual Meeting. May 10-13; Chicago, Illinois.

Bank, "Use of a novel noninvasive ECG mapping system to identify line of block and optimal CRT seBank-use-10tting" Poster Presentation. Cardiostim 2016 World Congress in Cardiac Electrophysiology and Cardiac Techniques. Jun. 8-11. Nice, France.

Biffi et al., "Occurrence of Phrenic Nerve Stimulation in Cardiac Resynchronization Therapy Patients: the Role of Left Ventricular Lead Type and Placement Site," *Europace*, 2013; 15:77-82.

Botker MD, PhD., et al., "Electromechanical Mapping for Detection of Myocardial Viability in Patients with ischemia Cardiomyopathy," Circulation, Mar. 2001; vol. 103, No. 12, pp.

Burns, "Left ventricular-only pacing in heart failure patients with normal atrioventricular conduction improves global function and left ventricular regional mechanics compared with biventricular pacing: an adaptive cardiac resynchronization therapy sub-study" Oct. 2017 *Eur J Heart Fail.*, 19(10):1335-1343.

"CardioGuide System Enables Real-Time Navigation of Left Ventricular Leads During Medtronic CRT Implants," Press Release, Apr. 9, 2013, Medtronic, Inc., 2 pgs.

Cuculich, P.S., et al., "The Electrophysiological Cardiac Ventricular Substrate in Patients After Myocardial Infection" J. Am. Coll. Cardiol. 2011; 58:1893-1902.

Curtin, "Description of body surface activation map patterns in patients grouped by 12-lead ECG morphology" HRS 2017 Annual Meeting. May 10-13; Chicago, Illinois.

Curtin, "Electrical heterogeneity metrics from body surface mapping vs routine ECG measures before and after CRT" Poster Presentation. HRS 2016 Annual Meeting. May 4-7; San Francisco, California.

Curtin, "Left ventricular orientation and position in an advanced heart failure population" Jun. 2017 *Translational Research in Anatomy*, 7:12-19.

Curtin, "Use of body surface mapping to assess wavefront fusion in CRT" Poster Presentation. HRS 2016 Annual Meeting. May 4-7; San Francisco, California.

Czerwinska et al., "Method of Segmentation of Thorax Organs Images Applied to Modeling the Cardiac Electrical Field," *Engineering in Medicine and Biology Society*, Proceedings of the 22$^{nd}$ Annual International Conference of the IEEE, vol. 1, 23, Jul. 23, 2000.; pp. 402-405.

Dawoud, F. et al., "Inverse Electrocardiographic Imaging to Assess Electrical Dyssynchrony in Cardiac Resynchronization Therapy Patients," Computing in Cardiology, 2012; 39:993-996.

Freund et al., "A Decision-Theoretic Generalization of Online Learning and an Application to Boosting," *Journal of Computer and System Sciences*, 1997; 55(1):119-139.

Friedman, "Greedy Function Approximation: A Gradient Boosting Machine," *Annals of Statistics*, 2001; 29(5):1189-1232.

Friedman, "Stochastic Gradient Boosting," *Computational Statistics and Data Analysis*, 2002; 38(4):367-378.

Friedman et al., "Additive Logistic Regression: a Statistical View of Boosting," *Annals of Statistics*, 2000; 28(2):337-374.

Fung et al., Chapter 20, Optimization of Cardiac Resynchronization Therapy, Cardiac Resynchronization Therapy, Second Edition, Copyright 2008, Blackwell Publishing Ltd., pp. 356-373.

Gage, "Changes in electrical dyssynchrony by body surface mapping predict LV remodelling in CRT patients" 2016 HeartRhythm, 14(3):392-399.

Gage, "Changes in electrical heterogeneity of body surface mapping predict LV remodeling in CRT patients" Poster Presentation. HRS 2016 Annual Meeting. May 4-7; San Francisco, California.

Ghosh et al. "Accuracy of Quadratic Versus Linear Interpolation in Noninvasive Electrocardiographic Imaging (ECGI)," *Annuals of Biomedical Engineering*, vol. 33, No. 9. Sep. 2005; pp. 1187-1201.

Ghosh et al., "Cardiac Memory in Patents with Wolff-Parkinson-White Syndrome: Noninvasive Imaging of Activation and Repolarization Before and After Catheter Ablation" *Circulation*, 2008; 118:907-915. Published online Aug. 12, 2008.

Ghosh et al. "Application of L1-Norm Regularization to Epicardial Potential Solution of the Inverse Electrocardiography Problem," *Annuals of Biomedical Engineering*, vol. 37, No. 5, May 2009; pp. 902-912.

Ghosh et al., "Electrophysiological Substrate and Intraventricular LV Dyssynchrony in Non-ischemic Heart Failure Patients Undergoing Cardiac Resynchronization Therapy," *Heart rhythm : the official journal of the Heart Rhythm Society*, 2011; 8(5):692-699.

Gold et al., "Comparison of Stimulation Sites within Left Ventricular Veins on the Acute Hemodynamic Effects of Cardiac Resynchronization Therapy" *Heart Rhythm*, Apr. 2005; 2(4):376-381.

Gulrajani, "The Forward and Inverse Problems of Electrocardiography," *IEEE Engineering in Medicine and Biology*, IEEE Service Center, vol. 17, No. 5, Sep. 1, 1988; pp. 84-101, 122.

Hansen, "Regularization Tools: A Matlab Package for Analysis and Solution of Discrete Ill-Posed Problems," Version 4.1 for Matlab 7.3; Mar. 2008; 128 pages. Retrieved from the Internet: Jun. 19, 2014 http://www.mathworks.com/matlabcentral/fileexchange/52-regtools.

Hayes et al., "Cardiac Resynchronization Therapy and the Relationship of Percent Biventricular Pacing to Symptoms and Survival," *Heart Rhythm*, Sep. 2011; 8(9):1469-1475.

"Heart Failure Management" datasheet [online]. Medtronic, Minneapolis, Minnesota, [Last updated on Jun. 3, 2013].Retrieved from the Internet: www.medtronic.com; 9 pages.

Hopenfeld et al., "The Effect of Conductivity on ST-Segment Epicardial Potentials Arising from Subendocardial Ischemia," Annals of Biomedical Eng., Jun. 2005; vol. 33, No. 6, pp. 751-763.

Jia et al., "Electrocardiographic Imaging of Cardiac Resynchronization Therapy in Heart Failure: Observation of Variable Electrophysiologic Responses," *Heart Rhythm*, vol. 3, No. 3; Mar. 1, 2006, pp. 296-310.

Johnson, "Body surface mapping using an ECG belt to characterize electrical heterogeneity for different left ventricular pacing sites during cardiac resynchronization: Relationship with acute hemodynamic improvement" Mar. 2017 Heart Rhythm, 14(3):385-391.

Kornreich, "Body Surface Potential Mapping of ST Segment Changes in Acute Myocardial Infarction," *Circulation*, 1993; 87: 773-782.

Lumason™, Brochure, Bracco Diagnostocs. Oct. 2014.

Medtronic Vitatron CARELINK ENCORE® Programmer Model 29901 Reference Manual, 2013, Medtronic, Inc., Minneapolis, MN.

Miri et al., "Applicability of body surface potential map in computerized optimization of biventricular pacing," Annals of Biomedical Engineering, vol. 38, No. 3, Mar. 2010, pp. 865-875.

Miri et al., "Comparison of the electrophysiologically based optimization methods with different pacing parameters in patient undergoing resynchronization treatment," 30th Annual International IEEE EMBS Conference, Aug. 2008, pp. 1741-1744.

Miri et al., "Computerized Optimization of Biventricular Pacing Using Body Surface Potential Map," 31st Annual International Conference of the IEEE EMBS, Sep. 2009, pp. 2815-2818.

Miri et al., "Efficiency of Timing Delays and Electrode Positions in Optimization of Biventricular Pacing: A Simulation Study," IEEE Transactions on Biomedical Engineering, Nov. 2009, pp. 2573-2582.

Modre et al., "Noninvasive Myocardial Activation Time Imaging: A Novel Inverse Algorithm Applied to Clinical ECG Mapping Data" *IEEE Transactions on Biomedical Engineering*, vol. 49; No. 10, Oct. 2002; pp. 1153-1161.

(56) References Cited

OTHER PUBLICATIONS

Nash et al., "An Experimental-Computational Framework for Validating in-vivo ECG Inverse Algorithms," International Journal of Bioelectromagnetism, vol. 2, No. 2, Dec. 31, 2000, 9 pp.
Potse et al., "Mathematical Modeling and Simulation of Ventricular Activation Sequences: Implications for Cardiac Resynchronization Therapy," *J. of Cardiovasc. Trans. Res.*, 2012; 5:146-158.
Prinzen et al., "Cardiac Resynchronization Therapy State-of-the-Art of Current Applications, Guidelines, Ongoing Trials, and Areas of Controversy" *Circulation*, 2013; 128: 2407-2418.
Ridgeway, "The State of Boosting," *Computing Science and Statistics*, 1999; 31:172-181.
Ryu et al., "Simultaneous Electrical and Mechanical Mapping Using 3D Cardiac Mapping System: Novel Approach for Optimal Cardiac Resynchronization Therapy," *Journal of Cardiovascular Electrophysiology*, Feb. 2010; 21(2):219-22.
Silva et al., "Cardiac Resynchronization Therapy in Pediatric Congenital Heart Disease: Insights from Noninvasive Electrocardiographic Imaging" *Heart Rhythm*, vol. 6, No. 8. Aug. 1, 2009; pp. 1178-1185.
Singh et al., "Left Ventricular Lead Position and Clinical Outcome in the Multicenter Automatic Defibrillator Implantation Trial-Cardiac Resynchronization Therapy (MADIT-CRT) Trial," *Circulation*, 2011; 123:1159-1166.
Sperzel et al., "Intraoperative Characterization of Interventricular Mechanical Dyssynchrony Using Electroanatomic Mapping System—A Feasibility Study," *Journal of Interventional Cardiac Electrophysiology*, Nov. 2012; 35(2):189-96.
Steinhaus BM., "Estimating cardiac transmembrane activation and recovery times from unipolar and bipolar extracellular electrograms: a simulation study," Circulation Research, 1989, 64:449-462.
Strik et al., "Electrical and Mechanical Ventricular Activation During Left Bundle Branch Block and Resynchronization," *J. of Cardiovasc. Trans. Res.*, 2012; 5:117-126.
Svendsen et al., "Computational Models of Cardiac Electrical Activation," Chapter 5, Computational Nov. 2010, pp. 73-88.
Sweeney et al., "Analysis of Ventricular Activation Using Surface Electrocardiography to Predict Left Ventricular Reverse Volumetric Remodeling During Cardiac Resynchronization Therapy," *Circulation*, Feb. 9, 2010; 121(5):626-34. Available online Jan. 25, 2010.
Sweeney et al., QRS Fusion Complex Analysis Using Wave Interference to Predict Reverse Remodeling During Cardiac Resynchronization Therapy, heart Rhythm, 2014, 11:806-813.
Turner et al, "Electrical and Mechanical Components of Dyssynchrony in Heart Failure Patients with Normal QRS Duration and Left Bundle-Branch Block," *Circulation* 2004; 109: 2544-2549.
Van Deursen et al., "Vectorcardiography as a Tool for Easy Optimization of Cardiac Resynchronization Therapy in Canine LBBB Hearts," *Circulation Arrhythmia and Electrophysiology*, Jun. 1, 2012; 5(3):544-52. Available online Apr. 24, 2012.
Vardas et al., The Task Force for Cardiac Pacing and Cardiac Resynchronization Therapy of the European Society of Cardiology. Developed in Collaboration with the European Heart Rhythm Association, *European Heart Journal*, 2007; 28:2256-2295.
Varma et al., "Placebo CRT," *Journal of Cardiovascular Electrophysiology*, vol. 19, Aug. 2008; p. 878.
Wang et al., "Application of the Method of Fundamental Solutions to Potential-based Inverse Electrocardiography," Annals of Biomedical Engineering, Aug. 2006, pp. 1272-1288.
Wellens, MD et al., "The Electrocardiogram 102 Years After Einthoven," Circulation, Feb. 2004; vol. 109, No. 5, pp. 562-564.
Williams et al., "Short-Term Hemodynamic Effects of Cardiac Resynchronization Therapy in Patients With Heart Failure, a Narrow QRS Duration, and No Dyssynchrony," *Circulation*, Oct. 27, 2009; 120: 1687-1694.

\* cited by examiner

ANTERIOR AND POSTERIOR ELECTRODE SIGNALS

This application claims the benefit of U.S. Provisional Patent Application Ser. No. 62/609,935 filed Dec. 22, 2017, entitled "Anterior and Posterior Electrode Signals," which is incorporated by reference herein in its entirety.

The disclosure herein relates to systems, methods, and interfaces for use in the analysis and processing of anterior and posterior electrode signals.

SUMMARY

The exemplary systems, methods, and interfaces described herein may be configured to assist a user (e.g., a physician) in evaluating a patient and/or evaluating cardiac therapy (e.g., cardiac therapy being performed on a patient during and/or after implantation of cardiac therapy apparatus). In one or more embodiments, the systems, methods, and interfaces may be described as being noninvasive. For example, in some embodiments, the systems, methods, and interfaces may not need, or include, implantable devices such as leads, probes, sensors, catheters, implantable electrodes, etc. to monitor, or acquire, a plurality of cardiac signals from tissue of the patient for use in evaluating the patient and/or cardiac therapy being delivered to the patient. Instead, the systems, methods, and interfaces may use electrical measurements taken noninvasively using, e.g., a plurality of external electrodes attached to the skin of a patient about the patient's torso.

One exemplary system for use in cardiac evaluation may include electrode apparatus comprising a plurality of external electrodes to be located proximate a patient's skin. The plurality of external electrodes may include a posterior set of electrodes located proximate the patient's posterior and an anterior set of electrodes located proximate the patient's anterior. The computing apparatus may include processing circuitry and may be operably coupled to the electrode apparatus. The computing apparatus may be configured to monitor electrical activity from the patient's skin using the plurality of external electrodes over a cardiac cycle resulting in a posterior set of electrode signals monitored from one or more of the posterior set of electrodes and an anterior set of electrode signals monitored from one or more of the anterior set of electrodes and compare the morphology of the anterior set of electrode signals and the morphology of the posterior set of electrode signals to assist in determination of electrical heterogeneity.

One exemplary method for use in cardiac evaluation may include monitoring electrical activity from a patient's skin using a plurality of external electrodes over a cardiac cycle resulting in a posterior set of electrode signals monitored from one or more of posterior set of electrodes located proximate the patient's posterior and an anterior set of electrode signals monitored from one or more of an anterior set of electrodes located proximate the patient's anterior and comparing the morphology of the anterior set of electrode signals and the morphology of the posterior set of electrode signals to assist in determination of electrical heterogeneity.

The above summary is not intended to describe each embodiment or every implementation of the present disclosure. A more complete understanding will become apparent and appreciated by referring to the following detailed description and claims taken in conjunction with the accompanying drawings.

DETAILED DESCRIPTION OF EXEMPLARY EMBODIMENTS

Figure 1:
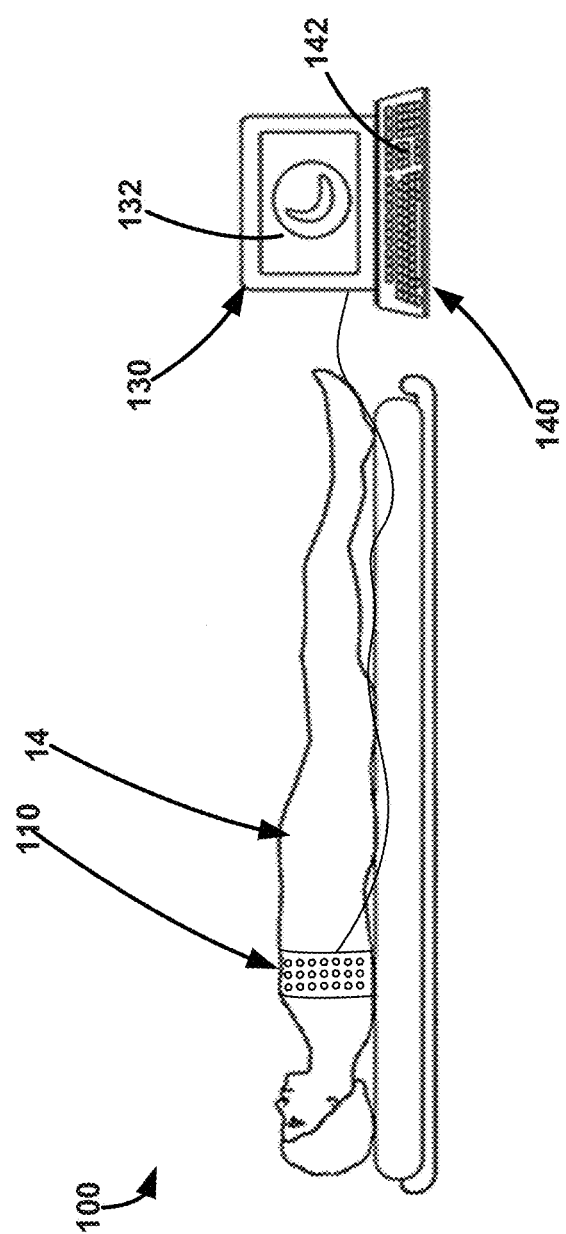
FIG. 1 is a diagram of an exemplary system including electrode apparatus, display apparatus, and computing apparatus.

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary systems, methods, and interfaces shall be described with reference to FIGS. 1-11. It will be apparent to one skilled in the art that elements or processes from one embodiment may be used in combination with elements or processes of the other embodiments, and that the possible embodiments of such methods and systems using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

Cardiac electrical activation times can be detected or estimated in proximity of a reference location (e.g., which can be a chosen location for the left ventricle lead during implant) using unipolar electrocardiogram (ECG) recordings. Such electrical activation times may be measured and displayed, or conveyed, to an implanter by a system which acquires the ECG signals and generates the metric of electrical activation times (e.g., depolarization) measured from various ECG locations.

Various exemplary systems, methods, and interfaces may be configured to use electrode apparatus including external electrodes, display apparatus, and computing apparatus to noninvasively assist a user (e.g., a physician) in the evaluation of a patient's cardiac condition and/or cardiac therapy being performed on a patient. An exemplary system 100 including electrode apparatus 110, display apparatus 130, and computing apparatus 140 is depicted in FIG. 1.

The electrode apparatus 110 as shown includes a plurality of electrodes incorporated, or included, within a band wrapped around the chest, or torso, of a patient 14. The electrode apparatus 110 is operatively coupled to the computing apparatus 140 (e.g., through one or wired electrical connections, wirelessly, etc.) to provide electrical signals (e.g., body-surface potentials) from each of the electrodes to the computing apparatus 140 for analysis, evaluation, etc. Exemplary electrode apparatus may be described in U.S. Pat. No. 9,320,446 entitled "Bioelectric Sensor Device and Methods" and issued on Apr. 26, 2016, which is incorporated herein by reference in its entirety. Further, exemplary electrode apparatus 110 will be described in more detail in reference to FIGS. 2-3.

Although not described herein, the exemplary system 100 may further include imaging apparatus. The imaging apparatus may be any type of imaging apparatus configured to image, or provide images of, at least a portion of the patient in a noninvasive manner. For example, the imaging apparatus may not use any components or parts that may be located within the patient to provide images of the patient except noninvasive tools such as contrast solution. It is to be understood that the exemplary systems, methods, and interfaces described herein may further use imaging apparatus to provide noninvasive assistance to a user (e.g., a physician) to locate or select a pacing electrode or pacing vector proximate the patient's heart in conjunction with the evaluation of cardiac therapy.

For example, the exemplary systems, methods, and interfaces may provide image-guided navigation that may be used to navigate leads including electrodes, leadless electrodes, wireless electrodes, catheters, etc., within the patient's body while also providing noninvasive cardiac therapy evaluation including determining location information (e.g., location information for the electrodes). Exemplary systems and methods that use imaging apparatus and/or electrode apparatus may be described in U.S. Pat. No. 9,877,789 issued Jan. 30, 2018, and entitled "Implantable Electrode Location Selection," U.S. Patent Application Pub. No. US 2014/0371833 A1 published Dec. 18, 2014, and entitled "Implantable Electrode Location Selection," U.S. Pat. No. 9,924,884 issued Mar. 27, 2018, and entitled "Systems, Methods, and Interfaces for Identifying Effective Electrodes," U.S. Pat. No. 10,064,567 issued Sep. 4, 2018, and entitled "Systems, Methods, and Interfaces for Identifying Optical Electrical Vectors," each of which is incorporated herein by reference in its entirety.

Exemplary imaging apparatus may be configured to capture x-ray images and/or any other alternative imaging modality. For example, the imaging apparatus may be configured to capture images, or image data, using isocentric fluoroscopy, bi-plane fluoroscopy, ultrasound, computed tomography (CT), multi-slice computed tomography (MSCT), magnetic resonance imaging (MRI), high frequency ultrasound (HIFU), optical coherence tomography (OCT), intra-vascular ultrasound (IVUS), two dimensional (2D) ultrasound, three dimensional (3D) ultrasound, four dimensional (4D) ultrasound, intraoperative CT, intraoperative MIII, etc. Further, it is to be understood that the imaging apparatus may be configured to capture a plurality of consecutive images (e.g., continuously) to provide video frame data. In other words, a plurality of images taken over time using the imaging apparatus may provide video frame, or motion picture, data. Additionally, the images may also be obtained and displayed in two, three, or four dimensions. In more advanced forms, four-dimensional surface rendering of the heart or other regions of the body may also be achieved by incorporating heart data or other soft tissue data from a map or from pre-operative image data captured by MRI, CT, or echocardiography modalities. Image datasets from hybrid modalities, such as positron emission tomography (PET) combined with CT, or single photon emission computer tomography (SPECT) combined with CT, could also provide functional image data superimposed onto anatomical data, e.g., to be used to navigate treatment apparatus proximate target locations within the heart or other areas of interest.

Systems and/or imaging apparatus that may be used in conjunction with the exemplary systems and method described herein are described in U.S. Pat. App. Pub. No. 2005/0008210 to Evron et al. published on Jan. 13, 2005, U.S. Pat. App. Pub. No. 2006/0074285 to Zarkh et al. published on Apr. 6, 2006, U.S. Pat. No. 8,731,642 issued May 20, 2014, to Zarkh et al. U.S. Pat. No. 8,861,830 issued Oct. 14, 2014, to Brada et al. U.S. Pat. No. 6,980,675 to Evron et al. issued on Dec. 27, 2005, U.S. Pat. No. 7,286,866 to Okerlund et al. issued on Oct. 23, 2007, U.S. Pat. No. 7,308,297 to Reddy et al. issued on Dec. 11, 2011, U.S. Pat. No. 7,308,299 to Burrell et al. issued on Dec. 11, 2011, U.S. Pat. No. 7,321,677 to Evron et al. issued on Jan. 22, 2008, U.S. Pat. No. 7,346,381 to Okerlund et al. issued on Mar. 18, 2008, U.S. Pat. No. 7,454,248 to Burrell et al. issued on Nov. 18, 2008, U.S. Pat. No. 7,499,743 to Vass et al. issued on Mar. 3, 2009, U.S. Pat. No. 7,565,190 to Okerlund et al. issued on Jul. 21, 2009, U.S. Pat. No. 7,587,074 to Zarkh et al. issued on Sep. 8, 2009, U.S. Pat. No. 7,599,730 to Hunter et al. issued on Oct. 6, 2009, U.S. Pat. No. 7,613,500 to Vass et al. issued on Nov. 3, 2009, U.S. Pat. No. 7,742,629 to Zarkh et al. issued on Jun. 22, 2010, U.S. Pat. No. 7,747,047 to Okerlund et al. issued on Jun. 29, 2010, U.S. Pat. No. 7,778,685 to Evron et al. issued on Aug. 17, 2010, U.S. Pat. No. 7,778,686 to Vass et al. issued on Aug. 17, 2010, U.S. Pat. No. 7,813,785 to Okerlund et al. issued on Oct. 12, 2010, U.S. Pat. No. 7,996,063 to Vass et al. issued on Aug. 9, 2011, U.S. Pat. No. 8,060,185 to Hunter et al. issued on Nov. 15, 2011, and U.S. Pat. No. 8,401,616 to Verard et al. issued on Mar. 19, 2013, each of which is incorporated herein by reference in its entirety.

The display apparatus 130 and the computing apparatus 140 may be configured to display and analyze data such as, e.g., electrical signals (e.g., electrocardiogram data), cardiac information representative of at least one of mechanical cardiac functionality and electrical cardiac functionality, etc. Cardiac information may include, e.g., electrical heterogeneity information or electrical dyssynchrony information, body surface cardiac activation information, surrogate cardiac electrical activation information or data, etc. that is generated using electrical signals (e.g., body-surface potentials) gathered, monitored, or collected, using the electrode apparatus 110. In at least one embodiment, the computing apparatus 140 may be a server, a personal computer, or a tablet computer. The computing apparatus 140 may be configured to receive input from input apparatus 142 and transmit output to the display apparatus 130. Further, the computing apparatus 140 may include data storage that may allow for access to processing programs or routines and/or one or more other types of data, e.g., for driving a graphical user interface configured to noninvasively assist a user in evaluating, selecting, and/or determining cardiac therapy settings (e.g., the location of an implantable electrode used for pacing, the location of pacing therapy delivered by a particular pacing vector, type of pacing therapy such as biventricular pacing, and left ventricular-only pacing, and various timings of pacing therapy such as atrioventricular (AV) delay, interventricular (VV) delay, pulse width, and/or voltage).

The computing apparatus 140 may be operatively coupled to the input apparatus 142 and the display apparatus 130 to, e.g., transmit data to and from each of the input apparatus 142 and the display apparatus 130. For example, the computing apparatus 140 may be electrically coupled to each of the input apparatus 142 and the display apparatus 130 using, e.g., analog electrical connections, digital electrical connections, wireless connections, bus-based connections, network-based connections, internet-based connections, etc. As described further herein, a user may provide input to the input apparatus 142 to manipulate, or modify, one or more graphical depictions displayed on the display apparatus 130 and to view and/or select one or more pieces of information related to the cardiac therapy.

Although as depicted the input apparatus 142 is a keyboard, it is to be understood that the input apparatus 142 may include any apparatus capable of providing input to the computing apparatus 140 to perform the functionality, methods, and/or logic described herein. For example, the input apparatus 142 may include a mouse, a trackball, a touchscreen (e.g., capacitive touchscreen, a resistive touchscreen, a multi-touch touchscreen, etc.), etc. Likewise, the display apparatus 130 may include any apparatus capable of displaying information to a user, such as a graphical user interface 132 including cardiac information, textual instructions, graphical depictions of electrical activation information, graphical depictions of a plurality of signals including anterior and posterior electrode signals, graphical depictions of anatomy of a human heart, images or graphical depictions of the patient's heart, graphical depictions of locations of one or more electrodes, graphical depictions of a human torso, images or graphical depictions of the patient's torso, graphical depictions or actual images of implanted electrodes and/or leads, etc. Further, the display apparatus 130 may include a liquid crystal display, an organic light-emitting diode screen, a touchscreen, a cathode ray tube display, etc.

The processing programs or routines stored and/or executed by the computing apparatus 140 may include programs or routines for computational mathematics, matrix mathematics, dispersion determinations (e.g. standard deviations, distances, areas under the curve, variances, ranges, interquartile ranges, mean absolute differences, average absolute deviations, etc.), filtering algorithms, maximum value determinations, minimum value determinations, threshold determinations, moving windowing algorithms, decomposition algorithms, compression algorithms (e.g., data compression algorithms), calibration algorithms, image construction algorithms, signal processing algorithms (e.g., various filtering algorithms, Fourier transforms, fast Fourier transforms, etc.), standardization algorithms, comparison algorithms, vector mathematics, or any other processing required to implement one or more exemplary methods and/or processes described herein. Data stored and/or used by the computing apparatus 140 may include, for example, electrical signal/waveform data from the electrode apparatus 110 (such as, e.g., anterior and posterior electrode signals over a plurality of cardiac cycles, over a single cardiac cycles, over various slices of time, etc.), parts or portions of various signals, electrical activation times from the electrode apparatus 110, graphics (e.g., graphical elements, icons, buttons, windows, dialogs, pull-down menus, graphic areas, graphic regions, 3D graphics, etc.), graphical user interfaces, results from one or more processing programs or routines employed according to the disclosure herein (e.g., electrical signals, cardiac information, etc.), or any other data that may be necessary for carrying out the one and/or more processes or methods described herein.

In one or more embodiments, the exemplary systems, methods, and interfaces may be implemented using one or more computer programs executed on programmable computers, such as computers that include, for example, processing capabilities, data storage (e.g., volatile or non-volatile memory and/or storage elements), input devices, and output devices. Program code and/or logic described herein may be applied to input data to perform functionality described herein and generate desired output information. The output information may be applied as input to one or more other devices and/or methods as described herein or as would be applied in a known fashion.

The one or more programs used to implement the systems, methods, and/or interfaces described herein may be provided using any programmable language, e.g., a high-level procedural and/or object orientated programming language that is suitable for communicating with a computer system. Any such programs may, for example, be stored on any suitable device, e.g., a storage media, that is readable by a general or special purpose program running on a computer system (e.g., including processing apparatus) for configuring and operating the computer system when the suitable device is read for performing the procedures described herein. In other words, at least in one embodiment, the exemplary systems, methods, and/or interfaces may be implemented using a computer readable storage medium, configured with a computer program, where the storage medium so configured causes the computer to operate in a specific and predefined manner to perform functions described herein. Further, in at least one embodiment, the exemplary systems, methods, and/or interfaces may be described as being implemented by logic (e.g., object code) encoded in one or more non-transitory media that includes code for execution and, when executed by a processor, is operable to perform operations such as the methods, processes, and/or functionality described herein.

The computing apparatus 140 may be, for example, any fixed or mobile computer system (e.g., a controller, a microcontroller, a personal computer, minicomputer, tablet computer, etc.) and may be generally described as including processing circuitry. The exact configuration of the computing apparatus 140 is not limiting, and essentially any device capable of providing suitable computing capabilities and control capabilities (e.g., graphics processing, etc.) may be used. As described herein, a digital file may be any medium (e.g., volatile or non-volatile memory, a CD-ROM, a punch card, magnetic recordable medium such as a disk or tape, etc.) containing digital bits (e.g., encoded in binary, trinary, etc.) that may be readable and/or writeable by computing apparatus 140 described herein. Also, as described herein, a file in user-readable format may be any representation of data (e.g., ASCII text, binary numbers, hexadecimal numbers, decimal numbers, graphically, etc.) presentable on any medium (e.g., paper, a display, etc.) readable and/or understandable by a user.

In view of the above, it will be readily apparent that the functionality as described in one or more embodiments according to the present disclosure may be implemented in any manner as would be known to one skilled in the art. As such, the computer language, the computer system, or any other software/hardware which is to be used to implement the processes described herein shall not be limiting on the scope of the systems, processes or programs (e.g., the functionality provided by such systems, processes or programs) described herein.

Figure 2:
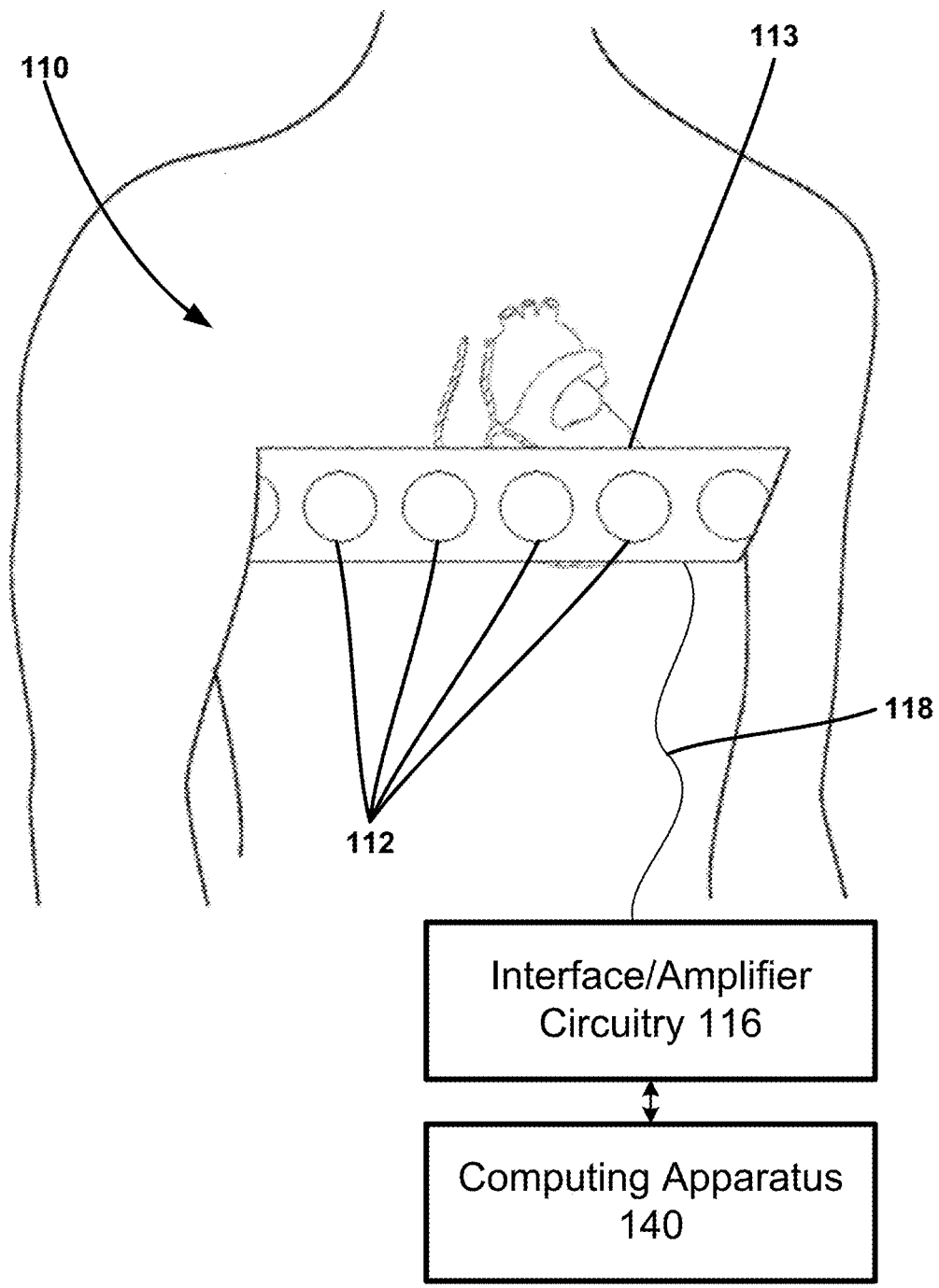
FIGS. 2-3 are diagrams of exemplary external electrode apparatus for measuring torso-surface potentials.
Figure 3:
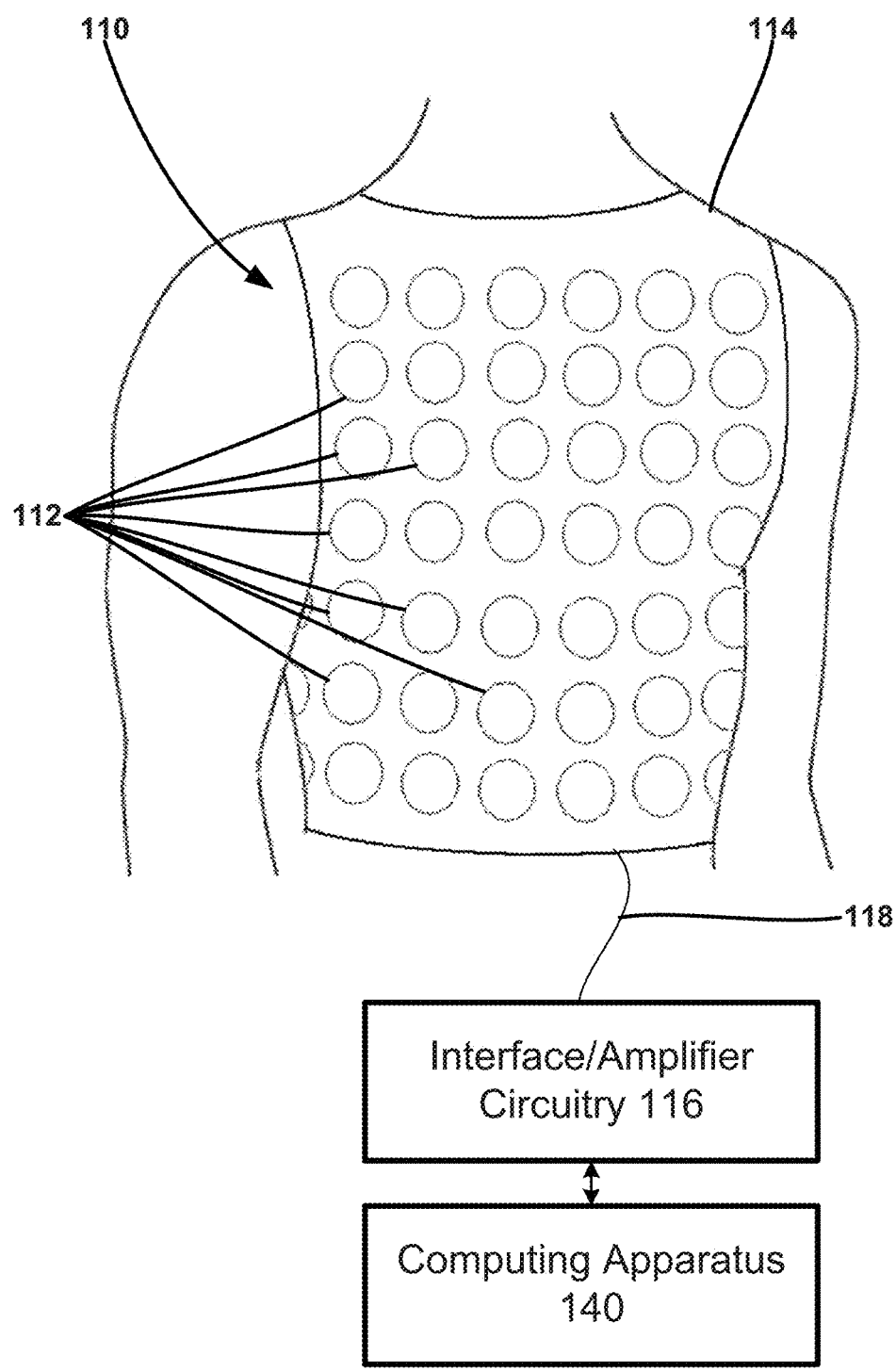

Electrical signal activity of the patient's heart monitored using electrode apparatus 110 as shown in FIG. 3 may be useful to evaluate a patient's cardiac condition and/or cardiac therapy being delivered to a patient. The exemplary electrode apparatus 110 may be configured to measure electrical activity (e.g., body-surface potentials) of a patient 14 and, more particularly, electrical activity (e.g., torso-surface potentials) of a patient 14. As shown in FIG. 2, the exemplary electrode apparatus 110 may include a set, or array, of electrodes 112, a strap 113, and interface/amplifier circuitry 116. The electrodes 112 may be attached, or coupled, to the strap 113 and the strap 113 may be configured to be wrapped around the torso of a patient 14 such that the electrodes 112 surround the patient's heart. As further illustrated, the electrodes 112 may be positioned around the circumference of a patient 14, including the posterior, lateral, posterolateral, anterolateral, and anterior locations of the torso of a patient 14. The electrodes 112 may be positioned proximate the tissue (e.g., skin) of the patient to acquire electrical signals or activity (e.g., body-surface potentials). In other words, the electrodes 112 may be positioned near or operably in contact with the tissue of the patient so as to be able to sense electrical signals or activity (e.g., body-surface potentials). Further, the electrodes 112 may be described as being "on" and/or secured to the skin of the patient. Still further, the electrodes 112 may be attached to the tissue of the patient using a conductive adhesive such as a conductive adhesive layer. Further the conductive adhesive and/or conductive adhesive layer may include conductive gel.

Further, the electrodes 112 may be electrically connected to interface/amplifier circuitry 116 via wired connection 118. The interface/amplifier circuitry 116 may be configured to amplify the signals from the electrodes 112 and provide the signals to the computing apparatus 140. Other exemplary systems may use a wireless connection to transmit the signals sensed by electrodes 112 to the interface/amplifier circuitry 116 and, in turn, the computing apparatus 140, e.g., as channels of data. For example, the interface/amplifier circuitry 116 may be electrically coupled to each of the computing apparatus 140 and the display apparatus 130 using, e.g., analog electrical connections, digital electrical connections, wireless connections, bus-based connections, network-based connections, internet-based connections, etc.

Although in the example of FIG. 2 the electrode apparatus 110 includes a strap 113, in other examples any of a variety of mechanisms, e.g., tape or adhesives, may be employed to aid in the spacing and placement of electrodes 112. In some examples, the strap 113 may include an elastic band, strip of tape, or cloth. In other examples, the electrodes 112 may be placed individually on the torso of a patient 14. Further, in other examples, electrodes 112 (e.g., arranged in an array) may be part of, or located within, patches, vests, and/or other manners of securing the electrodes 112 to the torso of the patient 14.

The electrodes 112 may be configured to surround the heart of the patient 14 and record, or monitor, the electrical signals associated with the depolarization and repolarization of the heart after the signals have propagated through the torso of a patient 14. Each of the electrodes 112 may be used in a unipolar configuration to sense the torso-surface potentials that reflect the cardiac signals. The interface/amplifier circuitry 116 may also be coupled to a return or indifferent electrode (not shown) that may be used in combination with each electrode 112 for unipolar sensing. In some examples, there may be about 12 to about 50 electrodes 112 spatially distributed around the torso of patient. Other configurations may have more or fewer electrodes 112.

The computing apparatus 140 may record and analyze the electrical activity (e.g., torso-surface potential signals) sensed by electrodes 112 and amplified/conditioned by the interface/amplifier circuitry 116. The computing apparatus 140 may be configured to analyze the signals from the electrodes 112 to provide as anterior and posterior electrode signals, body surface cardiac electrical activation times, and surrogate cardiac electrical activation times, e.g., representative of actual, or local, electrical activation times of one or more regions of the patient's heart as will be further described herein. Further, the electrical signals measured at the left anterior surface location of a patient's torso may be representative, or surrogates, of electrical signals of the left anterior left ventricle region of the patient's heart, electrical signals measured at the left lateral surface location of a patient's torso may be representative, or surrogates, of electrical signals of the left lateral left ventricle region of the patient's heart, electrical signals measured at the left posterolateral surface location of a patient's torso may be representative, or surrogates, of electrical signals of the posterolateral left ventricle region of the patient's heart, and electrical signals measured at the posterior surface location of a patient's torso may be representative, or surrogates, of electrical signals of the posterior left ventricle region of the patient's heart. In one or more embodiments, measurement of activation times can be performed by measuring the period of time between an onset of cardiac depolarization (e.g., onset of QRS complex) and an appropriate fiducial point such as, e.g., a peak value, a minimum value, a minimum slope, a maximum slope, a zero crossing, a threshold crossing, etc. In one or more embodiments, activation times may be generally determined by measuring the time from the earliest onset time within electrical activity from a plurality of external electrodes over a cardiac cycle (e.g., a depolarization portion of the cardiac cycle, the QRS complex, etc.) to the steepest, or maximum, negative slope within the electrical activity monitored by the particular external electrode for which the activation time is being calculated for.

Additionally, the computing apparatus 140 may be configured to provide graphical user interfaces depicting the body surface cardiac electrical activation times and/or surrogate cardiac electrical activation times obtained using the electrode apparatus 110. Exemplary systems, methods, and/or interfaces may noninvasively use the electrical information collected using the electrode apparatus 110 to evaluate a patient's cardiac condition and/or cardiac therapy being delivered to the patient.

FIG. 3 illustrates another exemplary electrode apparatus 110 that includes a plurality of electrodes 112 configured to surround the heart of the patient 14 and record, or monitor, the electrical signals associated with the depolarization and repolarization of the heart after the signals have propagated through the torso of the patient 14. The electrode apparatus 110 may include a vest 114 upon which the plurality of electrodes 112 may be attached, or to which the electrodes 112 may be coupled. In at least one embodiment, the plurality, or array, of electrodes 112 may be used to collect electrical information such as, e.g., anterior and posterior electrode signals, body surface cardiac electrical activation times and surrogate cardiac electrical activation times. Similar to the electrode apparatus 110 of FIG. 2, the electrode apparatus 110 of FIG. 3 may include interface/amplifier circuitry 116 electrically coupled to each of the electrodes 112 through a wired connection 118 and be configured to transmit signals from the electrodes 112 to computing apparatus 140. As illustrated, the electrodes 112 may be distributed over the torso of a patient 14, including, for example, the anterior, lateral, posterolateral, anterolateral, and posterior surfaces of the torso of the patient 14.

The vest 114 may be formed of fabric with the electrodes 112 attached to the fabric. The vest 114 may be configured to maintain the position and spacing of electrodes 112 on the torso of the patient 14. Further, the vest 114 may be marked to assist in determining the location of the electrodes 112 on the surface of the torso of the patient 14. In one or more embodiments, the vest 114 may include 17 or more anterior electrodes positionable proximate the anterior torso of the patient, and 39 or more posterior electrodes positionable proximate the posterior torso of the patient. In some examples, there may be about 25 electrodes 112 to about 256 electrodes 112 distributed around the torso of the patient 14, though other configurations may have more or less electrodes 112.

As described herein, the electrode apparatus 110 may be configured to measure electrical information (e.g., electrical signals) representing different regions of a patient's heart. For example, the electrical signals, or electrode signals, of different regions of a patient's heart can be approximated from surface electrocardiogram (ECG) signals measured using surface electrodes in proximity to surface areas corresponding to the different regions of the patient's heart.

As described herein, the exemplary systems, methods, and interfaces may be used to provide noninvasive assistance to a user in the evaluation of a patient's cardiac health or status, and/or the valuation of cardiac therapy (e.g., cardiac therapy being presently-delivered to a patient during implantation or after implantation). Further, the exemplary systems, methods, and interfaces may be used to assist a user in the configuration of the cardiac therapy being delivered to a patient. For instance, the exemplary systems, methods, and interfaces may be used to test a plurality of various cardiac therapy settings and present the results of the various cardiac therapy settings to a user via the graphical user interface. Further, for instance, the exemplary systems, methods, and interfaces may test a plurality of various cardiac therapy settings and present one or more effective cardiac therapy settings to the user. In at least one embodiment, the exemplary systems, methods, and interfaces may automatically program the cardiac therapy apparatus to use the effective cardiac therapy settings.

Figure 4A:
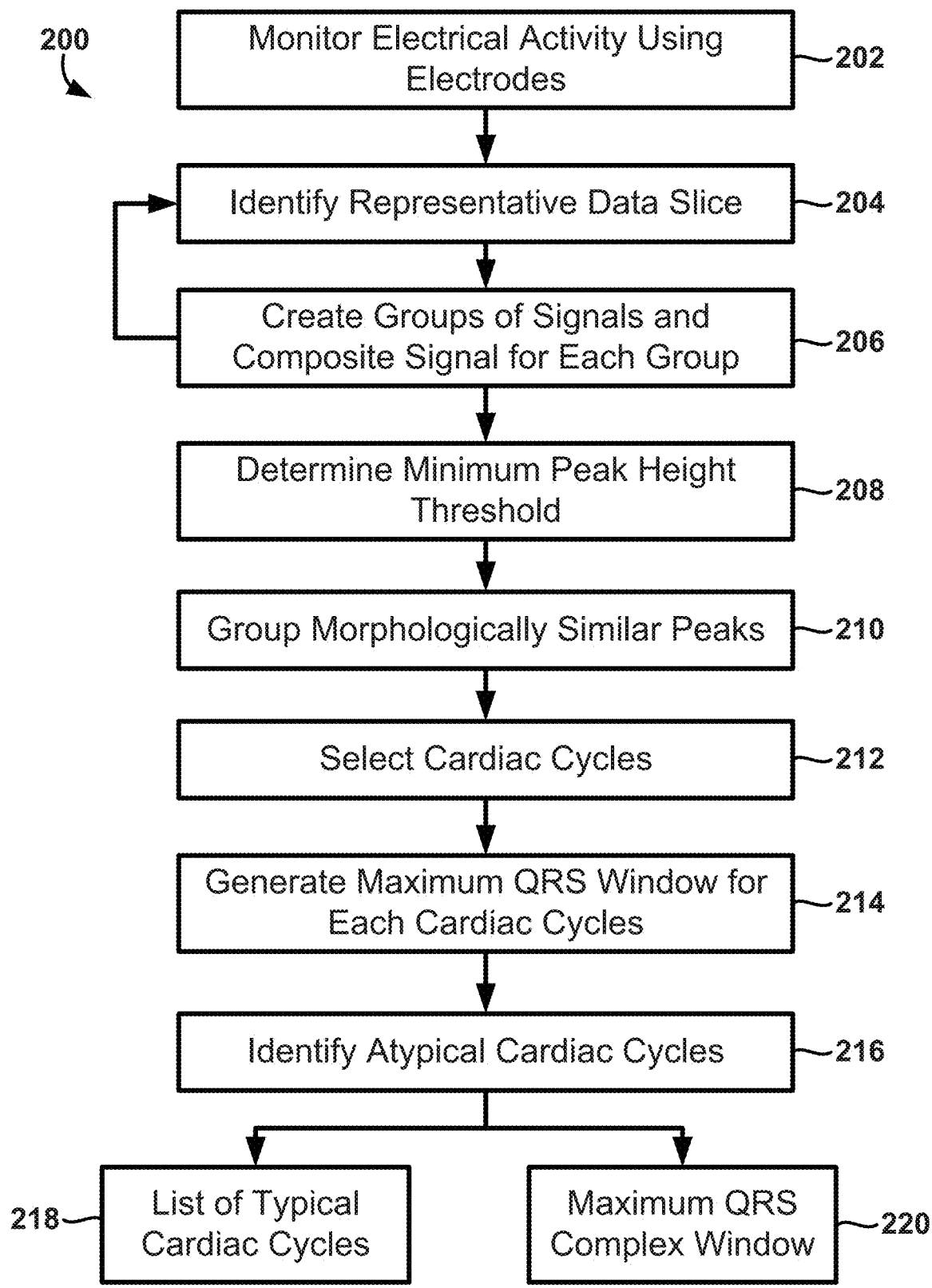
FIG. 4A is a block diagram of an exemplary method for determining typical cardiac cycles, or beats, and maximum QRS windows.

Exemplary method 200 depicted in FIG. 4A may be used to determine typical cardiac cycles, or beats, and maximum QRS windows from a plurality of cardiac signals over a plurality of cardiac cycles. The exemplary method 200 may be generally described as being used in the evaluation of a patient's cardiac health and/or cardiac therapy being delivered to the patient. More specifically, the exemplary method 200 may be described as taking raw electrode signal data captured from a plurality of electrodes such as external, surface electrodes coupled to, or attached, to patient's skin, e.g., using the apparatus and systems described herein with respect to FIGS. 1-3, and determining from the raw electrode signal data which of a plurality of cardiac cycles represent typical cardiac cycles, or beats, of a patient. Such typical cardiac cycles, or beats, may be useful in further analysis of the cardiac activity of the patient. In other words, the exemplary method 200 may be described as being a filter, or selection step, to determine what electrode signal data may be useful or helpful in the additional exemplary systems, methods, and interfaces described herein to assist in the evaluation of a patient's cardiac health and/or cardiac therapy being delivered to the patient.

Further, a typical cardiac cycle, or beat, may be described as being representative of a commonly occurring cardiac cycle of the patient so as to be useful or helpful in evaluating a patient's cardiac health and/or cardiac therapy being delivered to the patient. Since the exemplary method 200 may result in identification of one or more typical cardiac cycles, or beats, from a plurality of cardiac cycles, it may be described that some of the plurality of cardiac cycles were determined to be atypical or statistically not representative of a typical cardiac cycle of the patient so to be not useful or helpful in evaluating a patient's cardiac health and/or cardiac therapy being delivered to the patient.

The exemplary method 200 may include monitoring, or measuring, electrical activity using a plurality of electrodes 202 over a plurality of cardiac cycles or heart beats. As described herein, the plurality of electrodes may include external, surface electrodes coupled to, or attached, to patient's skin, e.g., using the apparatus and systems described herein with respect to FIGS. 1-3. Additionally, although not further described herein with respect to the exemplary embodiments, the plurality of electrodes may include implantable electrodes implanted in one or more locations with a patient, e.g., using the apparatus and systems described herein with respect to FIGS. 9-11. Still further, although not further described herein with respect to the exemplary embodiments, the plurality of electrodes may further include temporarily-implanted (e.g., non-permanent, not long term, etc.) electrodes such as, e.g., electrodes located in the cavity of a patient's heart using basket catheter or the like, electrodes located outside the heart but around the heart (e.g., epicardial space) using a "sock mapping" tool or the like. Yet still further, although not further described herein with respect to the exemplary embodiments, the electrodes, or electrode apparatus, may include a mix, or combination, of external and implanted electrodes. Regardless of the electrode apparatus utilized, the exemplary method 200 includes monitoring electrical activity 202, and more specifically, cardiac signals or ECG signals, from at least two electrodes or channels.

Since the electrical activity is being monitored, or measured, 202 using a plurality of electrodes, the result may be a plurality of electrode signals from and affiliated, or corresponding to, such electrodes. For example, if the electrode apparatus includes 40 electrodes, the monitoring process 202 may result in 40 different electrode signals monitored over a plurality of cardiac cycles. Further, some electrodes may not provide a useful signal, e.g., if the electrode is not effectively in contact with the patient's tissue, the electrode is malfunctioning, etc., and it is to be understood that those such electrodes may be filtered out, or removed from, further consideration of the exemplary methods, systems, and interfaces described further herein.

Once the electrical activity has, or the electrode signals have, been captured (e.g., monitored, measured, recorded, etc.), the exemplary method 200 may identify a representative data slice, or electrode signal portion, of each of the plurality of electrode signals 204 that may be used to group the electrode signals 206. For example, a time period (e.g., window, slice, length, etc.) may be selected (e.g., automatically by the method, at least initially by a user, etc.), and each of the electrode signals may be "cut down" into an electrode signal slice, or portion, according to the selected time period. Generally, the selected time period may be described as an amount of time configured to capture a complete QRS complex (e.g., mainly non-isoelectric content), for example so as to be useful to compare one or more waveform features, or morphologies, of each electrode signal. For example, the selected time period, or slice, may be about 1000 milliseconds. Further, for example, the selected time period, or slice, may be greater than or equal to about 700 milliseconds, greater than or equal to about 800 milliseconds, greater than or equal to about 900 milliseconds, greater than or equal to about 950 milliseconds, etc. Further, for example, the selected time period, or slice, may be less than or equal to about 1300 milliseconds, less than or equal to about 1200 milliseconds, less than or equal to about 1100 milliseconds, less than or equal to about 1050 milliseconds, etc. Nonetheless, the selected time period used to identify the representative data slice 204 may be based on the patient's heart rate (e.g., paced heart rate or intrinsic heart rate). In at least one embodiment, the selected time period used to identify the representative data slice 204 may be selected, or picked, by a physician (e.g., who may review electrode signal data when making such selection). In at least one embodiment, the selected time period used to identify the representative data slice 204 may be may be selected, or determined, by an automated process executed by a computer processor or processing circuitry.

The exemplary method 200 may then attempt to group the electrode signal portions (e.g., within the slice, or time window, as previously identified 204) according to morphologic similarity into one or more morphologically similar groups, and create, or generate, one or more composite signal 206 from each of the morphologically similar groups. In other words, the morphology of a portion, or slice, of each of the electrode signals may be analyzed, the electrode signals may be grouped based on the morphology analysis, and then a composite signal for each different morphologically-similar group may be based on, or generated using, the entirety of each electrode signal of each different morphologically-similar group. Thus, each composite signal may be described as corresponding to a morphologically similar group of electrode signals (which are grouped based on a window, or slice, of each of the electrode signals).

For example, the morphology of each of the plurality of electrode signal portions may be compared to each other, and the electrode signal portions having similar morphology may be grouped. Each morphologically-similar group may then be used to generate the composite signal that, e.g., may be representative of that particular morphologically similar group. In other words, the process 206 may result in one or more or a plurality of morphologically-similar groups, and (even though the grouping was based only on a data portion, or slice, of each electrode signal) the entire electrode signals of each of the morphologically-similar groups may be used to generate, or compute, a composite signal representative thereof. In at least one embodiment, the composite signal may be an average signal generated for each morphologically-similar group (e.g., based on each electrode signal of the morphologically similar group). In other embodiments, the composite signal may be a curve to fit the electrode signals of the morphologically similar group.

If no electrode signal portions or not enough electrode signal portions are morphologically similar so as to be grouped or too many morphologically distinct groups are identified in process 204, the method 200 may return to identifying a representative data slice 202 and changing the selected time period, or slice, to a different value than was previously used. For example, the previously-used selected time period, or slice, may be reduced or increased by a selected percentage or time value so as to reflect the most likely heart rate, or cardiac cycle length, for the patient. Then, the method 200 may again attempt to group the electrode signal portions according to morphologic similarity into one or more morphologically similar groups, and create, or generate, one or more composite signal 206 from each of the morphologically similar groups. In other words, the method 200 may re-slice the plurality of electrode signals using a different, or revised, time period 204 in response to unsuccessful grouping 206 of the plurality of electrode signal portions, and then re-try such grouping using the new data portion or slice 206. For example, if no groups are identified, a longer cycle length or slice may be used, and for example, if too many groups are identified (e.g., and if such groups include a small number of electrode signals), the shorter cycle length or slice may be used.

Thus, the processes 204 and 206 may result in a plurality of morphologically-similar groups of electrode signals and a plurality of composite signals corresponding to the morphologically similar groups. In one embodiment, an appropriate minimum peak height limit threshold may be determined 208 and set for each of the composite signals. The exemplary method 200 may then not analyze peaks or data below the minimum peak height limit threshold when determining peaks later thereon. In other words, the method 200 may simply not "look under" minimum peak height limit threshold within the duration of the composite signal.

The exemplary method 200 may then group morphologically similar peaks 210 that have features consistent with QRS complexes across two or more (e.g., all) composite signals. For example, one or more, or a plurality, of fiducial points, markers, or characteristics of the peaks in each composite signal may be compared to each other resulting in groups of morphologically similar peaks. In at least one embodiment, one or more of peak amplitude, width, and/or prevalence could be used to identify QRS-complexes associated peaks for each composite signal. Thus, the process 210 may be described as looking at all of the composite signals to identify groups of morphologically-similar peaks to be used to determine if each cardiac cycle, or beat, was present across all or more the composite signals.

From the groups of morphologically-similar peaks, the exemplary method 200 may further select typical cardiac cycles, or beats, 212 based at least on the comparison of peaks appearing in multiple composite signals. In other words, typical cardiac cycles, or beats, may be selected 212 based on the groups of morphologically-similar peaks 210.

After the selection of typical cardiac cycles, or beats, beat-to-beat spacing may be determined using one or more exemplary processes to select a QRS window. The maximum QRS window may be defined as a maximum time period within which the QRS complex of particular cardiac cycle occurs. The maximum QRS window determination, or calculation, may be configured so as to include at least the PQ and QT intervals of each cardiac cycle. Additionally, and more specifically, the exemplary method 200 may generate a maximum QRS window for each cardiac cycle, or beat, 214 based on the beat-to-beat interval and using various exemplary equations, or processes, relating heart rate to PQ and QT interval durations.

The exemplary method 200 may further include identifying additional, potentially atypical, cardiac cycles, or beats, 216, which may be further analyzed if desired. For example, if gaps, or periods of time, longer than anticipated R-R intervals occur between identified typical beats, the exemplary method 200 may perform one or more similar or different processes as already performed on signal segments, or signal portions, that occur within such gaps. In one or more embodiments, different thresholds may be used when filtering 208 such atypical signal segments and/or grouping 210 the morphology of similar peaks in such atypical signal segments. In one or more embodiments, such identified additional cardiac cycles may be compared to one or more of the identified typical cardiac cycles to determine whether such additional cardiac cycles may be included in the result, or output, of method 200.

The result of the exemplary method 200 may be a list of typical cardiac cycles, or beats, 218 and the corresponding maximum QRS complex windows 220 for each typical cardiac cycle, which may be used by the exemplary systems, methods, and interfaces described further herein.

Figure 4B:
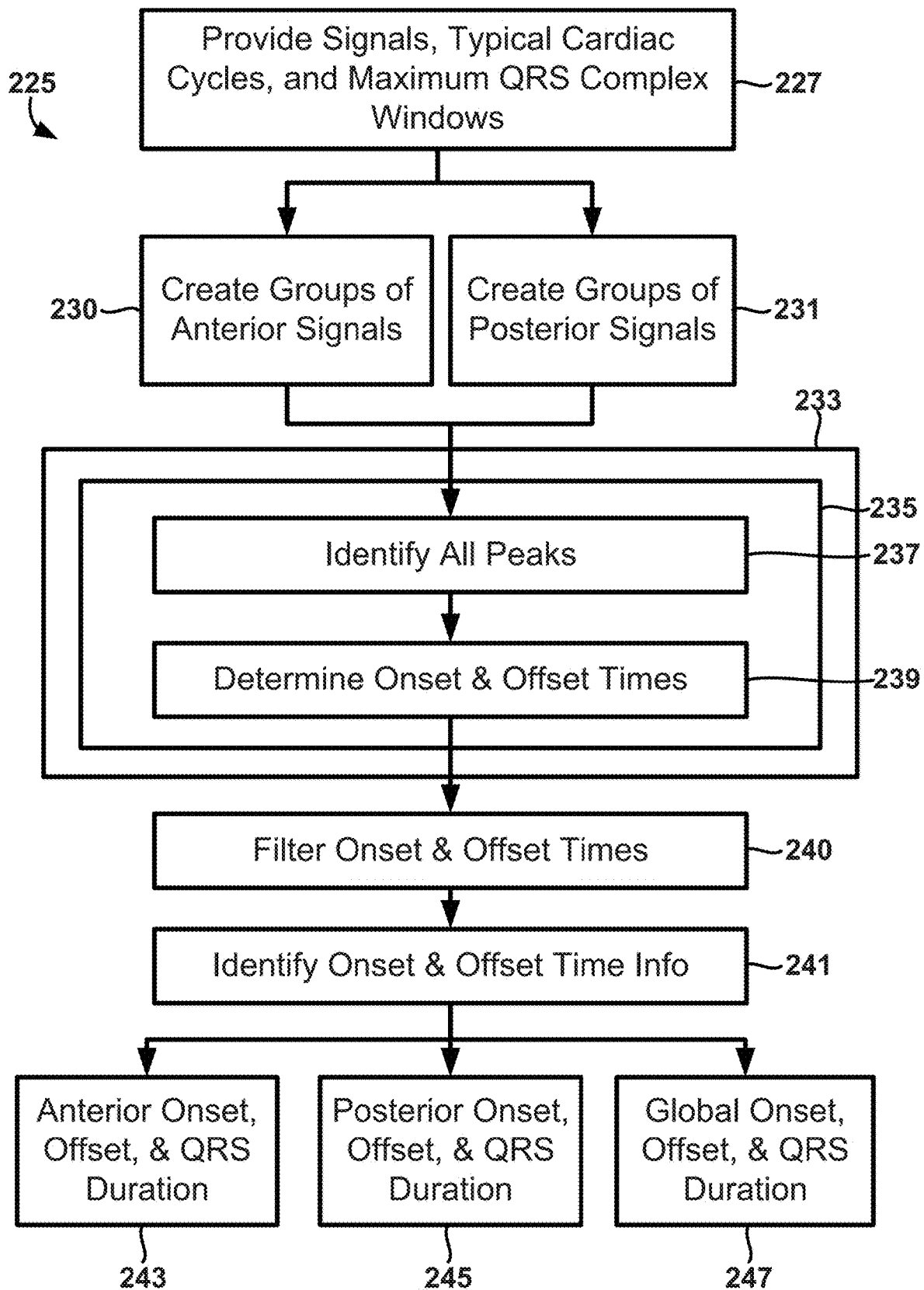
FIG. 4B is a block diagram of an exemplary method for determining various fiducial points within a QRS window of an electrode signal including QRS onset and offset.

An exemplary method 225 for determining various fiducial points within a QRS window of electrode signal including QRS onset and offset is depicted in FIG. 4B. The exemplary method 225 begins by providing a plurality of electrode signals, a list of typical cardiac cycles within the electrode signals, and a maximum QRS window for each of the typical cardiac cycles 227. In at least one embodiment, such information may be provided by the exemplary method 200 of FIG. 4A.

The exemplary method 225 may then separate and group the plurality of electrode signals based on physical location of the electrode signal acquisition (e.g., location on the torso of the patient where each electrode is applied). As shown, such grouping may create at least one group of anterior signals 230 and at least one group of posterior signals 231 from the plurality of electrode signals. More specifically and as described herein with respect to the exemplary electrode apparatus of FIGS. 1-3, the one or more posterior sets of electrode signals may be monitored from one or more electrodes of the plurality of electrodes located proximate the patient's posterior and the one or more anterior sets of electrode signals may be monitored from one or more electrodes of the plurality of electrodes located proximate the patient's anterior.

Additionally, although not depicted in FIG. 4B, outlier signals may be removed, or filtered, rom each group of the anterior and posterior signals by, for example, comparing the morphologic similarity of the electrode signals within each group. Thus, the group of anterior electrode signals may include electrode signals having morphologic similarity among their own anterior group and the group of posterior electrode signals may include electrode signals having morphologic similarity among their own posterior group.

For each typical cardiac cycle 233 and for each electrode signal 235, the exemplary method 225 may identify all of the peaks for each electrode signal within the maximum QRS window for the particular cardiac cycle 237, and then identify a QRS onset time and a QRS offset time for each electrode signal within the maximum QRS window for the particular cardiac cycle 239. The QRS onset times and QRS offset times may be determined using various fiducial points, various metrics, and the identified peaks. In at least one embodiment, QRS onset time may be determined using a derivative-based and/or amplitude-based cutoff preceding an initial peak within the maximum QRS window and QRS offset time may be determined using a derivative-based cutoff following a final peak within the maximum QRS window. In at least one embodiment, QRS onset time may be determined by a selected percentage change in area under the curve of the electrode signal and QRS offset time may be determined by a selected threshold of area remaining under the curve.

Thus, the result of processes 233, 235, 237, 239 may be QRS onset and offset times for each cardiac cycle (e.g., each typical cardiac cycle) of each of the plurality of electrode signals. The exemplary method 225 may further include filtering the QRS onset and offset times 240 to, e.g., remove outliers. For example, the exemplary method 225 may determine a range of QRS onset and offset times for the posterior set of electrode signals and for the anterior set of electrode signals. In other words, a range of QRS onset times and a range of QRS offset times may be determined for the posterior set of electrodes, and likewise, a range of QRS onset times and a range of QRS offset times may be determined for the anterior set of electrodes. The range may be a selected period of time within which the most amount of QRS onset or offset times occur for the particular group of electrode signals. Any QRS onset and offset times for the particular group of electrode signals that fall outside (e.g., greater than or less than) of a selected range, or time window, may be removed.

For example, the selected range may be about 20 milliseconds. The 20-millisecond range may be positioned (e.g., slid along the X-axis or time) over a plurality of QRS onset or offset times for a particular set of electrode signals until the position is found that includes the greatest number of onset or offset times within the 20-millisecond range. The onset or offset times that occur later than or before the positioned 20 millisecond range may be removed. Further, for example, the selected range, or time window, may be greater than or equal to about 5 milliseconds, greater than or equal to about 10 milliseconds, greater than or equal to about 15 milliseconds, greater than or equal to about 20 milliseconds, etc. Further, for example, the selected range, or time window, may be less than or equal to about 40 milliseconds, less than or equal to about 30 milliseconds, less than or equal to about 25 milliseconds, etc.

The exemplary method 225 may then identify additional onset and offset time information 241 from the determined QRS onset and offset times such as, for example, a set QRS onset time and a set QRS offset time for each of the anterior set and posterior set of electrode signals (e.g., earliest QRS onset time within the set of electrode signals, latest QRS offset time within the set of electrode signals, etc.) and a global QRS onset time and a global QRS onset time for all of the electrode signals (e.g., earliest QRS onset time within the all of electrode signals, latest QRS offset time within the all of electrode signals, etc.). Further, a QRS duration, which extends between an earliest QRS onset time and a latest QRS onset time may be determined for each set of electrode signals and all of the electrode signals. Thus, the method 225, as depicted, may result in an anterior QRS onset time, QRS offset time, and QRS duration 243, a posterior QRS onset time, QRS offset time, and QRS duration 245, and a global QRS onset time, QRS offset time, and QRS duration 247.

Figure 5:
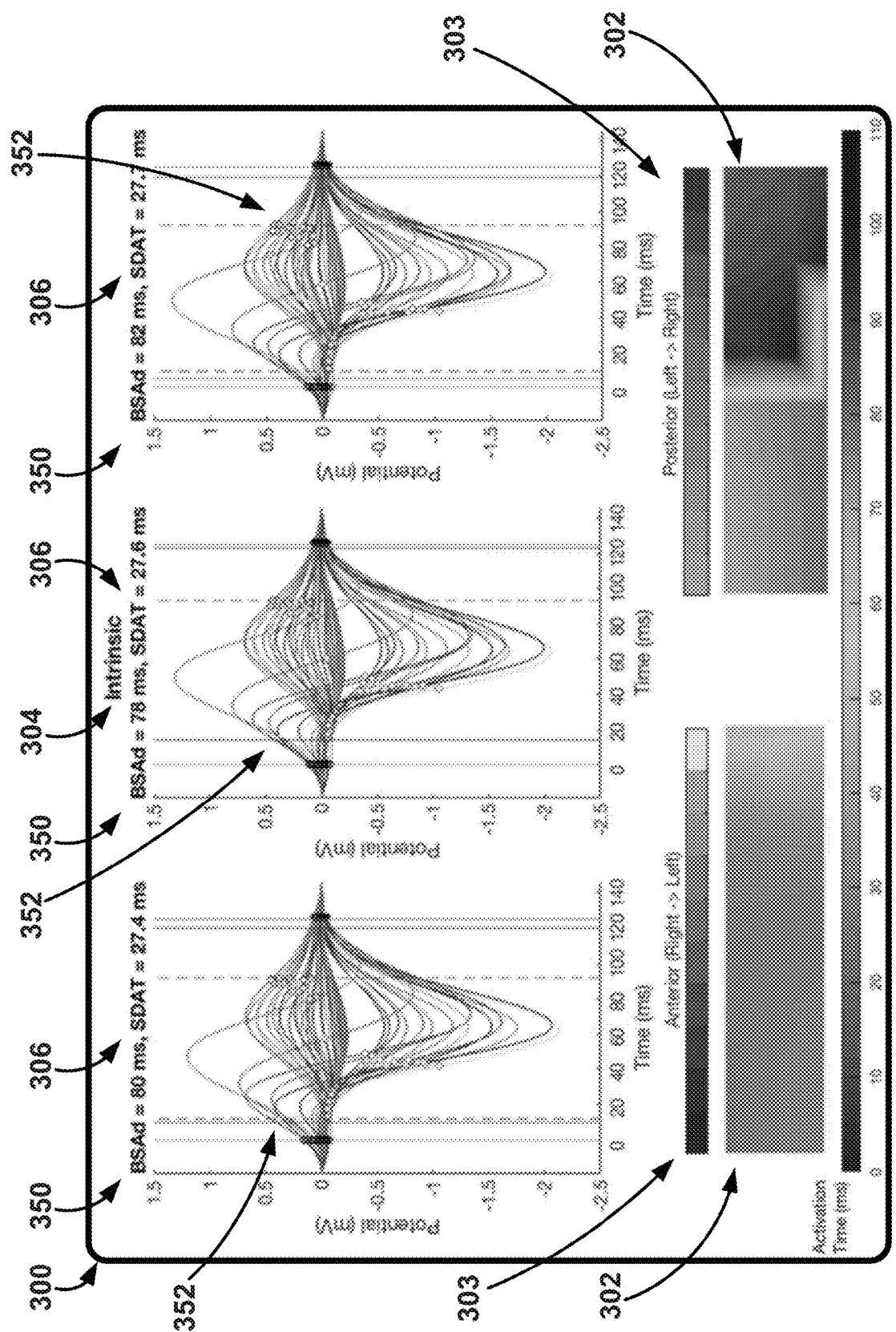
FIG. 5 is an exemplary graphical user interface depicting three single-cycle graphs and activation time maps.

As described herein, the exemplary systems and methods may provide interfaces which may be used to display, or depict, various electrode signal information. An exemplary graphical user interface 300 depicting three single-cycle graphs 350 and corresponding electrical activation time maps 302 is depicted in FIG. 5. In at least one embodiment such as depicted, the corresponding electrical activation time maps 302 may be representative of average activation times from the three cardiac cycles shown on the three single-cycle graphs 350 (e.g., a three-beat average). It is to be understood that each of the single-cycle graphs 350 may depict less than an entire cardiac cycle, and for example, may depict the QRS complex portion of a cardiac cycle as depicted herein. Each of the single-cycle graphs 350 may depict, or include, a plurality of electrode signals 352 displayed over the same period of time for the same cardiac cycle or heart beat, which will be described further herein with respect to FIG. 6A. Nonetheless, generally, each of the single-cycle graphs 350 may depict each of an anterior set of electrode signals and a posterior set of electrode signals, and the anterior set of electrode signals may be graphically distinguishable from the posterior set of electrode signals as will be described further herein.

Three different single-cycle graphs 350 are depicted on the graphical user interface 300 of FIG. 5. Each of different single-cycle graphs 350 may correspond to a different cardiac cycle, or heart beat, of a single patient. The cardiac cycles may be selected using the exemplary method 200 described herein with respect to FIG. 4A, and may represent typical cardiac cycles of the patient that may be useful to assess the patient's cardiac health.

The graphical user interface 300 further includes a cardiac therapy indication 304, which, in this embodiment, is an alphanumeric depiction of the type, if any, of cardiac therapy being presently delivered to the patient. In this way, a practitioner may be able to quickly ascertain what, if any, cardiac therapy is being delivered to the patient. In this example, no cardiac therapy is being delivered to the patient, and thus, the cardiac therapy indication 304 includes the word "Intrinsic" to indicate that the patient is not receiving any cardiac therapy during the monitoring, or recording, of electrical activity (e.g., body-surface potentials) for analysis by the systems and methods described herein. Thus, the remainder of the information depicted on the graphical user interface 300 is reflective of the patient's intrinsic conduction and/or cardiac rhythm. In another example, the cardiac therapy indication 304 may include the words "A-V synchronous pacing" to indicate that the patient is receiving A-V synchronous pacing cardiac therapy.

Further, the graphical user interface 300 further includes one more metrics of electrical cardiac heterogeneity 306. In this embodiment, two metrics of electrical cardiac heterogeneity are depicted: namely, body surface activation duration (BSAd) and standard deviation of activation times (SDAT), each of which will be described further herein.

Still further, as described above, the graphical user interface 300 may include, or depict, one or more electrical activation maps 302. The electrical activation maps 302 may be maps, or plots, of body surface cardiac electrical activation as measured by the exemplary systems and methods described herein for one or more of the cardiac cycles depicted by the single-cycle graphs 350. The electrical activation maps 302 may indicate the electrical activation at various locations about the surface of the patient's body, which in turn, may be related to the epicardial surface of the patient's heart. As shown, the electrical activation maps 302 include an anterior map on the left of the graphical user interface 300 which corresponds to the anterior side of the patient (e.g., measured by the external surface electrodes positioned on the anterior torso of the patient), and a posterior map on the right of the graphical user interface 300 which corresponds to the posterior side of the patient (e.g., measured by the external surface electrodes positioned on the posterior torso of the patient). Further, in at least one embodiment each of the electrical activation maps 302 may represent an average of the three cardiac cycles depicted in the single-cycle graphs 350. In other embodiments, each of the electrical activation maps 302 may represent just one of the three cardiac cycles depicted in the single-cycle graphs 350 or a different composite value of more than one of the three cardiac cycles depicted in the single-cycle graphs 350.

Further, the electrical activation maps 302 may be described as being graphical representations of cardiac electrical activation times from the monitored electrical activity about a portion of human anatomy. In at least one embodiment, the cardiac electrical activation times may be represented about a portion of human anatomy by color scaling a portion of human anatomy on the graphical user interface 132 according to the body surface cardiac electrical activation times and/or surrogate cardiac electrical activation times. Additional exemplary graphical representations of body surface cardiac electrical activation times and/or surrogate electrical activation times that may utilize or be utilized by the exemplary systems and methods described herein may be described in U.S. Pat. No. 9,986,928 issued Jun. 5, 2018, U.S. Pat. No. 9,993,172 issued Jun. 12, 2018, U.S. Pat. No. 10,206,601 issued Feb. 19, 2019, and U.S. Pat. No. 9,591,982 issued Mar. 14, 2017, U.S. Pat. No. 8,972,228 issued Mar. 3, 2015 and entitled "Assessing Intra-Cardiac Activation Patterns" and U.S. Pat. No. 9,510,763 issued Dec. 6, 2016 and entitled "Assessing Intra-Cardiac Activation Patterns and Electrical Dyssynchrony," each of which is hereby incorporated by reference in its entirety.

A user may desire to know which of the plurality of electrode signals 352 depicted in the single-cycle graphs 350 corresponds to a specific location within the electrical activation maps 302. Thus, the exemplary graphical user interface 300 may allow a user to select (e.g., touch using a finger, click using a pointing device such as a mouse, etc.) any location, or area, of the electrical activation maps 302, and the electrode signal corresponding to the selected location, or area, (e.g., the electrode signal that is monitored closest to the selection) may be graphically emphasized among the plurality of electrode signals 352 on one or more of the single-cycle graphs 350 such that a practitioner may quickly ascertain (e.g., see or visualize) which of the plurality of electrode signals 352 on the single-cycle graphs 350 of corresponds to the selected location, or area. For example, the corresponding electrode signal may change color, become highlighted, become animated (e.g., blink), etc. to indicate that it corresponds to the user selected location, or area, within the electrical activation maps 302. In other words, the corresponding electrode signal may be modified, or enhanced, to make it "stand out" among the plurality of electrode signals 352 of one or more single-cycle graphs 350.

Conversely, a user may desire to know where on the electrical activation maps 302 a particular electrode signal of the plurality of electrode signals 352 depicted in the single-cycle graphs 350 was derived, or measured, from. Thus, the exemplary graphical user interface 300 may allow a user to select (e.g., touch using a finger, click using a pointing device such as a mouse, etc.) any of the plurality of electrode signals 352 within the single-cycle graphs 350, and a location, or area, of the electrical activation maps 302 (e.g., the location or area where the electrode signal was obtained) may be graphically emphasized such that a practitioner may quickly ascertain (e.g., see or visualize) where on the electrical activation maps 304 the selected electrode signal corresponds to. For example, the corresponding location, or area, on the electrical activation maps 302 may change color, may be marked by a cross or circle, may become highlighted, may become animated (e.g., blink) to indicate that it corresponds to the selected electrode signal. In other words, the corresponding location, or area, of the electrical activations maps 302 may be modified, or enhanced, to make it "stand out."

Exemplary single-cycle graphs 350, which may be used in or in conjunction to the graphical user interface of FIG. 5, depicting a plurality of electrode signals 352 are depicted in FIGS. 6A-6D. The single-cycle graphs 350 may include different sets, or groups, of electrode signals within the plurality of electrode signals 352 that are graphically distinguished from one another. In these examples (although not show in the grayscale depictions), the anterior electrode signals 354 may be graphically distinguishable from the posterior electrode signals 356 by a change in color. In other words, the anterior electrode signals 354 may be a different color than the posterior electrode signals 356. For example, the anterior electrode signals 354 may be blue and the posterior electrode signals 356 may be green. In other embodiments, the anterior electrode signals 354 and the posterior electrode signals 356 may be graphically distinguishable from each other using different line weights, or widths, different line types such as, e.g., dashed lines, dotted lines, or wavy lines, different graphical animations such as blinking, flashing, twinkling, or highlighting, and/or different alphanumeric labeling.

Additionally, in one or more embodiments, each of the electrode signals within a graphical distinguished group, such as the anterior set of electrode signals 354, may be further graphically distinguished from the other electrode signals within the group based on various criteria such as, e.g., location. For example, a group, or set, of anterior electrode signals 352 may be graphically distinguished from the electrode signals 352 by being blue, and each of the anterior electrode signals 352 may be graphically distinguished from each other by being a different shade of blue. The shades of blue may be based on where the electrode signal was measured from about the patient's body. For example, anterior electrode signals 354 measured from electrodes proximate a right region of the patient's anterior torso may be darker than the anterior electrode signals 354 measured from electrodes proximate a left region of the patient's anterior torso. More specifically, the shades of blue of the anterior electrode signals 354 may range from darkest representing, or corresponding to, the right-most anterior electrode signals 354 to lightest representing, or corresponding to, the left-most anterior electrode signals 354. The graphical user interface 300 may further depict a color bar, or key, 303 for each of the anterior electrode signals 354 and the posterior electrode signals 352, which may be used by a user to determine where on the anterior and posterior each electrode signal derives, or is measured, from. More specifically, as shown, the anterior color bar 303 extends from a dark end representing electrode signals measured from the right side of the anterior of the patient to a light end representing electrode signals measured from the left side of the anterior of the patient, and the posterior color bar 303 extends from a light end representing electrode signals measured from the left side of the posterior of the patient to a dark end representing electrode signals measured from the right side of the posterior of the patient.

In one or more embodiments, each of the electrode signals 352 may be a different color from each other and may correspond to an electrode map depicted on a graphical user interface (not shown) such that a user may ascertain where each of the electrode signals 352 was measured from by consulting the electrode map. For example, the electrode map may depict the electrodes positioned about a model of a patient's torso, and each of the electrodes may be a different color that corresponds to its electrode signal 352 depicted on the single-cycle graph 350.

As described herein, activation times (e.g., body surface cardiac activation times) may be determined for each of the plurality of electrode signals 352. The single-cycle graph 350 may include activation time indicators 358, a few of which are labeled in FIG. 6A, based on the determined activation time of each of the plurality of electrode signals 352. Although the activation time indicators 358 of the single-cycle graph 350 of FIGS. 6A-6D are shown as circles along each of the plurality of electrode signals 352, it is to be understood that the activation time indicators 358 may be graphically depicted, or indicated, in multiple different ways such as, e.g., crosses, tick marks, icons, squares, differently colored or otherwise graphically distinguished segments of the electrode signal, etc.

Additionally, a composite, or global, QRS onset time and a composite, or global, QRS offset time of the electrode signals 352 may be indicated, or shown, by composite, or global, QRS onset time indicators 360 (a few of which are labeled in FIG. 6A) and composite, or global, QRS offset time indicators 362 (a few of which are labeled in FIG. 6A) on one or more of the electrode signals 352 of the single-cycle graph 350. Similar to the activation time indicators 358, the composite QRS onset time indicators 360 and composite QRS offset time indicators 362 are shown as circles along each of the plurality of electrode signals 352, and also similar to the activation time indicators 358, it is contemplated that the composite QRS onset time indicators 360 and composite QRS offset time indicators 362 may be depicted in many different ways such as, e.g., crosses, tick marks, icons, squares, differently colored or otherwise graphically distinguished segments of the electrode signal, etc.

Further, the set QRS onset and offset time indicators may be indicated, or depicted, on the single-cycle graph 350. For example, a set QRS onset indicator and a set QRS offset time indicator may be displayed for each of the graphical distinguishable sets, or groups, of electrode signals 352. In this example, the single-cycle graph 350 includes an anterior set, or group, of electrode signals 354 and a posterior set, or group, of electrode signals 356, and thus, each of the anterior set 354 and the posterior set 356 may include a set QRS onset indicator and a set QRS offset time indicator. More specifically, an anterior set QRS onset time indicator 364, an anterior set QRS offset time indicator 366, a posterior set QRS onset time indicator 368, and a posterior set QRS offset time indicator 370 may be displayed. As shown, each of the set QRS onset and offset time indicators 364, 366, 368, 370 are solid vertical lines. In other embodiments, the set QRS onset and offset time indicators 364, 366, 368, 370 may be any other graphical elements so to be able to be graphically distinguishable such that a user may determine that such indicators are indicative of the QRS onset and offset times for such sets, or groups, of electrode signals 352. In this example, the anterior QRS onset and offset time indicators 364, 366 may be the same color as the activation time indicators 358 of the anterior electrode signals 356 (e.g., orange), and the posterior QRS onset and offset time indicators 368, 370 may be the same color as the activation time indicators 358 of the posterior electrode signals 356 (e.g., purple).

Still further, breakthrough times may be depicted, or indicated, on the single-cycle graph 350. Breakthrough times may be described as the earliest activation time for a group, or set, of electrode signals 352. In this example, an anterior breakthrough time indicator 372 is shown indicating the earliest activation of the plurality of anterior signals 356 and a posterior breakthrough time indicator 374 is shown indicating the earliest activation of the plurality of posterior signals 356. As shown, the anterior and posterior breakthrough time indicators 372, 374 are dashed vertical lines. In other embodiments, the anterior and posterior breakthrough time indicators 372, 374 may be any other graphical elements so to be able to be graphically distinguishable such that a user may determine that such indicators are indicative of the breakthrough times for such sets, or groups, of electrode signals 352. Yet still further, the latest activation time may also be indicated by a latest electrical activation time indicator 376, which in this example is also a vertical dashed line but, in other embodiments, may be any suitable graphical indication.

From these various times and indicators displayed on the single-cycle graph 350, various time intervals, or time durations, may be determined which may be useful in assisting a user in evaluating cardiac therapy settings, and/or in assisting a user in assessing a patient's cardiac health. For example and as depicted on the single-cycle graph 350 of FIG. 6A, a global breakthrough duration, or time, 380 extending from earliest, or global, QRS onset time (as indicated by the earliest QRS onset time indicator 364) to the earliest activation time (as indicated by the earliest activation time indicator 372) may be determined. Further, for example, an anterior breakthrough duration, or time, may also be determined, which extends from earliest, or global, QRS onset time to the earliest anterior activation time may be determined. In this example, anterior breakthrough duration is the same as the global breakthrough duration 380, and, thus not labeled as such. Additionally, for example, a posterior breakthrough duration, or time, 381 extending from earliest, or global, QRS onset time (as indicated by the earliest QRS onset time indicator 364) to the earliest posterior activation time (as indicated by the earliest posterior activation time indicator 374) may be determined as indicated on the single-cycle graph 350 of FIG. 6A.

Figure 6A:
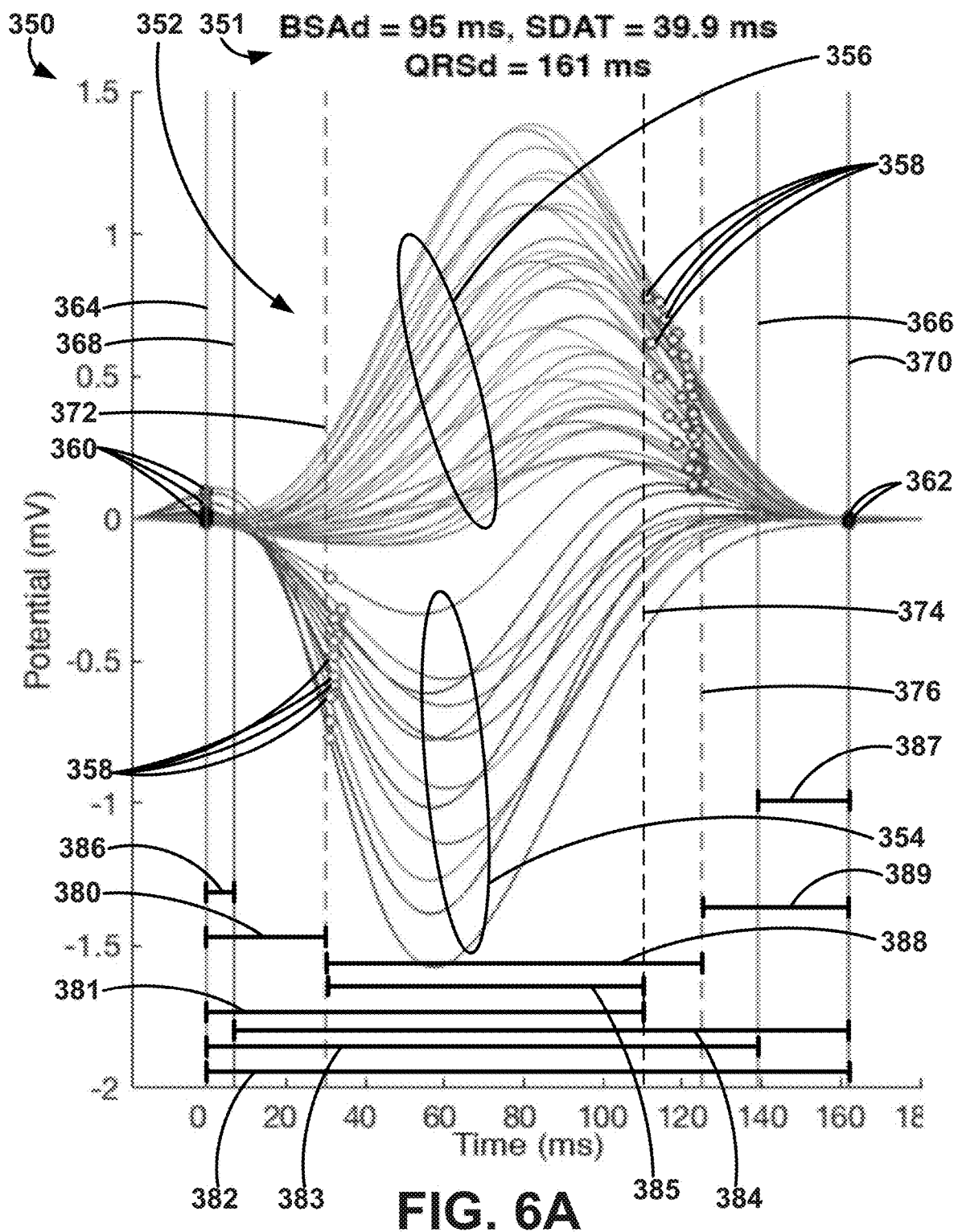
FIG. 6A is an exemplary single-cycle graph depicting a plurality of anterior and posterior electrode signals.

A global QRS duration 382 between the composite QRS onset time (as indicated by the earliest QRS onset time indicator 364) and the composite QRS offset time (as indicated by the latest QRS offset time indicator 370) may be determined as indicated on the single-cycle graph 350 of FIG. 6A. Further, a QRS duration may be determined for each of the anterior set of electrode signals 354 and the posterior set of electrode signals 356. For example, an anterior set QRS duration 383 between the anterior set QRS onset time (as indicated by the anterior QRS onset time indicator 364) and the anterior set QRS offset time (as indicated by the anterior QRS offset time indicator 366) may be determined as indicated on the single-cycle graph 350 of FIG. 6A. Further, for example, a posterior set QRS duration 384 between the posterior set QRS onset time (as indicated by the posterior QRS onset time indicator 368) and the posterior set QRS offset time (as indicated by the posterior QRS offset time indicator 370) may be determined as indicated on the single-cycle graph 350 of FIG. 6A.

Further, for example, an intra-breakthrough time duration, or delay, 385 may be determined between the earliest anterior activation time (as indicated by the anterior breakthrough time indicator 372) and the earliest posterior activation time (as indicated by the anterior breakthrough time indicator 374) as indicated on the single-cycle graph 350 of FIG. 6A. Still further, for example, an anterior-posterior QRS onset delay 386 may be determined between anterior and posterior QRS onset times (as indicated by the anterior and posterior onset time indicators 364, 368). And further, for example, an anterior-posterior QRS offset delay 387 may be determined between anterior and posterior QRS offset times (as indicated by the anterior and posterior offset time indicators 366, 370).

Still further, for example, an activation duration 388 may be determined between the earliest body surface activation time (as indicated by the earliest activation time indicator 372) and the latest activation time (as indicated by the latest activation time indicator 376) as indicated on the single-cycle graph 350 of FIG. 6A. The activation time duration 388, or body surface activation distance (BSAd), may be displayed on a graphical user interface proximate the single-cycle graph 350, and for example, a BSAd of 95 milliseconds is depicted above the single-cycle graph 350 as shown in FIG. 6A. Also, an activation duration to QRS end delay 389 may be determined between the latest activation time (as indicated by the latest activation time indicator 376) and the latest QRS offset time (as indicated by the posterior offset time indicator 370).

Figure 6B:
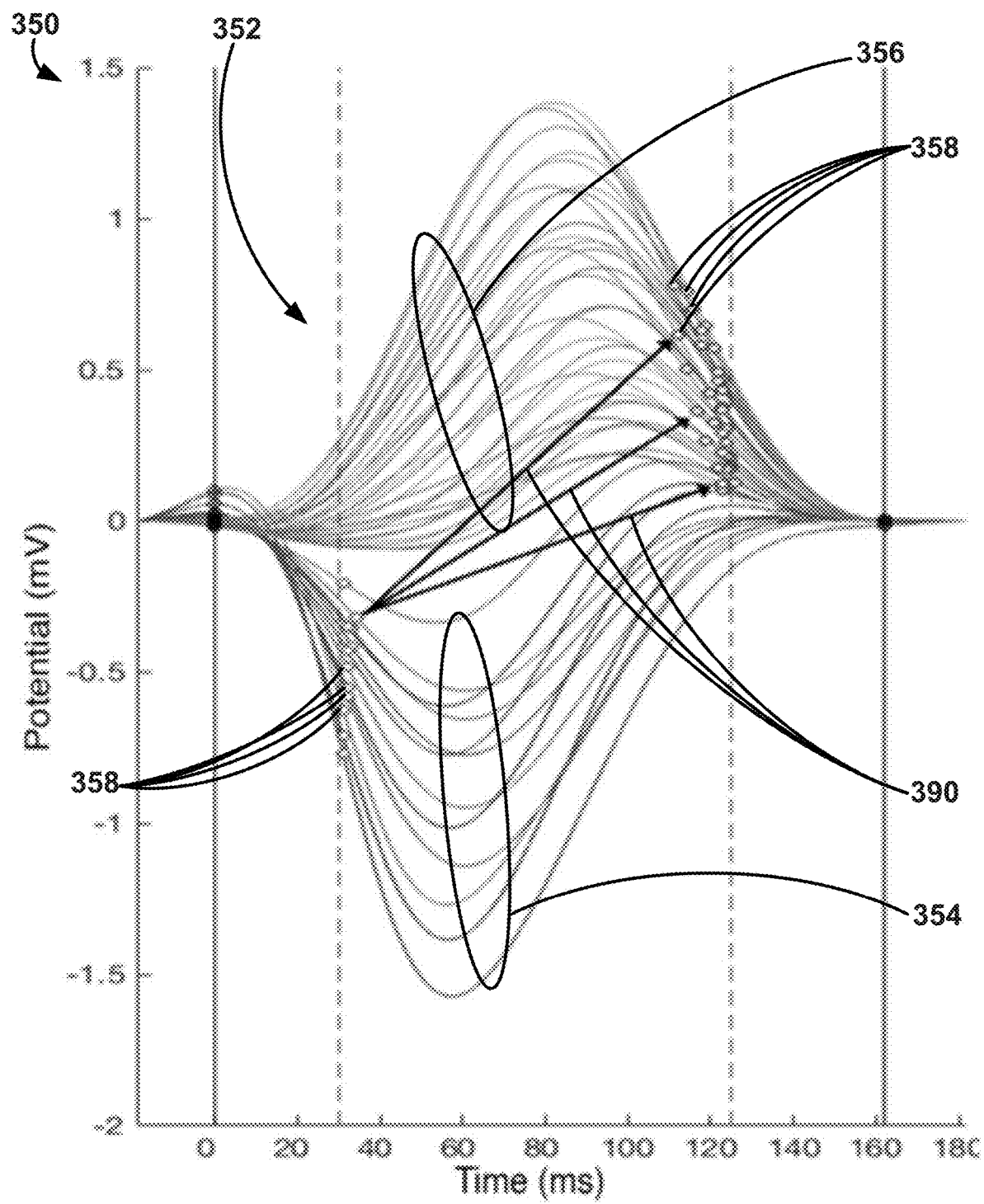
FIG. 6B is an exemplary single-cycle graph depicting a plurality of anterior and posterior electrode signals and few ventricular activation time distances.
Figure 6C:
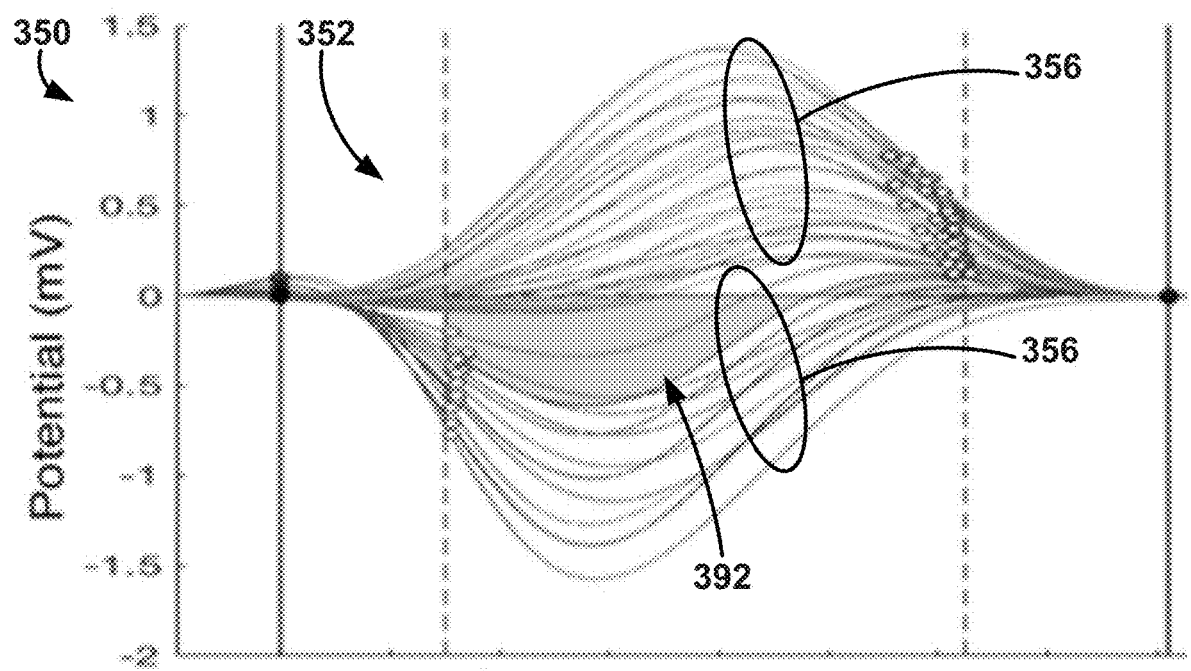
FIG. 6C are exemplary single-cycle graphs depicting a plurality of anterior and posterior electrode signals and a few anterior and posterior areas under the curve.
Figure 6C:
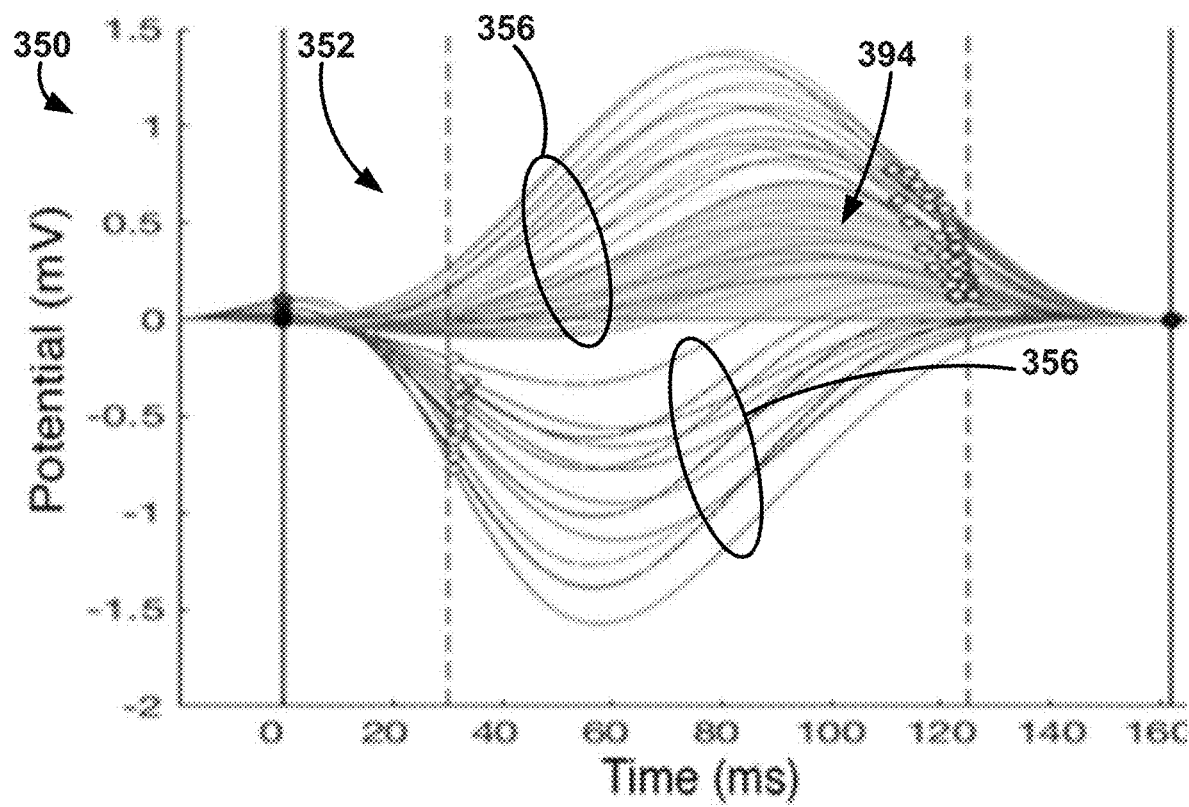
Figure 6D:
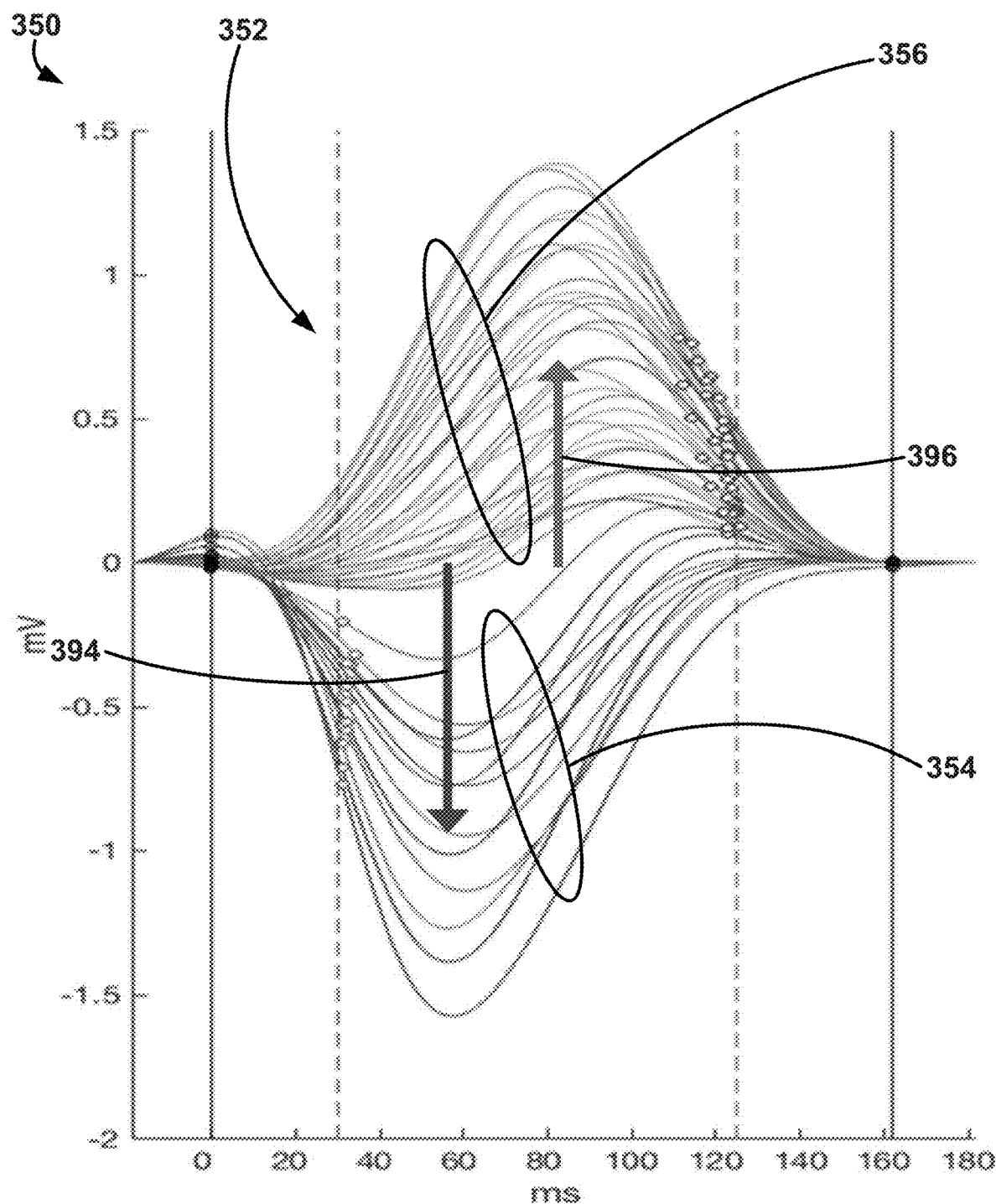
FIG. 6D is an exemplary single-cycle graph depicting a plurality of anterior and posterior electrode signals and anterior and posterior net heights.
Figure 7:
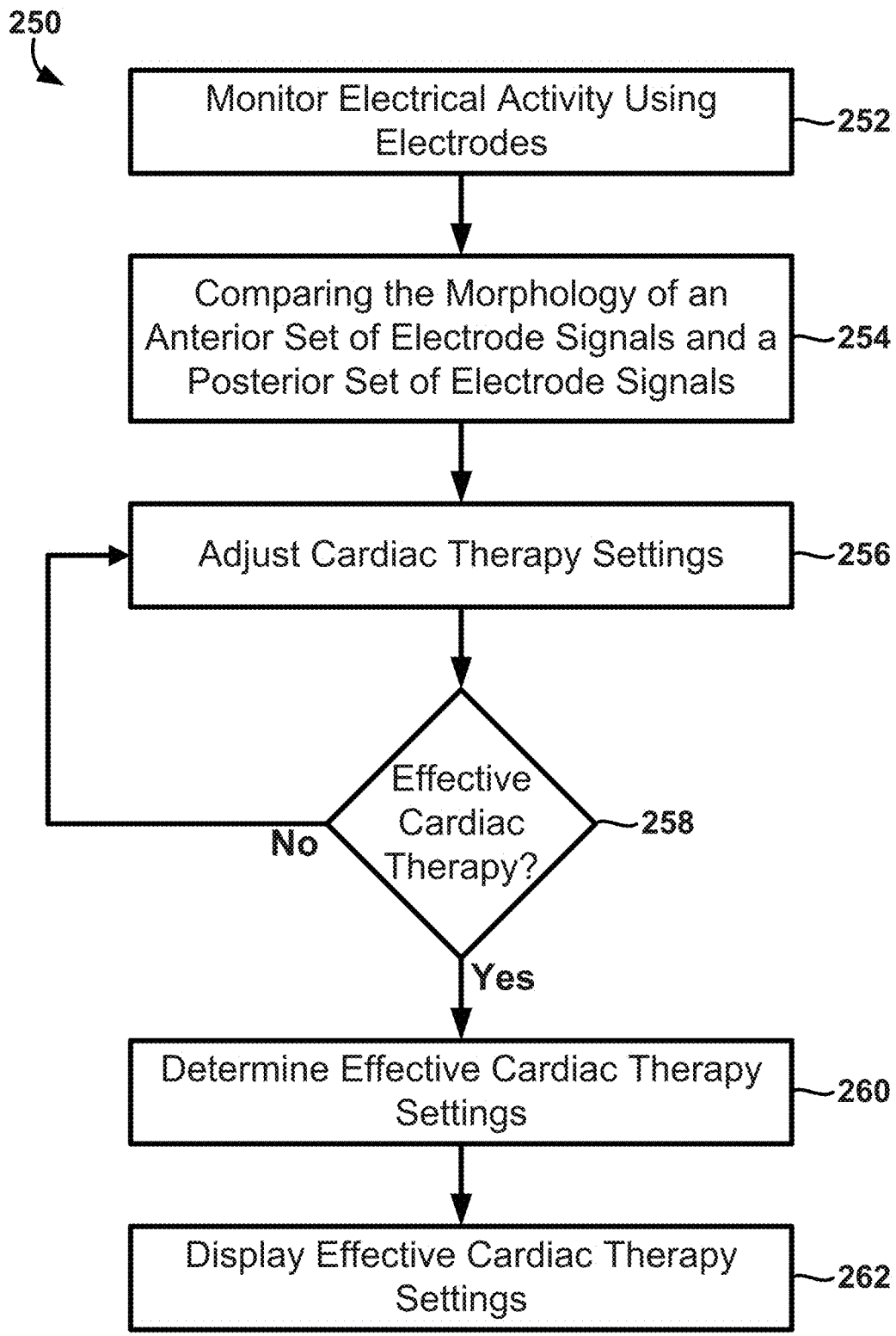
FIG. 7 is a block diagram of an exemplary method for comparing morphology of anterior and posterior sets of electrode signals and determining effective cardiac therapy settings.

The exemplary single-cycle graph 350 is further depicted in FIGS. 6B-6D for use when describing the generation, or determination, of various metrics of cardiac electrical heterogeneity from the plurality of electrode signals 352. An exemplary method 250 comparing the morphology of anterior and posterior sets of electrode signals 354, 356 for use with such metrics of cardiac electrical heterogeneity is depicted in FIG. 7.

The exemplary method 250 includes monitoring electrical activity using the plurality of electrodes 252, which may be similar to the monitoring and processes steps described herein with respect to methods 200, 225 described herein with reference to FIGS. 4A-4B. Regardless, the result of process 252 may be a plurality of electrode signals 352 over a single, typical cardiac cycle, which may be plotted, or depicted, on a single-cycle graph 350.

The exemplary method 250 may then compare 254 the morphology of the anterior set of electrode signals 354 and the posterior set of electrode signals 356 to, e.g., asses the cardiac electrical heterogeneity of the patient. Generally, it may be described that if the posterior set of electrode signals 356 are "flipped," "squished," and "crunched" (in other words, "inverted," "compressed," and "reduced") to correspond to the anterior set of electrode signals 354, then the cardiac electrical heterogeneity of the patient will have improved. Various metrics, or quantitative measures, may be reflective of the "flip," "squish," and "crunch" phenomenon. For example, changes in areas between the anterior and posterior waveforms, changes in distances between the anterior and posterior activation events, changes in body surface activation duration (BSAd), changes in anterior and/or posterior amplitudes, changes in ratios of maximum amplitude to minimum amplitude, and/or a combination of changes in amplitudes and amplitude ratios may be indicative of the "flip," "squish," and "crunch" phenomenon, which may correlate to an improvement in the cardiac electrical heterogeneity of the patient.

Such comparison may be completed, or "take place," automatically by a computing apparatus or partially by a computing apparatus with the assistance of a practitioner. For example, the computing apparatus may compare 254 the morphology of the anterior set of electrode signals 354 and the posterior set of electrode signals 356, and output a result such as an indication of the cardiac electrical heterogeneity of the patient, which may indicate whether the patient's cardiac health is acceptable and/or whether any presently-delivered cardiac therapy is effective. Further, for example, the computing apparatus may generate, or determine, and then display, or convey, one or more metrics of cardiac electrical heterogeneity that may be useful to a practitioner to determine the cardiac health of the patient and/or the effectiveness any presently-delivered cardiac therapy.

Cardiac electrical heterogeneity information and other cardiac therapy information may be described in U.S. Provisional Patent Application No. 61/834,133 entitled "METRICS OF ELECTRICAL DYSSYNCHRONY AND ELECTRICAL ACTIVATION PATTERNS FROM SURFACE ECG ELECTRODES" and filed on Jun. 12, 2013, which is hereby incorporated by reference it its entirety. Cardiac electrical heterogeneity information may be defined as information indicative of at least one of mechanical synchrony or dyssynchrony of the heart and/or electrical synchrony or dyssynchrony of the heart. In other words, cardiac electrical heterogeneity information may represent a surrogate of actual mechanical and/or electrical functionality. In at least one embodiment, the cardiac electrical heterogeneity information may include a standard deviation of ventricular activation times corresponding to some or all of the external electrodes, e.g., of the electrode apparatus 110. Further, regional cardiac electrical heterogeneity information may include standard deviations and/or averages of activation times corresponding to electrodes located in certain anatomic areas of the torso. For example, external electrodes on the left side of the torso of a patient may be used to compute regional left electrical heterogeneity information.

The cardiac electrical heterogeneity information may be generated using one or more various systems and/or methods. Cardiac electrical heterogeneity information may be generated using an array, or a plurality, of surface electrodes and/or imaging systems as described in U.S. Pat. No. 9,510,763 issued Dec. 6, 2016 and entitled "ASSESSING INRA-CARDIAC ACTIVATION PATTERNS AND ELECTRICAL DYSSYNCHRONY," U.S. Pat. No. 8,972,228 issued Mar. 3, 2015 and entitled "ASSESSING INTRA-CARDIAC ACTIVATION PATTERNS", and U.S. Pat. No. 8,180,428 B2 issued May 15, 2012 and entitled "METHODS AND SYSTEMS FOR USE IN SELECTING CARDIAC PACING SITES," each of which is incorporated herein by reference in its entirety.

One exemplary metric of cardiac electrical heterogeneity may be a standard deviation of activation-times (SDAT) measured by some or all of the electrodes on the surface of the torso of patient. In some examples, the SDAT may be calculated using the estimated cardiac activation times over the surface of a model heart. Further, the metrics of cardiac electrical heterogeneity 351 may be displayed on a graphical user interface proximate the single-cycle graph 350. For example, the SDAT of 39.9 milliseconds is depicted above the single-cycle graph 350 as shown in FIG. 6A.

Another exemplary metric of cardiac electrical heterogeneity may be an inter-activation event distance. The inter-activation event distance may be a value derived from, or based, on activation distances between each of the plurality of activation times of the anterior electrode signals 354 and the plurality of activation times of the posterior electrode signals 356. More specifically, an activation distance may be measured from each of the anterior activation times to each of the posterior activation times. Then, each of the activation distances may be used to generate an inter-activation event distance. For example, as shown in FIG. 6B, three activation distances 390 are depicted extending from a single anterior activation time indicator 358. An Euclidean distance may be measured from that same single anterior activation time indicator 358 to each of the plurality of posterior activation time indicators 358, and then the process may begin for the next anterior activation time indicator 358. In this way, if there are 10 anterior electrode signals 354, and thus, 10 anterior activation times, and 10 posterior electrode signals 356, and thus, 10 posterior activation times, 100 activation time distances (10×10) may be determined. Further, it is to be understood that the activation time distances may be measured both in the X-axis and Y-axis directions in this embodiment, and as such, this metric may be useful for indicating whether the electrode signals 352 may be "flipped" and "squished" as will be further described herein. In other embodiment, the activation time distances may be only measured in one of the X-axis and Y-axis directions.

As noted earlier, the plurality of activation time distances may be used to generate, or determine, an inter-activation event distance. In one example, the plurality of activation time distances may be averaged to generate the inter-activation event distance.

In other words, the activation time distances 390 may be described as extending between each activation event of the anterior electrodes and each activation event of the posterior electrodes. The inter-activation event distance may be the average of all of the paired Euclidean activation time distances between each of the anterior activation events and each of the posterior activation events based on the electrogram plot.

Another exemplary metric of cardiac heterogeneity may be a composite area under the curve (AUC) metric based on of the areas under the curve of the anterior set of electrode signals and the areas under the curve of the posterior set of electrode signals. More specifically, an area under the curve 392 for each of the anterior electrode signals 354 and an area under the curve 394 for each of the posterior electrode signals 354 as depicted in FIG. 6C may be determined, or calculated. The areas under the curve for the anterior electrode signals 354 may then be compared to the areas under the curve for the posterior electrode signals 356 to generate the composite area under the curve (AUC) metric. In other words, a difference between the area under the curve 392 for each of the anterior electrode signals 354 and the area under the curve 394 for each of the posterior electrode signals 354 may be generated, or calculated, resulting in the composite AUC metric.

In at least one embodiment, each area under the curve for an anterior electrode signal 354 may be compared to each of the areas under the curve for the posterior electrode signal 354. In this way, similar to the activation time distance metric, if there are 10 anterior electrode signals 354, and thus, 10 anterior areas under curve, and 10 posterior electrode signals 356, and thus, 10 posterior areas under curve, 100 area under curve metrics (10×10) may be determined by comparing the anterior electrode signals 354 to the posterior electrode signals 356.

In another embodiment, each anterior electrode signal 354 may be paired with only one posterior electrode signal 356, and their respective areas under curve may be compared. In this way, if there are 10 anterior electrode signals 354, and thus, 10 anterior areas under curve, and 10 posterior electrode signals 356, and thus, 10 posterior areas under curve, 10 pairs of signals may be compared resulting in 10 area under curve metrics. More specifically, the smallest area under the curve of the anterior electrode signals 354 may be compared to the smallest area under the curve of the posterior electrode signals 356, the second smallest area under the curve of the anterior electrode signals 354 may be compared to the second smallest area under the curve of the posterior electrode signals 356, and so on until areas under the curve of each pair of anterior and posterior signals 354, 356 is compared.

Then, a composite area under the curve metric may be determined based on the generated area under the curve metrics (e.g., based on each of the plurality of compared AUCs). In one example, the plurality of compared AUCs may be averaged to generate the composite area under the curve metric. It is to be understood, however, that any one more statistical computation may be used to generate the composite area under the curve metric from the plurality of compared AUCs. In other words, an average area between the anterior and posterior curves of the anterior and posterior electrode signals 354, 356 may be the average of all of the paired differences between each of the anterior curves and each of the posterior curves.

Another exemplary metric of cardiac heterogeneity may be a composite height metric based on the maximum heights of each of the anterior set of electrode signals 354 and the maximum heights of each of the posterior set of electrode signals 356. For example, the maximum heights of each of the plurality of electrode signals 352 may be determined, and then may be used to generate, or calculate, the composite height metric. More specifically, in one embodiment, the maximum height of the anterior electrode signals 354 may be compared to the minimum height of the anterior electrode signals 354 to provide a net maximum height of the anterior electrode signals 354 as indicated by the net anterior height 394 in FIG. 6D. Further, the maximum height of the posterior electrode signals 356 may be compared to the minimum height of the posterior electrode signals 356 to provide a net maximum height of the posterior electrode signals 356 as indicated by the net posterior height 396 in FIG. 6D. Then, a composite metric may be generated, or calculated, based the net maximum heights 394, 396 of the anterior and posterior electrode signals 354, 356. For example, the net direction of body surface cardiac electrical activity in the anterior-posterior plane may be determined using the average net posterior peak height minus the average anterior peak height.

Another exemplary metric of cardiac heterogeneity may be a ventricular electrical uncoupling (VEU) metric which may be a difference between the mean anterior and mean posterior activation times. The VEU may also be referred to as a body surface electrical uncoupling (BEU) since, e.g., the electrode signals may be captured from the body surface of the patient.

Thus, the method 250 may compare 254 the morphology of the anterior set of electrode signals 354 and the posterior set of electrode signals 356. The comparison 254 may provide one or more metrics of cardiac electrical heterogeneity, which may be used to assess the cardiac electrical heterogeneity of the patient. If the comparison 254 indicates that the patient's cardiac health may benefit from cardiac therapy or adjustment of the cardiac therapy being presently delivered, the method 250 may initiate or adjust cardiac therapy settings 256 and continue monitoring the electrical activity of the patient using the plurality of electrodes 252 and comparing the morphology of the anterior set of electrode signals 354 and the posterior set of electrode signals 356 to assess the newly-initiated cardiac therapy or newly-adjusted cardiac therapy.

The cardiac therapy may be adjusted, or modified, a plurality of different ways. For example, a pacing location may be changed (e.g., a pacing lead may be moved, different electrodes of a pacing lead may be used, a pacing vector may be changed, etc.). Further, for example, one or more timing intervals such as atrioventricular delay, intraventricular delay, etc. may be adjusted. Additionally, the type of cardiac therapy may also be adjusted. For instance, pacing therapy may be delivered as left-ventricle only pacing, biventricular pacing, multipoint pacing, etc., and each of the different types of pacing therapy may constitute an adjustment.

The method 250 may continue to adjust the cardiac therapy settings 256 until effective cardiac therapy (e.g., optimal cardiac therapy) is determined to be delivered 258 based on comparing 254 the morphology of the anterior set of electrode signals 354 and the posterior set of electrode signals 356. More specifically, the one or more metrics derived from the comparisons of the morphology of the anterior set of electrode signals 354 and the posterior set of electrode signals 356 may be used to determine whether the cardiac therapy being delivered at each of the adjusted cardiac therapy settings is effective. If the present cardiac therapy is determined to be ineffective (or less effective than optimal), the method 250 may return to adjusting the cardiac therapy settings 256. If the present cardiac therapy is determined to be effective (or more effective than other cardiac therapy settings) 260, the method 250 may display the effective cardiac therapy settings 262 to a practitioner, e.g., such that practitioner may program the cardiac therapy apparatus for the patient and/or may further evaluate the suggested effective cardiac therapy settings.

Figure 8A:
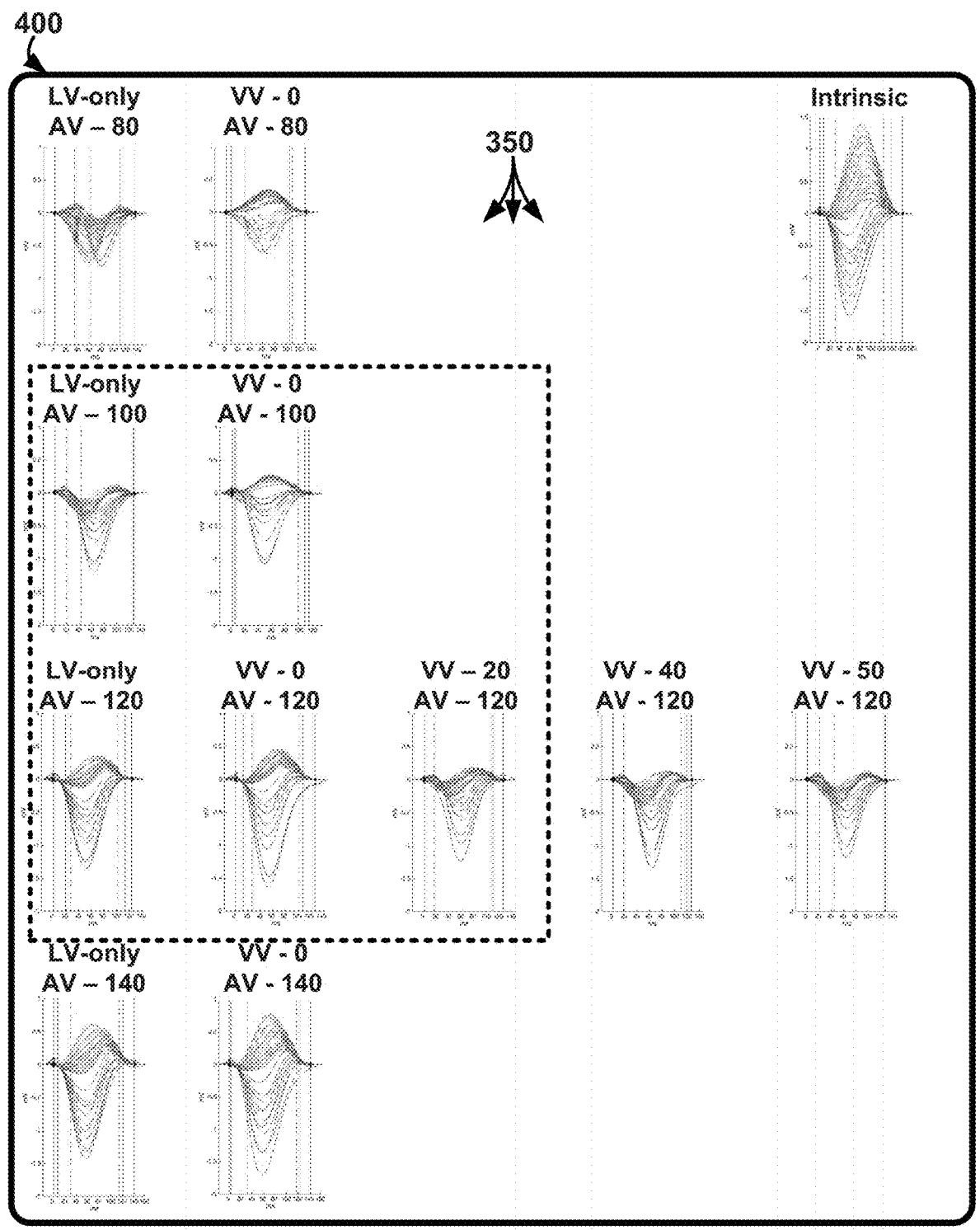
FIG. 8A is an exemplary graphical user interface depicting a plurality of single-cycle graphs corresponding to various cardiac therapy settings.

In one embodiment, the exemplary systems and methods may initiate cardiac therapy to a patient applying a plurality of different cardiac therapy settings over a plurality of cardiac cycles and display, on a graphical user interface, a plurality of single-cycle graphs 350 as shown on the graphical user interface 400 of FIG. 8A. As shown, each single-cycle graph 350 may correspond to a different cardiac cycle where different cardiac therapy settings are applied.

Further, the cardiac therapy settings (e.g., pacing settings) used for each of the plurality of single-cycle graphs 350 may be depicted proximate the corresponding single-cycle graphs 350. For example, the AV delay and VV delay are depicted above each of the single-cycle graphs 350 as shown in FIG. 8A.

The single-cycle graphs 350 may be deliberately arranged according to the cardiac therapy settings. For example, the single-cycle graphs 350 may be arranged in columns according to right ventricle pacing variations. As shown, the leftmost column may correspond to left ventricular pacing only and the right most column may correspond to a maximum intraventricular (VV) delay for biventricular pacing (which as shown in this example to be 50 milliseconds). The column immediately right of the left ventricular pacing only column may correspond to the first biventricular pacing settings where the VV delay is 0 milliseconds. For example, the single-cycle graphs 350 may be arranged in rows according to left ventricle pacing variations. As shown, the top row may correspond to a minimum atrioventricular (AV) delay of 80 milliseconds and the bottom row may correspond to a maximum AV delay of 140 milliseconds.

Additionally, the graphical user interface 400 may further depict a single-cycle graph of typical cardiac cycle of the patient during intrinsic rhythm, which in this example, is depicted in the upper right corner.

A practitioner may be to view, or look at, the graphical user interface 400 and ascertain which of the plurality of various cardiac therapy settings results in improvement of cardiac electrical heterogeneity of the patient by comparing the single-cycle graphs. More specifically, for example, the single-cycle graphs that show an effective amount of "flipping," "squishing," and "crunching" may be determined to provide an improvement of cardiac electrical heterogeneity of the patient.

Figure 8B:
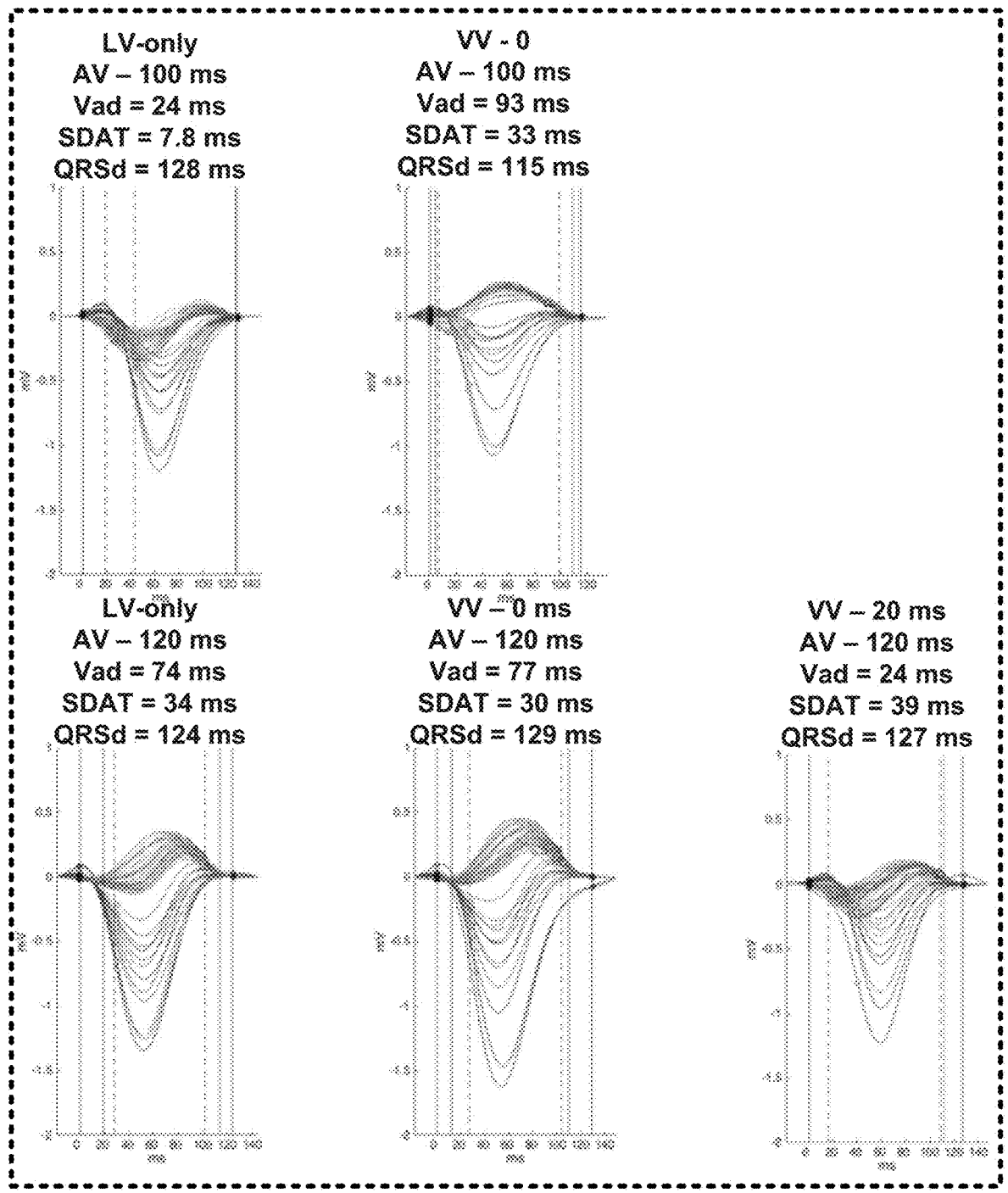
FIG. 8B is an enlarged view of a portion of the graphical user interface of FIG. 8A.

Although not depicted in FIG. 8A, one or more metrics of cardiac electrical heterogeneity including those derived from, or based on, comparisons of the anterior electrode signals 354 and the posterior electrode signals 356 may be depicted proximate each of the single-cycle graphs 350. For example, an enlarged view of a portion 402 of the graphical user interface 400 of FIG. 8A is depicted in FIG. 8B, which includes one or more metrics of cardiac electrical heterogeneity proximate each of the single-cycle graphs 350. As shown, the one or more metrics of cardiac electrical heterogeneity in this example are SDAT, QRSd, and VAd. It is to be understood that any other of the metrics of cardiac electrical heterogeneity described herein may be displayed proximate each of the single-cycle graphs 350 of the graphical user interface 400. Further, although not depicted herein, percentage improvements and other statistical values may be presented proximate each of the single-cycle graphs 350 so as to provide additional use information to practitioners.

Lastly, in at least one embodiment, single-cycle graph 350 corresponding to the determined most effective cardiac therapy settings may be indicated (e.g., highlighted, circle, animated, etc.) on the graphical user interface 400. In this way, a practitioner may be able to view the systems recommended cardiac settings in view of the other different cardiac settings.

Figure 9:
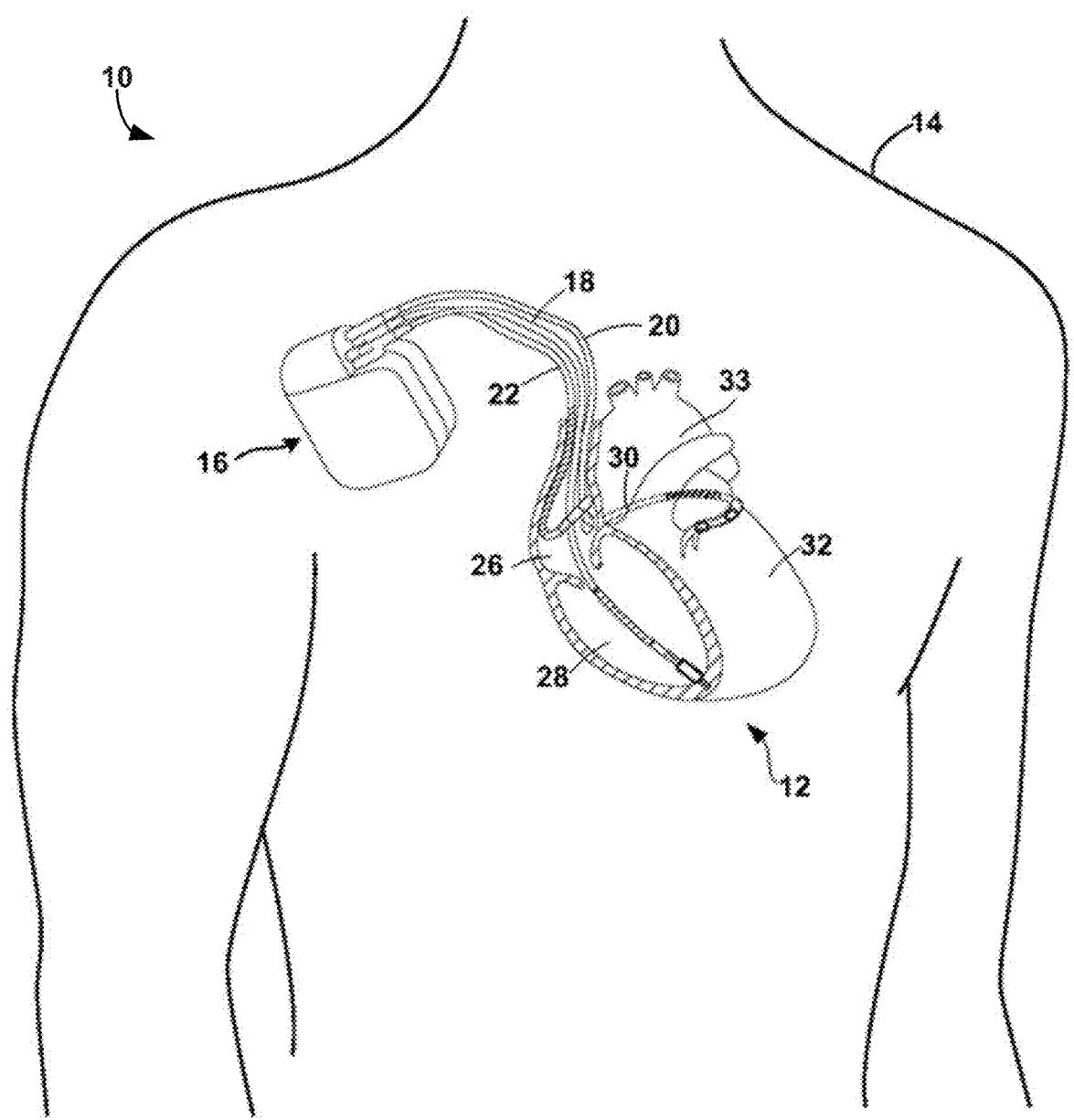
FIG. 9 is a diagram of an exemplary system including an exemplary implantable medical device (IMD).

Exemplary cardiac therapy may be further described herein with reference to FIGS. 9-11, which may be adjusted using the exemplary method 250. Additionally, the exemplary systems and methods described herein may further use or incorporated the systems and methods described in U.S. Pat. No. 9,764,143 issued Sep. 19, 2017, U.S. Pat. No. 9,586,050 issued Mar. 7, 2017, U.S. Pat. No. 9,586,052 issued Mar. 7, 2017, all of which are incorporated herein by reference in their entireties.

The exemplary systems, methods, and graphical user interfaces described herein may be used with respect to the implantation and configuration of an implantable medical device (IMD) and/or one or more leads configured to be located proximate one or more portions of a patient's heart. For example, the exemplary systems, methods, and interfaces may be used in conjunction with an exemplary therapy system 10 described herein with reference to FIGS. 9-11.

FIG. 9 is a conceptual diagram illustrating an exemplary therapy system 10 that may be used to deliver pacing therapy to a patient 14. Patient 14 may, but not necessarily, be a human. The therapy system 10 may include an implantable medical device 16 (IMD), which may be coupled to leads 18, 20, 22. The IMD 16 may be, e.g., an implantable pacemaker, cardioverter, and/or defibrillator, that delivers, or provides, electrical signals (e.g., paces, etc.) to and/or senses electrical signals from the heart 12 of the patient 14 via electrodes coupled to one or more of the leads 18, 20, 22.

The leads 18, 20, 22 extend into the heart 12 of the patient 14 to sense electrical activity of the heart 12 and/or to deliver electrical stimulation to the heart 12. In the example shown in FIG. 9, the right ventricular (RV) lead 18 extends through one or more veins (not shown), the superior vena cava (not shown), and the right atrium 26, and into the right ventricle 28. The left ventricular (LV) coronary sinus lead 20 extends through one or more veins, the vena cava, the right atrium 26, and into the coronary sinus 30 to a region adjacent to the free wall of the left ventricle 32 of the heart 12. The right atrial (RA) lead 22 extends through one or more veins and the vena cava, and into the right atrium 26 of the heart 12.

The IMD 16 may sense, among other things, electrical signals attendant to the depolarization and repolarization of the heart 12 via electrodes coupled to at least one of the leads 18, 20, 22. In some examples, the IMD 16 provides pacing therapy (e.g., pacing pulses) to the heart 12 based on the electrical signals sensed within the heart 12. The IMD 16 may be operable to adjust one or more parameters associated with the pacing therapy such as, e.g., AV delay and other various timings, pulse wide, amplitude, voltage, burst length, etc. Further, the IMD 16 may be operable to use various electrode configurations to deliver pacing therapy, which may be unipolar, bipolar, quadripolar, or further multipolar. For example, a multipolar lead may include several electrodes that can be used for delivering pacing therapy. Hence, a multipolar lead system may provide, or offer, multiple electrical vectors to pace from. A pacing vector may include at least one cathode, which may be at least one electrode located on at least one lead, and at least one anode, which may be at least one electrode located on at least one lead (e.g., the same lead, or a different lead) and/or on the casing, or can, of the IMD 16. While improvement in cardiac function as a result of the pacing therapy may primarily depend on the cathode, the electrical parameters like impedance, pacing threshold voltage, current drain, longevity, etc. may be more dependent on the pacing vector, which includes both the cathode and the anode. The IMD 16 may also provide defibrillation therapy and/or cardioversion therapy via electrodes located on at least one of the leads 18, 20, 22. Further, the IMD 16 may detect arrhythmia of the heart 12, such as fibrillation of the ventricles 28, 32, and deliver defibrillation therapy to the heart 12 in the form of electrical pulses. In some examples, IMD 16 may be programmed to deliver a progression of therapies, e.g., pulses with increasing energy levels, until a fibrillation of heart 12 is stopped.

Figure 10A:
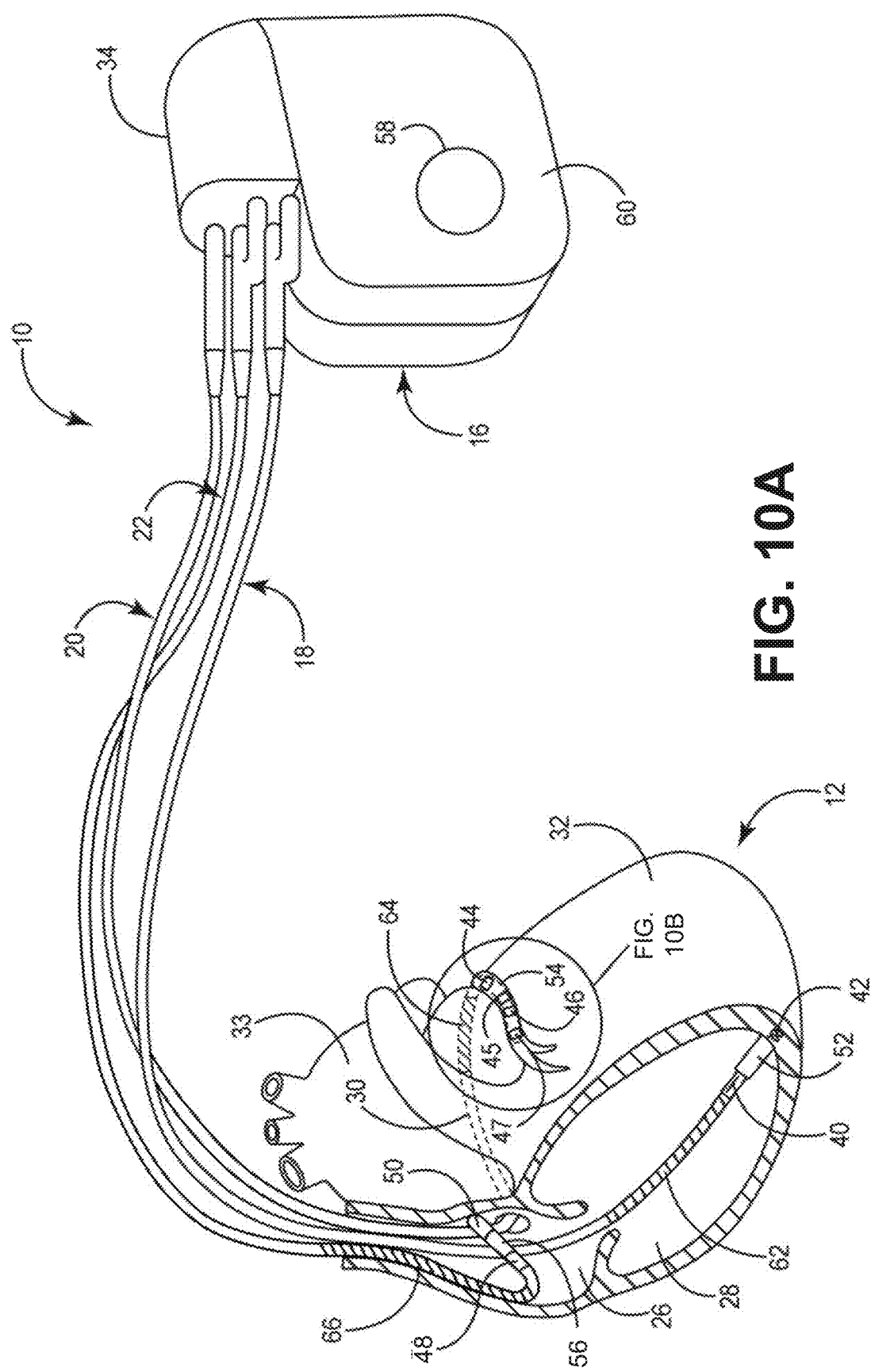
FIG. 10A is a diagram of the exemplary IMD of FIG. 9.
Figure 10B:
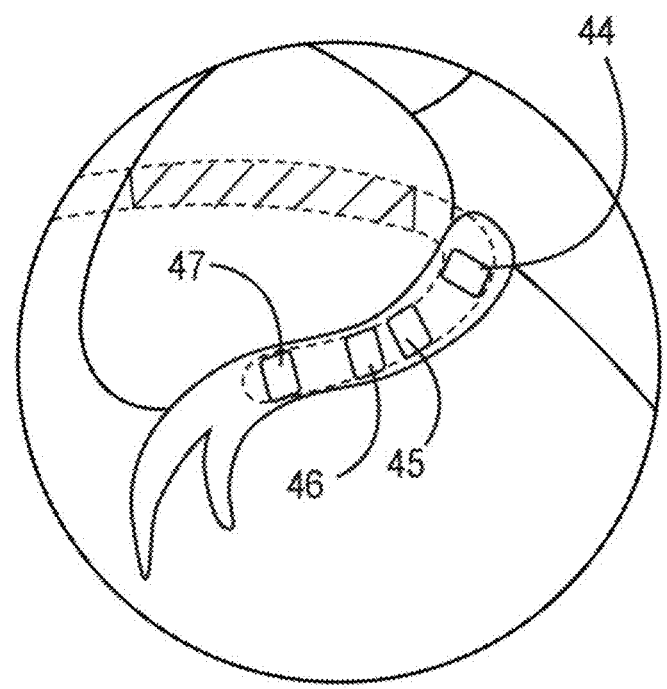
FIG. 10B is a diagram of an enlarged view of a distal end of the electrical lead disposed in the left ventricle of FIG. 10A.

FIGS. 10A-10B are conceptual diagrams illustrating the IMD 16 and the leads 18, 20, 22 of therapy system 10 of FIG. 9 in more detail. The leads 18, 20, 22 may be electrically coupled to a therapy delivery module (e.g., for delivery of pacing therapy), a sensing module (e.g., for sensing one or more signals from one or more electrodes), and/or any other modules of the IMD 16 via a connector block 34. In some examples, the proximal ends of the leads 18, 20, 22 may include electrical contacts that electrically couple to respective electrical contacts within the connector block 34 of the IMD 16. In addition, in some examples, the leads 18, 20, 22 may be mechanically coupled to the connector block 34 with the aid of set screws, connection pins, or another suitable mechanical coupling mechanism.

Each of the leads 18, 20, 22 includes an elongated insulative lead body, which may carry a number of conductors (e.g., concentric coiled conductors, straight conductors, etc.) separated from one another by insulation (e.g., tubular insulative sheaths). In the illustrated example, bipolar electrodes 40, 42 are located proximate to a distal end of the lead 18. In addition, bipolar electrodes 44, 45, 46, 47 are located proximate to a distal end of the lead 20 and bipolar electrodes 48, 50 are located proximate to a distal end of the lead 22.

The electrodes 40, 44, 45, 46, 47, 48 may take the form of ring electrodes, and the electrodes 42, 50 may take the form of extendable helix tip electrodes mounted retractably within the insulative electrode heads 52, 54, 56, respectively. Each of the electrodes 40, 42, 44, 45, 46, 47, 48, 50 may be electrically coupled to a respective one of the conductors (e.g., coiled and/or straight) within the lead body of its associated lead 18, 20, 22, and thereby coupled to a respective one of the electrical contacts on the proximal end of the leads 18, 20, 22.

Additionally, electrodes 44, 45, 46 and 47 may have an electrode surface area of about 5.3 mm$^2$ to about 5.8 mm$^2$. Electrodes 44, 45, 46, and 47 may also be referred to as LV1, LV2, LV3, and LV4, respectively. The LV electrodes (i.e., left ventricle electrode 1 (LV1) 44, left ventricle electrode 2 (LV2) 45, left ventricle electrode 3 (LV3) 46, and left ventricle 4 (LV4) 47 etc.) on the lead 20 can be spaced apart at variable distances. For example, electrode 44 may be a distance of, e.g., about 21 millimeters (mm), away from electrode 45, electrodes 45 and 46 may be spaced a distance of, e.g. about 1.3 mm to about 1.5 mm, away from each other, and electrodes 46 and 47 may be spaced a distance of, e.g. 20 mm to about 21 mm, away from each other.

The electrodes 40, 42, 44, 45, 46, 47, 48, 50 may further be used to sense electrical signals (e.g., morphological waveforms within electrograms (EGM)) attendant to the depolarization and repolarization of the heart 12. The electrical signals are conducted to the IMD 16 via the respective leads 18, 20, 22. In some examples, the IMD 16 may also deliver pacing pulses via the electrodes 40, 42, 44, 45, 46, 47, 48, 50 to cause depolarization of cardiac tissue of the patient's heart 12. In some examples, as illustrated in FIG. 10A, the IMD 16 includes one or more housing electrodes, such as housing electrode 58, which may be formed integrally with an outer surface of a housing 60 (e.g., hermetically-sealed housing) of the IMD 16 or otherwise coupled to the housing 60. Any of the electrodes 40, 42, 44, 45, 46, 47, 48, 50 may be used for unipolar sensing or pacing in combination with the housing electrode 58. It is generally understood by those skilled in the art that other electrodes can also be selected to define, or be used for, pacing and sensing vectors. Further, any of electrodes 40, 42, 44, 45, 46, 47, 48, 50, 58, when not being used to deliver pacing therapy, may be used to sense electrical activity during pacing therapy.

As described in further detail with reference to FIG. 10A, the housing 60 may enclose a therapy delivery module that may include a stimulation generator for generating cardiac pacing pulses and defibrillation or cardioversion shocks, as well as a sensing module for monitoring the electrical signals of the patient's heart (e.g., the patient's heart rhythm). The leads 18, 20, 22 may also include elongated electrodes 62, 64, 66, respectively, which may take the form of a coil. The IMD 16 may deliver defibrillation shocks to the heart 12 via any combination of the elongated electrodes 62, 64, 66 and the housing electrode 58. The electrodes 58, 62, 64, 66 may also be used to deliver cardioversion pulses to the heart 12. Further, the electrodes 62, 64, 66 may be fabricated from any suitable electrically conductive material, such as, but not limited to, platinum, platinum alloy, and/or other materials known to be usable in implantable defibrillation electrodes. Since electrodes 62, 64, 66 are not generally configured to deliver pacing therapy, any of electrodes 62, 64, 66 may be used to sense electrical activity and may be used in combination with any of electrodes 40, 42, 44, 45, 46, 47, 48, 50, 58. In at least one embodiment, the RV elongated electrode 62 may be used to sense electrical activity of a patient's heart during the delivery of pacing therapy (e.g., in combination with the housing electrode 58, or defibrillation electrode-to-housing electrode vector).

The configuration of the exemplary therapy system 10 illustrated in FIGS. 9-11 is merely one example. In other examples, the therapy system may include epicardial leads and/or patch electrodes instead of or in addition to the transvenous leads 18, 20, 22 illustrated in FIG. 9. Additionally, in other examples, the therapy system 10 may be implanted in/around the cardiac space without transvenous leads (e.g., leadless/wireless pacing systems) or with leads implanted (e.g., implanted transvenously or using approaches) into the left chambers of the heart (in addition to or replacing the transvenous leads placed into the right chambers of the heart as illustrated in FIG. 9). Further, in one or more embodiments, the IMD 16 need not be implanted within the patient 14. For example, the IMD 16 may deliver various cardiac therapies to the heart 12 via percutaneous leads that extend through the skin of the patient 14 to a variety of positions within or outside of the heart 12. In one or more embodiments, the system 10 may utilize wireless pacing (e.g., using energy transmission to the intracardiac pacing component(s) via ultrasound, inductive coupling, RF, etc.) and sensing cardiac activation using electrodes on the can/housing and/or on subcutaneous leads.

In other examples of therapy systems that provide electrical stimulation therapy to the heart 12, such therapy systems may include any suitable number of leads coupled to the IMD 16, and each of the leads may extend to any location within or proximate to the heart 12. For example, other examples of therapy systems may include three transvenous leads located as illustrated in FIGS. 9-11. Still further, other therapy systems may include a single lead that extends from the IMD 16 into the right atrium 26 or the right ventricle 28, or two leads that extend into a respective one of the right atrium 26 and the right ventricle 28.

Figure 11A:
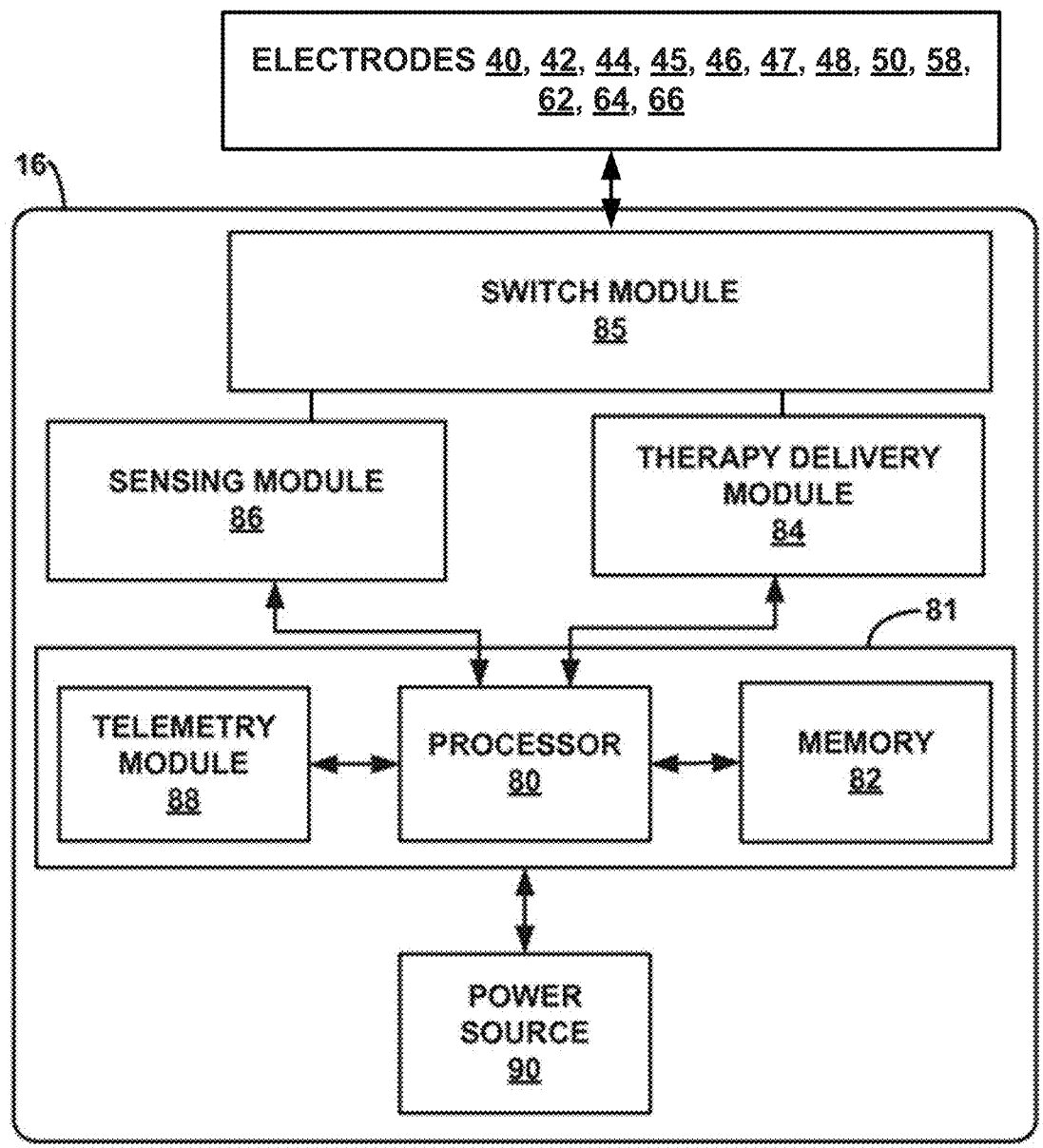
FIG. 11A is a block diagram of an exemplary IMD, e.g., of the systems of FIGS. 9-10.

FIG. 11A is a functional block diagram of one exemplary configuration of the IMD 16. As shown, the IMD 16 may include a control module 81, a therapy delivery module 84 (e.g., which may include a stimulation generator), a sensing module 86, and a power source 90.

The control module 81 may include a processor 80, memory 82, and a telemetry module 88. The memory 82 may include computer-readable instructions that, when executed, e.g., by the processor 80, cause the IMD 16 and/or the control module 81 to perform various functions attributed to the IMD 16 and/or the control module 81 described herein. Further, the memory 82 may include any volatile, non-volatile, magnetic, optical, and/or electrical media, such as a random-access memory (RAM), read-only memory (ROM), non-volatile RAM (NVRAM), electrically-erasable programmable ROM (EEPROM), flash memory, and/or any other digital media. An exemplary capture management module may be the left ventricular capture management (LVCM) module described in U.S. Pat. No. 7,684,863 entitled "LV THRESHOLD MEASUREMENT AND CAPTURE MANAGEMENT" and issued Mar. 23, 2010, which is incorporated herein by reference in its entirety.

The processor, or processing circuitry, 80 of the control module 81 may include any one or more of a microprocessor, a controller, a digital signal processor (DSP), an application specific integrated circuit (ASIC), a field-programmable gate array (FPGA), and/or equivalent discrete or integrated logic circuitry. In some examples, the processor, or processing circuitry, 80 may include multiple components, such as any combination of one or more microprocessors, one or more controllers, one or more DSPs, one or more ASICs, and/or one or more FPGAs, as well as other discrete or integrated logic circuitry. The functions attributed to the processor 80 herein may be embodied as software, firmware, hardware, or any combination thereof.

The control module 81 may control the therapy delivery module 84 to deliver therapy (e.g., electrical stimulation therapy such as pacing) to the heart 12 according to a selected one or more therapy programs, which may be stored in the memory 82. More, specifically, the control module 81 (e.g., the processor 80) may control various parameters of the electrical stimulus delivered by the therapy delivery module 84 such as, e.g., AV delays, VV delays, pacing pulses with the amplitudes, pulse widths, frequency, or electrode polarities, etc., which may be specified by one or more selected therapy programs (e.g., AV and/or VV delay adjustment programs, pacing therapy programs, pacing recovery programs, capture management programs, etc.). As shown, the therapy delivery module 84 is electrically coupled to electrodes 40, 42, 44, 45, 46, 47, 48, 50, 58, 62, 64, 66, e.g., via conductors of the respective lead 18, 20, 22, or, in the case of housing electrode 58, via an electrical conductor disposed within housing 60 of IMD 16. Therapy delivery module 84 may be configured to generate and deliver electrical stimulation therapy such as pacing therapy to the heart 12 using one or more of the electrodes 40, 42, 44, 45, 46, 47, 48, 50, 58, 62, 64, 66.

For example, therapy delivery module 84 may deliver pacing stimulus (e.g., pacing pulses) via ring electrodes 40, 44, 45, 46, 47, 48 coupled to leads 18, 20, 22 and/or helical tip electrodes 42, 50 of leads 18, 22. Further, for example, therapy delivery module 84 may deliver defibrillation shocks to heart 12 via at least two of electrodes 58, 62, 64, 66. In some examples, therapy delivery module 84 may be configured to deliver pacing, cardioversion, or defibrillation stimulation in the form of electrical pulses. In other examples, therapy delivery module 84 may be configured deliver one or more of these types of stimulation in the form of other signals, such as sine waves, square waves, and/or other substantially continuous time signals.

The IMD 16 may further include a switch module 85 and the control module 81 (e.g., the processor 80) may use the switch module 85 to select, e.g., via a data/address bus, which of the available electrodes are used to deliver therapy such as pacing pulses for pacing therapy, or which of the available electrodes are used for sensing. The switch module 85 may include a switch array, switch matrix, multiplexer, or any other type of switching device suitable to selectively couple the sensing module 86 and/or the therapy delivery module 84 to one or more selected electrodes. More specifically, the therapy delivery module 84 may include a plurality of pacing output circuits. Each pacing output circuit of the plurality of pacing output circuits may be selectively coupled, e.g., using the switch module 85, to one or more of the electrodes 40, 42, 44, 45, 46, 47, 48, 50, 58, 62, 64, 66 (e.g., a pair of electrodes for delivery of therapy to a bipolar or multipolar pacing vector). In other words, each electrode can be selectively coupled to one of the pacing output circuits of the therapy delivery module using the switching module 85.

The sensing module 86 is coupled (e.g., electrically coupled) to sensing apparatus, which may include, among additional sensing apparatus, the electrodes 40, 42, 44, 45, 46, 47, 48, 50, 58, 62, 64, 66 to monitor electrical activity of the heart 12, e.g., electrocardiogram (ECG)/electrogram (EGM) signals, etc. The ECG/EGM signals may be used to measure or monitor activation times (e.g., ventricular activations times, etc.), heart rate (HR), heart rate variability (HRV), heart rate turbulence (HRT), deceleration/acceleration capacity, deceleration sequence incidence, T-wave alternans (TWA), P-wave to P-wave intervals (also referred to as the P-P intervals or A-A intervals), R-wave to R-wave intervals (also referred to as the R-R intervals or V-V intervals), P-wave to QRS complex intervals (also referred to as the P-R intervals, A-V intervals, or P-Q intervals), QRS-complex morphology, ST segment (i.e., the segment that connects the QRS complex and the T-wave), T-wave changes, QT intervals, electrical vectors, etc.

The switch module 85 may also be used with the sensing module 86 to select which of the available electrodes are used, or enabled, to, e.g., sense electrical activity of the patient's heart (e.g., one or more electrical vectors of the patient's heart using any combination of the electrodes 40, 42, 44, 45, 46, 47, 48, 50, 58, 62, 64, 66). Likewise, the switch module 85 may also be used with the sensing module 86 to select which of the available electrodes are not to be used (e.g., disabled) to, e.g., sense electrical activity of the patient's heart (e.g., one or more electrical vectors of the patient's heart using any combination of the electrodes 40, 42, 44, 45, 46, 47, 48, 50, 58, 62, 64, 66), etc. In some examples, the control module 81 may select the electrodes that function as sensing electrodes via the switch module within the sensing module 86, e.g., by providing signals via a data/address bus.

In some examples, sensing module 86 includes a channel that includes an amplifier with a relatively wider pass band than the R-wave or P-wave amplifiers. Signals from the selected sensing electrodes may be provided to a multiplexer, and thereafter converted to multi-bit digital signals by an analog-to-digital converter for storage in memory 82, e.g., as an electrogram (EGM). In some examples, the storage of such EGMs in memory 82 may be under the control of a direct memory access circuit.

In some examples, the control module 81 may operate as an interrupt driven device, and may be responsive to interrupts from pacer timing and control module, where the interrupts may correspond to the occurrences of sensed P-waves and R-waves and the generation of cardiac pacing pulses. Any necessary mathematical calculations may be performed by the processor 80 and any updating of the values or intervals controlled by the pacer timing and control module may take place following such interrupts. A portion of memory 82 may be configured as a plurality of recirculating buffers, capable of holding one or more series of measured intervals, which may be analyzed by, e.g., the processor 80 in response to the occurrence of a pace or sense interrupt to determine whether the patient's heart 12 is presently exhibiting atrial or ventricular tachyarrhythmia.

The telemetry module 88 of the control module 81 may include any suitable hardware, firmware, software, or any combination thereof for communicating with another device, such as a programmer. For example, under the control of the processor 80, the telemetry module 88 may receive downlink telemetry from and send uplink telemetry to a programmer with the aid of an antenna, which may be internal and/or external. The processor 80 may provide the data to be uplinked to a programmer and the control signals for the telemetry circuit within the telemetry module 88, e.g., via an address/data bus. In some examples, the telemetry module 88 may provide received data to the processor 80 via a multiplexer.

The various components of the IMD 16 are further coupled to a power source 90, which may include a rechargeable or non-rechargeable battery. A non-rechargeable battery may be selected to last for several years, while a rechargeable battery may be inductively charged from an external device, e.g., on a daily or weekly basis.

Figure 11B:
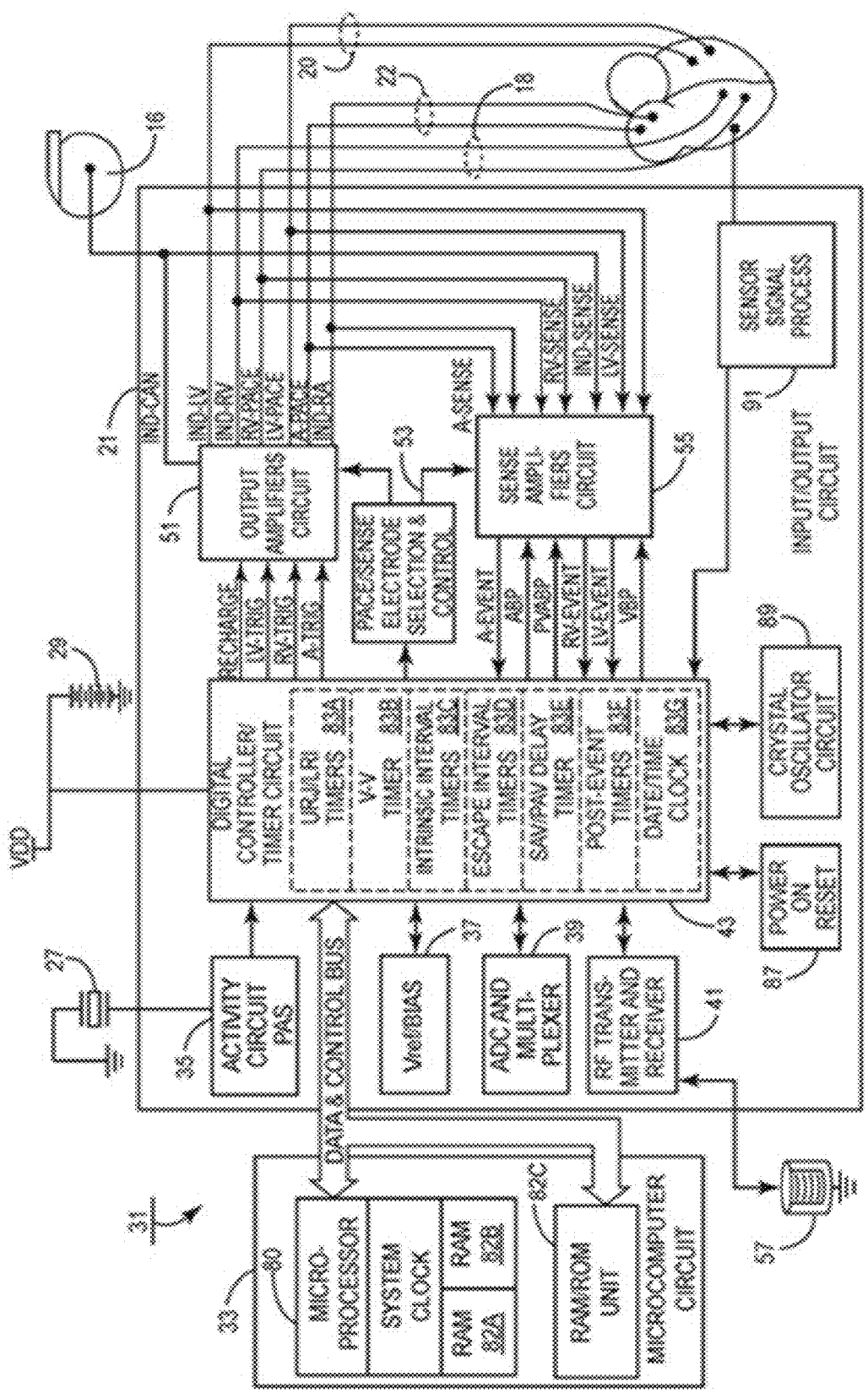
FIG. 11B is another block diagram of an exemplary IMD (e.g., an implantable pulse generator) circuitry and associated leads employed in the systems of FIGS. 9-10.

FIG. 11B is another embodiment of a functional block diagram for IMD 16 that depicts bipolar RA lead 22, bipolar RV lead 18, and bipolar LV CS lead 20 without the LA CS pace/sense electrodes and coupled with an implantable pulse generator (IPG) circuit 31 having programmable modes and parameters of a biventricular DDD/R type known in the pacing art. In turn, the sensor signal processing circuit 91 indirectly couples to the timing circuit 43 and via data and control bus to microcomputer circuitry 33. The IPG circuit 31 is illustrated in a functional block diagram divided generally into a microcomputer circuit 33 and a pacing circuit 21. The pacing circuit 21 includes the digital controller/timer circuit 43, the output amplifiers circuit 51, the sense amplifiers circuit 55, the RF telemetry transceiver 41, the activity sensor circuit 35 as well as a number of other circuits and components described below.

Crystal oscillator circuit 89 provides the basic timing clock for the pacing circuit 21 while battery 29 provides power. Power-on-reset circuit 87 responds to initial connection of the circuit to the battery for defining an initial operating condition and similarly, resets the operative state of the device in response to detection of a low battery condition. Reference mode circuit 37 generates stable voltage reference and currents for the analog circuits within the pacing circuit 21. Analog-to-digital converter (ADC) and multiplexer circuit 39 digitize analog signals and voltage to provide, e.g., real time telemetry of cardiac signals from sense amplifiers 55 for uplink transmission via RF transmitter and receiver circuit 41. Voltage reference and bias circuit 37, ADC and multiplexer 39, power-on-reset circuit 87, and crystal oscillator circuit 89 may correspond to any of those used in exemplary implantable cardiac pacemakers.

If the IPG is programmed to a rate responsive mode, the signals output by one or more physiologic sensors are employed as a rate control parameter (RCP) to derive a physiologic escape interval. For example, the escape interval is adjusted proportionally to the patient's activity level developed in the patient activity sensor (PAS) circuit 35 in the depicted, exemplary IPG circuit 31. The patient activity sensor 27 is coupled to the IPG housing and may take the form of a piezoelectric crystal transducer. The output signal of the patient activity sensor 27 may be processed and used as a RCP. Sensor 27 generates electrical signals in response to sensed physical activity that are processed by activity circuit 35 and provided to digital controller/timer circuit 43. Activity circuit 35 and associated sensor 27 may correspond to the circuitry disclosed in U.S. Pat. No. 5,052,388 entitled "METHOD AND APPARATUS FOR IMPLEMENTING ACTIVITY SENSING IN A PULSE GENERATOR" and issued on Oct. 1, 1991 and U.S. Pat. No. 4,428,378 entitled "RATE ADAPTIVE PACER" and issued on Jan. 31, 1984, each of which is incorporated herein by reference in its entirety. Similarly, the exemplary systems, apparatus, and methods described herein may be practiced in conjunction with alternate types of sensors such as oxygenation sensors, pressure sensors, pH sensors, and respiration sensors, for use in providing rate responsive pacing capabilities. Alternately, QT time may be used as a rate indicating parameter, in which case no extra sensor is required. Similarly, the exemplary embodiments described herein may also be practiced in non-rate responsive pacemakers.

Data transmission to and from the external programmer is accomplished by way of the telemetry antenna 57 and an associated RF transceiver 41, which serves both to demodulate received downlink telemetry and to transmit uplink telemetry. Uplink telemetry capabilities may include the ability to transmit stored digital information, e.g., operating modes and parameters, EGM histograms, and other events, as well as real time EGMs of atrial and/or ventricular electrical activity and marker channel pulses indicating the occurrence of sensed and paced depolarizations in the atrium and ventricle.

Microcomputer 33 contains a microprocessor 80 and associated system clock and on-processor RAM and ROM chips 82A and 82B, respectively. In addition, microcomputer circuit 33 includes a separate RAM/ROM chip 82C to provide additional memory capacity. Microprocessor 80 normally operates in a reduced power consumption mode and is interrupt driven. Microprocessor 80 is awakened in response to defined interrupt events, which may include A-TRIG, RV-TRIG, LV-TRIG signals generated by timers in digital timer/controller circuit 43 and A-EVENT, RV-EVENT, and LV-EVENT signals generated by sense amplifiers circuit 55, among others. The specific values of the intervals and delays timed out by digital controller/timer circuit 43 are controlled by the microcomputer circuit 33 by way of data and control bus from programmed-in parameter values and operating modes. In addition, if programmed to operate as a rate responsive pacemaker, a timed interrupt, e.g., every cycle or every two seconds, may be provided in order to allow the microprocessor to analyze the activity sensor data and update the basic A-A, V-A, or V-V escape interval, as applicable. In addition, the microprocessor 80 may also serve to define variable, operative AV delay intervals, V-V delay intervals, and the energy delivered to each ventricle and/or atrium.

In one embodiment, microprocessor 80 is a custom microprocessor adapted to fetch and execute instructions stored in RAM/ROM unit 82 in a conventional manner. It is contemplated, however, that other implementations may be suitable to practice the present invention. For example, an off-the-shelf, commercially available microprocessor or microcontroller, or custom application-specific, hardwired logic, or state-machine type circuit may perform the functions of microprocessor 80.

Digital controller/timer circuit 43 operates under the general control of the microcomputer 33 to control timing and other functions within the pacing circuit 21 and includes a set of timing and associated logic circuits of which certain ones pertinent to the present invention are depicted. The depicted timing circuits include URI/LRI timers 83A, V-V delay timer 83B, intrinsic interval timers 83C for timing elapsed V-EVENT to V-EVENT intervals or V-EVENT to A-EVENT intervals or the V-V conduction interval, escape interval timers 83D for timing A-A, V-A, and/or V-V pacing escape intervals, an AV delay interval timer 83E for timing the A-LVp delay (or A-RVp delay) from a preceding A-EVENT or A-TRIG, a post-ventricular timer 83F for timing post-ventricular time periods, and a date/time clock 83G.

The AV delay interval timer 83E is loaded with an appropriate delay interval for one ventricular chamber (e.g., either an A-RVp delay or an A-LVp) to time-out starting from a preceding A-PACE or A-EVENT. The interval timer 83E triggers pacing stimulus delivery, and can be based on one or more prior cardiac cycles (or from a data set empirically derived for a given patient).

The post-event timer 83F times out the post-ventricular time period following an RV-EVENT or LV-EVENT or a RV-TRIG or LV-TRIG and post-atrial time periods following an A-EVENT or A-TRIG. The durations of the post-event time periods may also be selected as programmable parameters stored in the microcomputer 33. The post-ventricular time periods include the PVARP, a post-atrial ventricular blanking period (PAVBP), a ventricular blanking period (VBP), a post-ventricular atrial blanking period (PVARP) and a ventricular refractory period (VRP) although other periods can be suitably defined depending, at least in part, on the operative circuitry employed in the pacing engine. The post-atrial time periods include an atrial refractory period (ARP) during which an A-EVENT is ignored for the purpose of resetting any AV delay, and an atrial blanking period (ABP) during which atrial sensing is disabled. It should be noted that the starting of the post-atrial time periods and the AV delays can be commenced substantially simultaneously with the start or end of each A-EVENT or A-TRIG or, in the latter case, upon the end of the A-PACE which may follow the A-TRIG. Similarly, the starting of the post-ventricular time periods and the V-A escape interval can be commenced substantially simultaneously with the start or end of the V-EVENT or V-TRIG or, in the latter case, upon the end of the V-PACE which may follow the V-TRIG. The microprocessor 80 also optionally calculates AV delays, VV delays, post-ventricular time periods, and post-atrial time periods that vary with the sensor based escape interval established in response to the RCP(s) and/or with the intrinsic atrial and/or ventricular rate.

The output amplifiers circuit 51 contains a RA pace pulse generator (and a LA pace pulse generator if LA pacing is provided), a RV pace pulse generator, a LV pace pulse generator, and/or any other pulse generator configured to provide atrial and ventricular pacing. In order to trigger generation of an RV-PACE or LV-PACE pulse, digital controller/timer circuit 43 generates the RV-TRIG signal at the time-out of the A-RVp delay (in the case of RV pre-excitation) or the LV-TRIG at the time-out of the A-LVp delay (in the case of LV pre-excitation) provided by AV delay interval timer 83E (or the V-V delay timer 83B). Similarly, digital controller/timer circuit 43 generates an RA-TRIG signal that triggers output of an RA-PACE pulse (or an LA-TRIG signal that triggers output of an LA-PACE pulse, if provided) at the end of the V-A escape interval timed by escape interval timers 83D.

The output amplifiers circuit 51 includes switching circuits for coupling selected pace electrode pairs from among the lead conductors and the IND-CAN electrode 20 to the RA pace pulse generator (and LA pace pulse generator if provided), RV pace pulse generator and LV pace pulse generator. Pace/sense electrode pair selection and control circuit 53 selects lead conductors and associated pace electrode pairs to be coupled with the atrial and ventricular output amplifiers within output amplifiers circuit 51 for accomplishing RA, LA, RV and LV pacing.

The sense amplifiers circuit 55 contains sense amplifiers for atrial and ventricular pacing and sensing. High impedance P-wave and R-wave sense amplifiers may be used to amplify a voltage difference signal that is generated across the sense electrode pairs by the passage of cardiac depolarization wavefronts. The high impedance sense amplifiers use high gain to amplify the low amplitude signals and rely on pass band filters, time domain filtering and amplitude threshold comparison to discriminate a P-wave or R-wave from background electrical noise. Digital controller/timer circuit 43 controls sensitivity settings of the atrial and ventricular sense amplifiers 55.

The sense amplifiers may be uncoupled from the sense electrodes during the blanking periods before, during, and after delivery of a pace pulse to any of the pace electrodes of the pacing system to avoid saturation of the sense amplifiers. The sense amplifiers circuit 55 includes blanking circuits for uncoupling the selected pairs of the lead conductors and the IND-CAN electrode 20 from the inputs of the RA sense amplifier (and LA sense amplifier if provided), RV sense amplifier and LV sense amplifier during the ABP, PVABP and VBP. The sense amplifiers circuit 55 also includes switching circuits for coupling selected sense electrode lead conductors and the IND-CAN electrode 20 to the RA sense amplifier (and LA sense amplifier if provided), RV sense amplifier and LV sense amplifier. Again, sense electrode selection and control circuit 53 selects conductors and associated sense electrode pairs to be coupled with the atrial and ventricular sense amplifiers within the output amplifiers circuit 51 and sense amplifiers circuit 55 for accomplishing RA, LA, RV, and LV sensing along desired unipolar and bipolar sensing vectors.

Right atrial depolarizations or P-waves in the RA-SENSE signal that are sensed by the RA sense amplifier result in a RA-EVENT signal that is communicated to the digital controller/timer circuit 43. Similarly, left atrial depolarizations or P-waves in the LA-SENSE signal that are sensed by the LA sense amplifier, if provided, result in a LA-EVENT signal that is communicated to the digital controller/timer circuit 43. Ventricular depolarizations or R-waves in the RV-SENSE signal are sensed by a ventricular sense amplifier result in an RV-EVENT signal that is communicated to the digital controller/timer circuit 43. Similarly, ventricular depolarizations or R-waves in the LV-SENSE signal are sensed by a ventricular sense amplifier result in an LV-EVENT signal that is communicated to the digital controller/timer circuit 43. The RV-EVENT, LV-EVENT, and RA-EVENT, LA-SENSE signals may be refractory or non-refractory, and can inadvertently be triggered by electrical noise signals or aberrantly conducted depolarization waves rather than true R-waves or P-waves.

The techniques described in this disclosure, including those attributed to the IMD 16, the computing apparatus 140, and/or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices, or other devices. The term "module," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by processing circuitry and/or one or more processors to support one or more aspects of the functionality described in this disclosure.

ILLUSTRATIVE EMBODIMENTS

Embodiment 1

A system for use in cardiac evaluation comprising:
electrode apparatus comprising a plurality of external electrodes to be located proximate a patient's skin, wherein the plurality of external electrodes comprises:
a posterior set of electrodes located proximate the patient's posterior, and an anterior set of electrodes located proximate the patient's anterior; and
computing apparatus comprising one or more processors, the computing apparatus operably coupled to the electrode apparatus and configured to:
monitor electrical activity from the patient's skin using the plurality of external electrodes over a cardiac cycle resulting in a posterior set of electrode signals monitored from one or more of the posterior set of electrodes and an anterior set of electrode signals monitored from one or more of the anterior set of electrodes, and
compare the morphology of the anterior set of electrode signals and the morphology of the posterior set of electrode signals to assist in determination of electrical heterogeneity.

Embodiment 2

The system as set forth embodiment 1, wherein comparing the morphology of the anterior set of electrode signals and the morphology of the posterior set of electrode signals comprises determining whether the morphology of the posterior set of electrode signals is similar to the morphology of the anterior set of electrode signals.

Embodiment 3

The system as set forth in any one of embodiments 1-2, wherein comparing the morphology of the anterior set of electrode signals and the morphology of the posterior set of electrode signals comprises determining whether the morphology of the posterior set of electrode signals is predominately opposite the morphology of the anterior set of electrode signals.

Embodiment 4

The system as set forth in any one of embodiments 1-3, wherein the computing apparatus is further configured to determine an activation time of the QRS complex of the cardiac cycle for each electrode signal of the anterior set of electrode signals and the posterior set of electrode signals, wherein comparing the morphology of the anterior set of electrode signals and the morphology of the posterior set of electrode signals comprises comparing the activation times of the anterior set of electrode signals and the activation times of the posterior set of electrode signals.

Embodiment 5

The system as set forth in any one of embodiments 1-4, wherein the computing apparatus is further configured to determine an amplitude of the QRS complex of the cardiac cycle for each electrode signal of the anterior set of electrode signals and the posterior set of electrode signals, wherein comparing the morphology of the anterior set of electrode signals and the morphology of the posterior set of electrode signals comprises comparing the amplitudes of the anterior set of electrode signals and the amplitudes of the posterior set of electrode signals.

Embodiment 6

The system as set forth in any one of embodiments 1-5, wherein comparing the morphology of the anterior set of electrode signals and the morphology of the posterior set of electrode signals comprises determining a metric of electrical heterogeneity comparing the anterior set of electrode signals and the posterior set of electrode signals, wherein the metric of electrical heterogeneity comprises at least one of:
ventricular electrical uncoupling metric based in a difference between an average of activation times of the posterior set of electrode signals and an average of activation times of the anterior set of electrode signals;
composite area under the curve metric based on of the area under the curve of the anterior set of electrode signals and the area under the curve of the posterior set of electrode signals;
composite height metric based on the maximum heights of each of the anterior set of electrode signals and the maximum heights of each of the posterior set of electrode signals; and
composite inter-activation event activation distance based on the distance between each activation time of the anterior set of electrode signals and each activation time of the posterior set of electrode signals.

Embodiment 7

The system as set forth in any one of embodiments 1-6, the system further comprising a display comprising a graphical user interface to present cardiac signal information, wherein the computing apparatus is further configured to:
initiate cardiac therapy to the patient applying a plurality of different cardiac therapy settings over a plurality of cardiac cycles; and
display on the graphical user interface a plurality of single-cycle graphs, each single-cycle graph corresponding to a different cardiac cycle where different cardiac therapy settings are applied, each single-cycle graph including all of the posterior set of electrode signals and the anterior set of electrode signals.

Embodiment 8

The system as set forth in embodiment 7, wherein comparing the anterior set of electrode signals and the posterior set of electrode signals comprises determining a metric of electrical heterogeneity based on the anterior set of electrode signals and the posterior set of electrode signals for each different cardiac cycle where different cardiac therapy settings are applied, wherein the computing apparatus is further configured to display the metric of electrical heterogeneity for each different cardiac cycle where different cardiac therapy settings are applied proximate the corresponding single-cycle graph, wherein the metric of electrical heterogeneity comprises at least one of:

ventricular electrical uncoupling metric based in a difference between an average of activation times of the posterior set of electrode signals and an average of activation times of the anterior set of electrode signals;

composite area under the curve metric based on of the area under the curve of the anterior set of electrode signals and the area under the curve of the posterior set of electrode signals;

composite height metric based on the maximum heights of each of the anterior set of electrode signals and the maximum heights of each of the posterior set of electrode signals; and composite inter-activation event activation distance based on the distance between each activation time of the anterior set of electrode signals and each activation time of the posterior set of electrode signals.

Embodiment 9

The system as set forth in any one of embodiments 7-8, wherein the plurality of different cardiac settings comprises one or more of selection between intrinsic rhythm, left ventricular-only pacing and biventricular pacing, V-V pacing delay, and A-V pacing delay.

Embodiment 10

The system as set forth in any one of embodiments 7-9, wherein the computing apparatus is further configured to:

determine effective cardiac settings of the plurality of different cardiac therapy settings based the posterior set of electrode signals and the anterior set of electrodes; and indicate a desired single-cycle graph of the plurality of single-cycle graphs on the graphical user interface that corresponds to the determined effective cardiac settings.

Embodiment 11

The system as set forth in any one of embodiments 1-9, wherein the computing apparatus is further configured to:

initiate cardiac therapy to the patient applying a plurality of different cardiac therapy settings over a plurality of cardiac cycles; and determine effective cardiac settings of the plurality of different cardiac therapy settings based on the posterior set of electrode signals and the anterior set of electrodes.

Embodiment 12

A method for use in cardiac evaluation comprising:

monitoring electrical activity from a patient's skin using a plurality of external electrodes over a cardiac cycle resulting in a posterior set of electrode signals monitored from one or more of posterior set of electrodes located proximate the patient's posterior and an anterior set of electrode signals monitored from one or more of an anterior set of electrodes located proximate the patient's anterior; and comparing the morphology of the anterior set of electrode signals and the morphology of the posterior set of electrode signals to assist in determination of electrical heterogeneity.

Embodiment 13

The method as set forth in embodiment 12, wherein comparing the morphology of the anterior set of electrode signals and the morphology of the posterior set of electrode signals comprises determining whether the morphology of the posterior set of electrode signals is similar to the morphology of the anterior set of electrode signals.

Embodiment 14

The method as set forth in any one of embodiments 12-3, wherein comparing the morphology of the anterior set of electrode signals and the morphology of the posterior set of electrode signals comprises determining whether the morphology of the posterior set of electrode signals is predominately opposite the morphology of the anterior set of electrode signals.

Embodiment 15

The method as set forth in any one of embodiments 12-14, the method further comprising determining an activation time of the QRS complex of the cardiac cycle for each electrode signal of the anterior set of electrode signals and the posterior set of electrode signals, wherein comparing the morphology of the anterior set of electrode signals and the morphology of the posterior set of electrode signals comprises comparing the activation times of the anterior set of electrode signals and the activation times of the posterior set of electrode signals.

Embodiment 16

The method as set forth in any one of embodiments 12-15, the method further comprising determining an amplitude of the QRS complex of the cardiac cycle for each electrode signal of the anterior set of electrode signals and the posterior set of electrode signals, wherein comparing the morphology of the anterior set of electrode signals and the morphology of the posterior set of electrode signals comprises comparing the amplitudes of the anterior set of electrode signals and the amplitudes of the posterior set of electrode signals.

Embodiment 17

The method as set forth in any one of embodiments 12-16, wherein comparing the morphology of the anterior set of electrode signals and the morphology of the posterior set of electrode signals comprises determining a metric of electrical heterogeneity comparing the anterior set of electrode signals and the posterior set of electrode signals, wherein the metric of electrical heterogeneity comprises at least one of:

ventricular electrical uncoupling metric based in a difference between an average of activation times of the posterior set of electrode signals and an average of activation times of the anterior set of electrode signals;

composite area under the curve metric based on of the area under the curve of the anterior set of electrode signals and the area under the curve of the posterior set of electrode signals;

composite height metric based on the maximum heights of each of the anterior set of electrode signals and the maximum heights of each of the posterior set of electrode signals; and composite inter-activation event activation distance based on the distance between each activation time of the anterior set of electrode signals and each activation time of the posterior set of electrode signals.

Embodiment 18

The method as set forth in any one of embodiments 12-17, the method further comprising:
initiating cardiac therapy to the patient applying a plurality of different cardiac therapy settings over a plurality of cardiac cycles; and
displaying on a graphical user interface a plurality of single-cycle graphs, each single-cycle graph corresponding to a different cardiac cycle where different cardiac therapy settings are applied, each single-cycle graph including all of the posterior set of electrode signals and the anterior set of electrode signals.

Embodiment 19

The method as set forth in embodiment 18, wherein comparing the anterior set of electrode signals and the posterior set of electrode signals comprises determining a metric of electrical heterogeneity based on the anterior set of electrode signals and the posterior set of electrode signals for each different cardiac cycle where different cardiac therapy settings are applied, wherein the computing apparatus is further configured to display the metric of electrical heterogeneity for each different cardiac cycle where different cardiac therapy settings are applied proximate the corresponding single-cycle graph, wherein the metric of electrical heterogeneity comprises at least one of:
ventricular electrical uncoupling metric based in a difference between an average of activation times of the posterior set of electrode signals and an average of activation times of the anterior set of electrode signals;
composite area under the curve metric based on of the area under the curve of the anterior set of electrode signals and the area under the curve of the posterior set of electrode signals;
composite height metric based on the maximum heights of each of the anterior set of electrode signals and the maximum heights of each of the posterior set of electrode signals; and
composite inter-activation event activation distance based on the distance between each activation time of the anterior set of electrode signals and each activation time of the posterior set of electrode signals.

Embodiment 20

The method as set forth in any one of embodiments 18-19, wherein the plurality of different cardiac settings comprises one or more of selection between intrinsic rhythm, left ventricular-only pacing and biventricular pacing, V-V pacing delay, and A-V pacing delay.

Embodiment 21

The method as set forth in any one of embodiments 18-20, the method further comprising:
determining effective cardiac settings of the plurality of different cardiac therapy settings based the posterior set of electrode signals and the anterior set of electrodes; and
indicating a desired single-cycle graph of the plurality of single-cycle graphs on the graphical user interface that corresponds to the determined effective cardiac settings.

Embodiment 22

The method as set forth in any one of embodiments 12-21, the method further comprising:
initiating cardiac therapy to the patient applying a plurality of different cardiac therapy settings over a plurality of cardiac cycles; and
determining effective cardiac settings of the plurality of different cardiac therapy settings based on the posterior set of electrode signals and the anterior set of electrodes.

This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

What is claimed:

1. A system for use in cardiac evaluation comprising:
electrode apparatus comprising a plurality of external electrodes to be located proximate a patient's skin, wherein the plurality of external electrodes comprises:
a posterior set of electrodes located proximate the patient's posterior, and
an anterior set of electrodes located proximate the patient's anterior; and
computing apparatus comprising processing circuitry, the computing apparatus operably coupled to the electrode apparatus and configured to:
monitor electrical activity from the patient's skin using the plurality of external electrodes over a cardiac cycle resulting in a posterior set of electrode signals monitored from one or more of the posterior set of electrodes and an anterior set of electrode signals monitored from one or more of the anterior set of electrodes, and
compare a morphology of the anterior set of electrode signals and a morphology of the posterior set of electrode signals to assist in determination of electrical heterogeneity.

2. The system of claim 1, wherein comparing the morphology of the anterior set of electrode signals and the morphology of the posterior set of electrode signals comprises determining whether the morphology of the posterior set of electrode signals is similar to the morphology of the anterior set of electrode signals.

3. The system of claim 1, wherein comparing the morphology of the anterior set of electrode signals and the morphology of the posterior set of electrode signals comprises determining whether the morphology of the posterior set of electrode signals is predominately opposite the morphology of the anterior set of electrode signals.

4. The system of claim 1, wherein the computing apparatus is further configured to determine an activation time of the QRS complex of the cardiac cycle for each electrode signal of the anterior set of electrode signals and the posterior set of electrode signals,
wherein comparing the morphology of the anterior set of electrode signals and the morphology of the posterior set of electrode signals comprises comparing the activation times of the anterior set of electrode signals and the activation times of the posterior set of electrode signals.

5. The system of claim 1, wherein the computing apparatus is further configured to determine an amplitude of the QRS complex of the cardiac cycle for each electrode signal of the anterior set of electrode signals and the posterior set of electrode signals, wherein comparing the morphology of the anterior set of electrode signals and the morphology of the posterior set of electrode signals comprises comparing the amplitudes of the anterior set of electrode signals and the amplitudes of the posterior set of electrode signals.

6. The system of claim 1, wherein comparing the morphology of the anterior set of electrode signals and the morphology of the posterior set of electrode signals comprises determining a metric of electrical heterogeneity comparing the anterior set of electrode signals and the posterior set of electrode signals, wherein the metric of electrical heterogeneity comprises at least one of:

ventricular electrical uncoupling metric based on a difference between an average of activation times of the posterior set of electrode signals and an average of activation times of the anterior set of electrode signals;

composite area under the curve metric based on the area under the curve of the anterior set of electrode signals and the area under the curve of the posterior set of electrode signals;

composite height metric based on the maximum heights of each of the anterior set of electrode signals and the maximum heights of each of the posterior set of electrode signals; and composite inter-activation event activation distance based on the distance between each activation time of the anterior set of electrode signals and each activation time of the posterior set of electrode signals.

7. The system of claim 1, the system further comprising a display comprising a graphical user interface to present cardiac signal information, wherein the computing apparatus is further configured to:

initiate cardiac therapy to the patient applying a plurality of different cardiac therapy settings over a plurality of cardiac cycles; and display on the graphical user interface a plurality of single-cycle graphs, each single-cycle graph corresponding to a different cardiac cycle where different cardiac therapy settings are applied, each single-cycle graph including all of the posterior set of electrode signals and the anterior set of electrode signals.

8. The system of claim 7, wherein comparing the anterior set of electrode signals and the posterior set of electrode signals comprises determining a metric of electrical heterogeneity based on the anterior set of electrode signals and the posterior set of electrode signals for each different cardiac cycle where different cardiac therapy settings are applied, wherein the computing apparatus is further configured to display the metric of electrical heterogeneity for each different cardiac cycle where different cardiac therapy settings are applied proximate the corresponding single-cycle graph, wherein the metric of electrical heterogeneity comprises at least one of:

ventricular electrical uncoupling metric based on a difference between an average of activation times of the posterior set of electrode signals and an average of activation times of the anterior set of electrode signals;

composite area under the curve metric based on the area under the curve of the anterior set of electrode signals and the area under the curve of the posterior set of electrode signals;

composite height metric based on the maximum heights of each of the anterior set of electrode signals and the maximum heights of each of the posterior set of electrode signals; and composite inter-activation event activation distance based on the distance between each activation time of the anterior set of electrode signals and each activation time of the posterior set of electrode signals.

9. The system of claim 7, wherein the plurality of different cardiac settings comprises one or more of selection between intrinsic rhythm, left ventricular-only pacing and biventricular pacing, V-V pacing delay, and A-V pacing delay.

10. The system of claim 7, wherein the computing apparatus is further configured to:

determine effective cardiac settings of the plurality of different cardiac therapy settings based on the posterior set of electrode signals and the anterior set of electrodes; and indicate a desired single-cycle graph of the plurality of single-cycle graphs on the graphical user interface that corresponds to the determined effective cardiac settings.

11. The system of claim 1, wherein the computing apparatus is further configured to:

initiate cardiac therapy to the patient applying a plurality of different cardiac therapy settings over a plurality of cardiac cycles; and determine effective cardiac settings of the plurality of different cardiac therapy settings based on the posterior set of electrode signals and the anterior set of electrodes.

12. A method for use in cardiac evaluation comprising:

monitoring electrical activity from a patient's skin using a plurality of external electrodes over a cardiac cycle resulting in a posterior set of electrode signals monitored from one or more of a posterior set of electrodes located proximate the patient's posterior and an anterior set of electrode signals monitored from one or more of an anterior set of electrodes located proximate the patient's anterior; and comparing a morphology of the anterior set of electrode signals and a morphology of the posterior set of electrode signals to assist in determination of electrical heterogeneity.

13. The method of claim 12, wherein comparing the morphology of the anterior set of electrode signals and the morphology of the posterior set of electrode signals comprises determining whether the morphology of the posterior set of electrode signals is similar to the morphology of the anterior set of electrode signals.

14. The method of claim 12, wherein comparing the morphology of the anterior set of electrode signals and the morphology of the posterior set of electrode signals comprises determining whether the morphology of the posterior set of electrode signals is predominately opposite the morphology of the anterior set of electrode signals.

15. The method of claim 12, the method further comprising determining an activation time of the QRS complex of the cardiac cycle for each electrode signal of the anterior set of electrode signals and the posterior set of electrode signals, wherein comparing the morphology of the anterior set of electrode signals and the morphology of the posterior set of electrode signals comprises comparing the activation times of the anterior set of electrode signals and the activation times of the posterior set of electrode signals.

16. The method of claim 12, the method further comprising determining an amplitude of the QRS complex of the cardiac cycle for each electrode signal of the anterior set of electrode signals and the posterior set of electrode signals,
wherein comparing the morphology of the anterior set of electrode signals and the morphology of the posterior set of electrode signals comprises comparing the amplitudes of the anterior set of electrode signals and the amplitudes of the posterior set of electrode signals.

17. The method of claim 12, wherein comparing the morphology of the anterior set of electrode signals and the morphology of the posterior set of electrode signals comprises determining a metric of electrical heterogeneity comparing the anterior set of electrode signals and the posterior set of electrode signals, wherein the metric of electrical heterogeneity comprises at least one of:
 ventricular electrical uncoupling metric based on a difference between an average of activation times of the posterior set of electrode signals and an average of activation times of the anterior set of electrode signals;
 composite area under the curve metric based on the area under the curve of the anterior set of electrode signals and the area under the curve of the posterior set of electrode signals;
 composite height metric based on the maximum heights of each of the anterior set of electrode signals and the maximum heights of each of the posterior set of electrode signals; and
 composite inter-activation event activation distance based on the distance between each activation time of the anterior set of electrode signals and each activation time of the posterior set of electrode signals.

18. The method of claim 12, the method further comprising:
 initiating cardiac therapy to the patient applying a plurality of different cardiac therapy settings over a plurality of cardiac cycles; and
 displaying on a graphical user interface a plurality of single-cycle graphs, each single-cycle graph corresponding to a different cardiac cycle where different cardiac therapy settings are applied, each single-cycle graph including all of the posterior set of electrode signals and the anterior set of electrode signals.

19. The method of claim 18, wherein comparing the anterior set of electrode signals and the posterior set of electrode signals comprises determining a metric of electrical heterogeneity based on the anterior set of electrode signals and the posterior set of electrode signals for each different cardiac cycle where different cardiac therapy settings are applied, wherein the computing apparatus is further configured to display the metric of electrical heterogeneity for each different cardiac cycle where different cardiac therapy settings are applied proximate the corresponding single-cycle graph, wherein the metric of electrical heterogeneity comprises at least one of:
 ventricular electrical uncoupling metric based on a difference between an average of activation times of the posterior set of electrode signals and an average of activation times of the anterior set of electrode signals;
 composite area under the curve metric based on the area under the curve of the anterior set of electrode signals and the area under the curve of the posterior set of electrode signals;
 composite height metric based on the maximum heights of each of the anterior set of electrode signals and the maximum heights of each of the posterior set of electrode signals; and
 composite inter-activation event activation distance based on the distance between each activation time of the anterior set of electrode signals and each activation time of the posterior set of electrode signals.

20. The method of claim 18, wherein the plurality of different cardiac settings comprises one or more of selection between intrinsic rhythm, left ventricular-only pacing and biventricular pacing, V-V pacing delay, and A-V pacing delay.

21. The method of claim 18, the method further comprising:
 determining effective cardiac settings of the plurality of different cardiac therapy settings based on the posterior set of electrode signals and the anterior set of electrodes; and
 indicating a desired single-cycle graph of the plurality of single-cycle graphs on the graphical user interface that corresponds to the determined effective cardiac settings.

22. The method of claim 12, the method further comprising:
 initiating cardiac therapy to the patient applying a plurality of different cardiac therapy settings over a plurality of cardiac cycles; and
 determining effective cardiac settings of the plurality of different cardiac therapy settings based on the posterior set of electrode signals and the anterior set of electrodes.

* * * * *